US007250250B2

(12) United States Patent
Alroy et al.

(10) Patent No.: US 7,250,250 B2
(45) Date of Patent: Jul. 31, 2007

(54) POSH NUCLEIC ACIDS, POLYPEPTIDES AND RELATED METHODS

(75) Inventors: Iris Alroy, Ness-Ziona (IL); Tsvika Greener, Ness-Ziona (IL); Shmuel Tuvia, Netanya (IL); Danny Ben-Avraham, Tel-Aviv (IL)

(73) Assignee: Proteologics, Inc., Orangeburg, NY (US)

( * ) Notice: Subject to any disclaimer, the term of this patent is extended or adjusted under 35 U.S.C. 154(b) by 368 days.

(21) Appl. No.: 10/293,965

(22) Filed: Nov. 12, 2002

(65) Prior Publication Data

US 2004/0025196 A1    Feb. 5, 2004

Related U.S. Application Data

(60) Provisional application No. 60/364,530, filed on Mar. 15, 2002, provisional application No. 60/345,846, filed on Nov. 9, 2001.

(51) Int. Cl.
*C12Q 1/00* (2006.01)
*C12Q 3/00* (2006.01)
*C07K 14/00* (2006.01)

(52) U.S. Cl. .......................................... 435/4; 530/350
(58) Field of Classification Search ................. 435/7.8, 435/7.91, 69.1; 530/350
See application file for complete search history.

(56) References Cited

U.S. PATENT DOCUMENTS

| 6,500,653 B1 | 12/2002 | Abo et al. |
| 6,511,825 B1 | 1/2003 | Ruggieri et al. |
| 6,743,619 B1 | 6/2004 | Tang et al. |
| 6,919,193 B2 | 7/2005 | Tang et al. |

FOREIGN PATENT DOCUMENTS

| EP | 1 074 617 A2 | 2/2001 |
| WO | WO-00/27865 | 5/2000 |
| WO | WO-01/18542 A2 | 3/2001 |
| WO | WO-01/54733 A1 | 8/2001 |
| WO | WO-01/55318 A2 | 8/2001 |
| WO | WO-01/55322 A2 | 8/2001 |
| WO | WO-01/57190 A2 | 8/2001 |
| WO | WO-01/60860 A2 | 8/2001 |
| WO | WO-01/64835 A2 | 9/2001 |
| WO | WO-01/70979 A2 | 9/2001 |
| WO | WO-01/71042 A2 | 9/2001 |
| WO | WO 0170979 A | 9/2001 |
| WO | WO-01/77288 A2 | 10/2001 |
| WO | WO-01/88088 A2 | 11/2001 |
| WO | WO-02/24956 A2 | 3/2002 |
| WO | WO-02/33046 A2 | 3/2002 |
| WO | WO-02/053719 A2 | 7/2002 |
| WO | WO-02/057414 A2 | 7/2002 |
| WO | WO-02/059377 A2 | 8/2002 |
| WO | WO-02/070737 A2 | 9/2002 |
| WO | WO-02/077235 A2 | 10/2002 |
| WO | WO-02/078524 A2 | 10/2002 |
| WO | WO-02/079449 A2 | 10/2002 |
| WO | WO-02/085285 A2 | 10/2002 |
| WO | WO-02/095000 A2 | 11/2002 |
| WO | WO-03/008647 A2 | 1/2003 |
| WO | WO-03/022987 A2 | 3/2003 |
| WO | WO-03/025138 A2 | 3/2003 |
| WO | WO-03/033646 A2 | 4/2003 |
| WO | WO-03/038130 A2 | 5/2003 |
| WO | WO-03/039490 A2 | 5/2003 |

OTHER PUBLICATIONS

Waterman et al. J. B. C. August 1999, vol. 274, No. 32, pp. 22151-22154.*
Lupher et al. The international Journal of Biochemistry & Cell Biology 1998, vol. 30, pp. 439-444.*
Tokumoto et al. Biochimica et Biophysics Acts 2000, vol. 1494, pp. 259-263.*
Yokouchi et al. J. B. C. Sep. 2001, vol. 276, No. 37, pp. 35185-35193.*
Claudio et al. Science 1999, vol. 286, pp. 309-312.*
Lee et al. FEBS, 2001, vol. 503, pp. 61-64.*
Scaife et al. J. Cell Science 2000, vol. 113, pp. 215-226.*
Parkinson et al. J. Virol. 2001, vol. 75, No. 11, pp. 5357-5362.*
Tapon, N. et al. A new Rac target POSH is an SH3-containing scaffold protein involved in the JNK and NF-kappaB signalling pathways. EMBO Journal. 17:5, 1395-1404 (1998).
Lazar et al., "Transforming Growth Factor α: Mutation of Aspartic Acid 47 and Leucine 48 Results in Different Biological Activities", Molecular and Cellular Biology, vol. 8:3, pp. 1247-1252 (1988).
Smilek et al., "A Single Amino Acid Change in a Myelin Basic Protein Peptide Confers the Capacity to Prevent Rather Than Induce Experimental Autoimmune Encephalomyelitis", Proc. National Academy Science USA, vol. 88, pp. 9633-9637 (1991).

* cited by examiner

*Primary Examiner*—Bruce R. Campell
*Assistant Examiner*—Bao Qun Li
(74) *Attorney, Agent, or Firm*—Fish & Neave IP Group, Ropes & Gray LLP

(57) ABSTRACT

The application discloses novel polypeptides and nucleic acids involved in a variety of biological processes, including viral reproduction. Related methods and compositions are also described.

6 Claims, 27 Drawing Sheets

Human POSH Coding Sequence (SEQ ID NO:1)
ATGGATGAATCAGCCTTGTTGGATCTTTTGGAGTGTCCGGTGTGTCTAGAGCGCCTTGATGCTTCTGCGA
AGGTCTTGCCTTGCCAGCATACGTTTTGCAAGCGATGTTTGCTGGGGATCGTAGGTTCTCGAAATGAACT
CAGATGTCCCGAGTGCAGGACTCTTGTTGGCTCGGGTGTCGAGGAGCTTCCCAGTAACATCTTGCTGGTC
AGACTTCTGGATGGCATCAAACAGAGGCCTTGGAAACCTGGTCCTGGTGGGGAAGTGGGACCAACTGCA
CAAATGCATTAAGGTCTCAGAGCAGCACTGTGGCTAATTGTAGCTCAAAAGATCTGCAGAGCTCCCAGGG
CGGACAGCAGCCTCGGGTGCAATCCTGGAGCCCCCAGTGAGGGGTATACCTCAGTTACCATGTGCCAAA
GCGTTATACAACTATGAAGGAAAAGAGCCTGGAGACCTTAAATTCAGCAAAGGCGACATCATCATTTTGC
GAAGACAAGTGGATGAAAATTGGTACCATGGGAAGTCAATGAATCCATGGCTTTTTCCCCACCAACTT
TGTGCAGATTATTAAACCGTTACCTCAGCCCCCACCTCAGTGCAAAGCACTTTATGACTTTGAAGTGAAA
GACAAGGAAGCAGACAAAGATTGCCTTCCATTTGCAAAGGATGATGTTCTGACTGTGATCCGAAGAGTGG
ATGAAAACTGGGCTGAAGGAATGCTGGCAGACAAAATAGGAATATTTCCAATTTCATATGTTGAGTTTAA
CTCGGCTGCTAAGCAGCTGATAGAATGGGATAAGCCTCCTGTGCCAGGAGTTGATGCTGGAGAATGTTCC
TCGGCAGCAGCCCAGAGCAGCACTGCCCCAAAGCACTCCGACACCAAGAAGAACACCAAAAAGCGGCACT
CCTTCACTTCCCTCACTATGGCCAACAAGTCCTCCCAGGCATCCCAGAACCGCCACTCCATGGAGATCAG
CCCCCCTGTCCTCATCAGCTCCAGCAACCCCACTGCTGCTGCACGGATCAGCGAGCTGTCTGGGCTCTCC
TGCAGTGCCCCTTCTCAGGTTCATATAAGTACCACCGGGTTAATTGTGACCCCGCCCCAAGCAGCCCAG
TGACAACTGGCCCCTCGTTTACTTTCCCATCAGATGTTCCCTACCAAGCTGCCCTTGGAACTTTGAATCC
TCCTCTTCCACCACCCCCTCTCCTGGCTGCCACTGTCCTTGCCTCCACACCACCAGGCGCCACCGCCGCC
GCTGCTGCTGCTGGAATGGGACCGAGGCCCATGGCAGGATCCACTGACCAGATTGCACATTTACGGCCGC
AGACTCGCCCCAGTGTGTATGTTGCTATATATCCATACACTCCTCGGAAAGAGGATGAACTAGAGCTGAG
AAAAGGGGAGATGTTTTTAGTGTTTGAGCGCTGCCAGGATGGCTGGTTCAAAGGGACATCCATGCATACC
AGCAAGATAGGGGTTTTCCCTGGCAATTATGTGGCACCAGTCACAAGGGCGGTGACAAATGCTTCCCAAG
CTAAAGTCCCTATGTCTACAGCTGGCCAGACAAGTCGGGGAGTGACCATGGTCAGTCCTTCCACGGCAGG
AGGGCCTGCCCAGAAGCTCCAGGGAAATGGCGTGGCTGGGAGTCCCAGTGTTGTCCCCGCAGCTGTGGTA
TCAGCAGCTCACATCCAGACAAGTCCTCAGGCTAAGGTCTTGTTGCACATGACGGGGCAAATGACAGTCA
ACCAGGCCCGCAATGCTGTGAGGACAGTTGCAGCGCACAACCAGGAACGCCCCACGGCAGCAGTGACACC
CATCCAGGTACAGAATGCCGCCGGCCTCAGCCCTGCATCTGTGGGCCTGTCCCATCACTCGCTGGCCTCC
CCACAACCTGCGCCTCTGATGCCAGGCTCAGCCACGCACACTGCTGCCATCAGTATCAGTCGAGCCAGTG
CCCCTCTGGCCTGTGCAGCAGCTGCTCCACTGACTTCCCCAAGCATCACCAGTGCTTCTCTGGAGGCTGA
GCCCAGTGGCCGGATAGTGACCGTTCTCCCTGGACTCCCCACATCTCCTGACAGTGCTTCATCAGCTTGT
GGGAACAGTTCAGCAACCAAACCAGACAAGGATAGCAAAAAAGAAAAAAAGGGTTTGTTGAAGTTGCTTT
CTGGCGCCTCCACTAAACGGAAGCCCGCGTGTCTCCTCCAGCATCGCCCACCCTAGAAGTGGAGCTGGG
CAGTGCAGAGCTTCCTCTCCAGGGAGCGGTGGGGCCCGAACTGCCACCAGGAGGTGGCCATGGCAGGGCA
GGCTCCTGCCCTGTGGACGGGGACGGACCGGTCACGACTGCAGTGGCAGGAGCAGCCCTGGCCCAGGATG
CTTTTCATAGGAAGGCAAGTTCCCTGGACTCCGCAGTTCCCATCGCTCCACCTCCTCGCCAGGCCTGTTC
CTCCCTGGGTCCTGTCTTGAATGAGTCTAGACCTGTCGTTTGTGAAAGGCACAGGGTGGTGGTTTCCTAT
CCTCCTCAGAGTGAGGCAGAACTTGAACTTAAAGAAGGAGATATTGTGTTTGTTCATAAAAAACGAGAGG
ATGGCTGGTTCAAAGGCACATTACAACGTAATGGGAAAACTGGCCTTTTCCCAGGAAGCTTTGTGGAAAA
CATATGA

Fig. 1

Human POSH Amino Acid Sequence (SEQ ID NO:2)

MDESALLDLLECPVCLERLDASAKVLPCQHTFCKRCLLGIVGSRNELRCPECRTLVGSGVEELPSNILLV
RLLDGIKQRPWKPGPGGGSGTNCTNALRSQSSTVANCSSKDLQSSQGGQQPRVQSWSPPVRGIPQLPCAK
ALYNYEGKEPGDLKFSKGDIIILRRQVDENWYHGEVNGIHGFFPTNFVQIIKPLPQPPPQCKALYDFEVK
DKEADKDCLPFAKDDVLTVIRRVDENWAEGMLADKIGIFPISYVEFNSAAKQLIEWDKPPVPGVDAGECS
SAAAQSSTAPKHSDTKKNTKKRHSFTSLTMANKSSQASQNRHSMEISPPVLISSSNPTAAARISELSGLS
CSAPSQVHISTTGLIVTPPPSSPVTTGPSFTFPSDVPYQAALGTLNPPLPPPPLLAATVLASTPPGATAA
AAAAGMGPRPMAGSTDQIAHLRPQTRPSVYVAIYPYTPRKEDELELRKGEMFLVFERCQDGWFKGTSMHT
SKIGVFPGNYVAPVTRAVTNASQAKVPMSTAGQTSRGVTMVSPSTAGGPAQKLQGNGVAGSPSVVPAAVV
SAAHIQTSPQAKVLLHMTGQMTVNQARNAVRTVAAHNQERPTAAVTPIQVQNAAGLSPASVGLSHHSLAS
PQPAPLMPGSATHTAAISISRASAPLACAAAAPLTSPSITSASLEAEPSGRIVTVLPGLPTSPDSASSAC
GNSSATKPDKDSKKEKKGLLKLLSGASTKRKPRVSPPASPTLEVELGSAELPLQGAVGPELPPGGGHGRA
GSCPVDGDGPVTTAVAGAALAQDAFHRKASSLDSAVPIAPPPRQACSSLGPVLNESRPVVCERHRVVVSY
PPQSEAELELKEGDIVFVHKKREDGWFKGTLQRNGKTGLFPGSFVENI

Fig. 2

Human POSH cDNA Sequence (SEQ ID NO:3)

```
CTGAGAGACACTGCGAGCGGCGAGCGCGGTGGGCCGCATCTGCATCAGCCGCCGCAGCCGCTGCGGGGC
CGCGAACAAAGAGGAGGAGCCGAGGCGCGAGAGCAAAGTCTGAAATGGATGTTACATGAGTCATTTTAAG
GGATGCACACAACTATGAACATTTCTGAAGATTTTTTCTCAGTAAAGTAGATAAAGATGGATGAATCAGC
CTTGTTGGATCTTTTGGAGTGTCCGGTGTGTCTAGAGCGCCTTGATGCTTCTGCGAAGGTCTTGCCTTGC
CAGCATACGTTTTGCAAGCGATGTTTGCTGGGGATCGTAGGTTCTCGAAATGAACTCAGATGTCCCGAGT
GCAGGACTCTTGTTGGCTCGGGTGTCGAGGAGCTTCCCAGTAACATCTTGCTGGTCAGACTTCTGGATGG
CATCAAACAGAGGCCTTGGAAACCTGGTCCTGGTGGGGGAAGTGGGACCAACTGCACAAATGCATTAAGG
TCTCAGAGCAGCACTGTGGCTAATTGTAGCTCAAAAGATCTGCAGAGCTCCCAGGGCGGACAGCAGCCTC
GGGTGCAATCCTGGAGCCCCCCAGTGAGGGGTATACCTCAGTTACCATGTGCCAAAGCGTTATACAACTA
TGAAGGAAAAGAGCCTGGAGACCTTAAATTCAGCAAAGGCGACATCATCATTTTGCGAAGACAAGTGGAT
GAAAATTGGTACCATGGGGAAGTCAATGGAATCCATGGCTTTTCCCCACCAACTTTGTGCAGATTATTA
AACCGTTACCTCAGCCCCCACCTCAGTGCAAAGCACTTTATGACTTTGAAGTGAAAGACAAGGAAGCAGA
CAAAGATTGCCTTCCATTTGCAAAGGATGATGTTCTGACTGTGATCCAAGAGTGGATGAAAACTGGGCT
GAAGGAATGCTGGCAGACAAAATAGGAATATTTCCAATTTCATATGTTGAGTTTAACTCGGCTGCTAAGC
AGCTGATAGAATGGGATAAGCCTCCTGTGCCAGGAGTTGATGCTGGAGAATGTTCCTCGGCAGCAGCCCA
GAGCAGCACTGCCCCAAAGCACTCCGACACCAAGAAGAACACCAAAAAGCGGCACTCCTTCACTTCCCTC
ACTATGGCCAACAAGTCCTCCCAGGCATCCCAGAACCGCCACTCCATGGAGATCAGCCCCCTGTCCTCA
TCAGCTCCAGCAACCCCACTGCTGCTGCACGGATCAGCGAGCTGTCTGGGCTCTCCTGCAGTGCCCCTTC
TCAGGTTCATATAAGTACCACCGGGTTAATTGTGACCCCGCCCCCAAGCAGCCCAGTGACAACTGGCCCC
TCGTTTACTTTCCCATCAGATGTTCCCTACCAAGCTGCCCTTGGAACTTTGAATCCTCCTCTTCCACCAC
CCCCTCTCCTGGCTGCCACTGTCCTTGCCTCCACACCACCAGGCGCCACCGCCGCCGCTGCTGCTGCTGG
AATGGGACCGAGGCCCATGGCAGGATCCACTGACCAGATTGCACATTTACGGCCGCAGACTCGCCCCAGT
GTGTATGTTGCTATATATCCATACACTCCTCGGAAAGAGGATGAACTAGAGCTGAGAAAAGGGGAGATGT
TTTTAGTGTTTGAGCGCTGCCAGGATGGCTGGTTCAAAGGGACATCCATGCATACCAGCAAGATAGGGGT
TTTCCCTGGCAATTATGTGGCACCAGTCACAAGGGCGGTGACAAATGCTTCCCAAGCTAAAGTCCCTATG
TCTACAGCTGGCCAGACAAGTCGGGGAGTGACCATGGTCAGTCCTTCCACGGCAGGAGGGCCTGCCCAGA
AGCTCCAGGGAAATGGCGTGGCTGGGAGTCCCAGTGTTGTCCCCGCAGCTGTGGTATCAGCAGCTCACAT
CCAGACAAGTCCTCAGGCTAAGGTCTTGTTGCACATGACGGGGCAAATGACAGTCAACCAGGCCCGCAAT
GCTGTGAGGACAGTTGCAGCGCACAACCAGGAACGCCCCACGGCAGCAGTGACACCCATCCAGGTACAGA
ATGCCGCCGGCCTCAGCCCTGCATCTGTGGGCCTGTCCCATCACTCGCTGGCCTCCCCACAACCTGCGCC
TCTGATGCCAGGCTCAGCCACGCACACTGCTGCCATCAGTATCAGTCGAGCCAGTGCCCCTCTGGCCTGT
GCAGCAGCTGCTCCACTGACTTCCCCAAGCATCACCAGTGCTTCTCTGGAGGCTGAGCCCAGTGGCCGGA
TAGTGACCGTTCTCCCTGGACTCCCCACATCTCCTGACAGTGCTTCATCAGCTTGTGGGAACAGTTCAGC
AACCAAACCAGACAAGGATAGCAAAAAAGAAAAAAAGGGTTTGTTGAAGTTGCTTTCTGGCGCCTCCACT
AAACGGAAGCCCCGCGTGTCTCCTCCAGCATCGCCCACCCTAGAAGTGGAGCTGGGCAGTGCAGAGCTTC
CTCTCCAGGGAGCGGTGGGGCCCGAACTGCCACCAGGAGGTGGCCATGGCAGGGCAGGCTCCTGCCCTGT
GGACGGGGACGGACCGGTCACGACTGCAGTGGCAGGAGCAGCCCTGGCCCAGGATGCTTTTCATAGGAAG
GCAAGTTCCCTGGACTCCGCAGTTCCCATCGCTCCACCTCCTCGCCAGGCCTGTTCCTCCCTGGGTCCTG
TCTTGAATGAGTCTAGACCTGTCGTTTGTGAAAGGCACAGGGTGGTGGTTTCCTATCCTCCTCAGAGTGA
GGCAGAACTTGAACTTAAAGAAGGAGATATTGTGTTTGTTCATAAAAAACGAGAGGATGGCTGGTTCAAA
GGCACATTACAACGTAATGGGAAAACTGGCCTTTTCCCAGGAAGCTTTGTGGAAAACATATGAGGAGACT
GACACTGAAGAAGCTTAAAATCACTTCACACAACAAAGTAGCACAAAGCAGTTTAACAGAAAGAGCACAT
TTGTGGACTTCCAGATGGTCAGGAGATGAGCAAAGGATTGGTATGTGACTCTGATGCCCCAGCACAGTTA
CCCCAGCGAGCAGAGTGAAGAAGATGTTTGTGTGGGTTTTGTTAGTCTGGATTCGGATGTATAAGGTGTG
CCTTGTACTGTCTGATTTACTACACAGAGAAACTTTTTTTTTTTTAAGATATATGACTAAAATGGACA
ATTGTTTACAAGGCTTAACTAATTTATTTGCTTTTTTAAACTTGAACTTTTCGTATAATAGATACGTTCT
TTGGATTATGATTTTAAGAAATTATTAATTTATGAAATGATAGGTAAGGAGAAGCTGGATTATCTCCTGT
TGAGAGCAAGAGATTCGTTTTGACATAGAGTGAATGCATTTTCCCCTCTCCTCCTCCCTGCTACCATTAT
ATTTTGGGGTTATGTTTTGCTTCTTTAAGATAGAAATCCCAGTTCTCTAATTTGGTTTTCTTCTTTGGGA
AACCAAACATACAAATGAATCAGTATCAATTAGGGCCTGGGGTAGAGAGACAGAAACTTGAGAGAAGAGA
AGTTAGTGATTCCCTCTCTTTCTAGTTTGGTAGGAATCACCCTGAAGACCTAGTCCTCAATTTAATTGTG
TGGGTTTTTAATTTTCCTAGAATGAAGTGACTGAAACAATGAGAAAGAATACAGCACAACCCTTGAACAA
AATGTATTTAGAAATATATTTAGTTTTATAGCAGAAGCAGCTCAATTGTTTGGTTGGAAAGTAGGGGAAA
TTGAAGTTGTAGTCACTGTCTGAGAATGGCTATGAAGCGTCATTTCACATTTTACCCCAACTGACCTGCA
```

Fig. 3-1

```
TGCCCAGGACACAAGTAAAACATTTGTGAGATAGTGGTGGTAAGTGATGCACTCGTGTTAAGTCAAAGGC
TATAAGAAACACTGTGAAAAGTTCATATTCATCCATTGTGATTCTTTCCCCACGTCTTGCATGTATTACT
GGATTCCCACAGTAATATAGACTGTGCATGGTGTGTATATTTCATTGCGATTTCCTGTTAAGATGAGTTT
GTACTCAGAATTGACCAATTCAGGAGGTGTAAAAATAAACAGTGTTCTCTTCTCTACCCCAAAGCCACTA
CTGACCAAGGTCTCTTCAGTGCACTCGCTCCCTCTCTGGCTAAGGCATGCATTAGCCACTACACAAGTCA
TTAGTGAAAGTGGTCTTTTATGTCCTCCCAGCAGACAGACATCAAGGATGAGTTAACCAGGAGACTACTC
CTGTGACTGTGGAGCTCTGGAAGGCTTGGTGGGAGTGAATTTGCCCACACCTTACAATTGTGGCAGGATC
CAGAAGAGCCTGTCTTTTTATATCCATTCCTTGATGTCATTGGCCTCTCCCACCGATTTCATTACGGTGC
CACGCAGTCATGGATCTGGGTAGTCCGGAAAACAAAAGGAGGGAAGACAGCCTGGTAATGAATAAGATCC
TTACCACAGTTTTCTCATGGGAAATACATAATAAACCCTTTCATCTTTTTTTTTTCCTTTAAGAATTAA
AACTGGGAAATAGAAACATGAACTGAAAAGTCTTGCAATGACAAGAGGTTTCATGGTCTTAAAAAGATAC
TTTATATGGTTGAAGATGAAATCATTCCTAAATTAACCTTTTTTTAAAAAAAAAACAATGTATATTATGT
TCCTGTGTGTTGAATTTAAAAAAAAAAAATACTTTACTTGGATATTCATGTAATATATAAAGGTTTGGTG
AAATGAACTTTAGTTAGGAAAAAGCTGGCATCAGCTTTCATCTGTGTAAGTTGACACCAATGTGTCATAA
TATTCTTTATTTTGGGAATTAGTGTATTTATAAAAATTTTAAAAAGAAAAAAGACTACTACAGGTTAA
GATAATTTTTTTACCTGTCTTTTCTCCATATTTTAAGCTATGTGATTGAAGTACCTCTGTTCATAGTTTC
CTGGTATAAAGTTGGTTAAAATTTCATCTGTTAATAGATCATTAGGTAATATAATGTATGGGTTTTCTAT
TGGTTTTTTGCAGACAGTAGAGGGAGATTTTGTAACAAGGGCTTGTTACACAGTGATATGGTAATGATAA
AATTGCAATTTATCACTCCTTTTCATGTTAATAATTTGAGGACTGGATAAAAGGTTTCAAGATTAAAATT
TGATGTTCAAACCTTTGT
```

Fig. 3-2

5' cDNA fragment of human POSH (public gi:10432611; SEQ ID NO:4)
ctgagagacactgcgagcggcgagcgcggtggggccgcatctgcatcagccgccgcagccgctgcggggc
cgcgaacaaagaggaggagccgaggcgcgagagcaaagtctgaaatggatgttacatgagtcattttaag
gatgcacacaactatgaacatttctgaagatttttctcagtaaagtagataaagatggatgaatcagcc
ttgttggatcttttggagtgtccggtgtgtctagagcgccttgatgcttctgcgaaggtcttgccttgcc
agcatacgttttgcaagcgatgtttgctggggatcgtaggttctcgaaatgaactcagatgtcccgagtg
caggactcttgttggctcgggtgtcgaggagcttcccagtaacatcttgctggtcagacttctggatggc
atcaaacagaggccttggaaacctggtcctggtgggggaagtgggaccaactgcacaaatgcattaaggt
ctcagagcagcactgtggctaattgtagctcaaaagatctgcagagctcccagggcggacagcagcctcg
ggtgcaatcctggagccccccagtgaggggtatacctcagttaccatgtgccaaagcgttatacaactat
gaaggaaaagagcctggagaccttaaattcagcaaaggcgacatcatctttgcgaagacaagtggatg
aaaattggtaccatggggaagtcaatggaatccatggcttttcccccaccaactttgtgcagattattaa
accgttacctcagcccccacctcagtgcaaagcactttatgactttgaagtgaaagacaaggaagcagac
aaagattgccttccatttgcaaaggatgatgttctgactgtgatccgaagagtggatgaaaactgggctg
aaggaatgctggcagacaaaataggaatatttccaatttcatatgttgagtttaactcggctgctaagca
gctgatagaatgggataagcctcctgtgccaggagttgatgctggagaatgttcctcggcagcagcccag
agcagcactgccccaaagcactccgacaccaagaagaacaccaaaaagcggcactccttcacttccctca
ctatggccaacaagtcctcccaggcatcccagaaccgccactccatggagatcagccccctgtcctcat
cagctccagcaaccccactgctgctgcacggatcagcgagctgtctgggctctcctgcagtgccccttct
caggttcatataagtaccaccgggttaattgtgaccccgcccccaagcagcccagtgacaactggcccct
cgtttactttcccatcagatgttccctaccaagctgcccttggaactttgaatcctcctcttccaccacc
cctctcctggctgccactgtccttgcctccacaccaccaggcgccaccgccgccgctgctgctgctgga
atgggaccgaggcccatggcaggatccactgaccagattgcacatttacggccgcagactcgccccagtg
tgtatgttgctatatatccatacactcctcggaaagaggatgaactagagctgagaaaaggggagatgtt
tttagtgtttgagcgctgccaggatggctggttcaaagggacatccatgcataccagcaagataggggtt
ttccctggcaattatgtggcaccagtcacaagggcggtgacaaatgcttcccaagctaaagtccctatgt
ctacagctggccagacaagtcggggagtgaccatggtcagtccttccacggcaggagggcctgcccagaa
gctccagggaaatggcgtggctgggagtcccagtgttgtccccgcagctgtggtatcagcagctcacatc
cagacaagtcctcaggctaaggtcttgttgcacatgacggggcaaatgacagtcaaccaggcccgcaatg
ctgtgaggacagttgcagcgcacaaccaggaacgccccacggcagcagtgacacccatccaggtacagaa
tgccgccggcctcagccctgcatctgtgggcctgtccatcactcgctggcctcccacaacctgcgcct
ctgatgccaggctcagccacgcacactgctgccatcagtatcagtcgagccagtgcccctctggcctgtg
cagcagctgctccactgacttccccaagcatcaccagtgcttctctggaggctgagcccagtggccggat
agtgaccgttctccctggactccccacatctcctgacagtgcttcatcagcttgtgggaacagttcagca
accaaaccagacaaggatagc

Fig. 4

N terminus protein fragment of hPOSH (public gi:10432612; SEQ ID NO:5)
MDESALLDLLECPVCLERLDASAKVLPCQHTFCKRCLLGIVGSRNELRCPECRTLVGSGVEELPSNILLV
RLLDGIKQRPWKPGPGGGSGTNCTNALRSQSSTVANCSSKDLQSSQGGQQPRVQSWSPPVRGIPQLPCAK
ALYNYEGKEPGDLKFSKGDIIILRRQVDENWYHGEVNGIHGFFPTNFVQIIKPLPQPPPQCKALYDFEVK
DKEADKDCLPFAKDDVLTVIRRVDENWAEGMLADKIGIFPISYVEFNSAAKQLIEWDKPPVPGVDAGECS
SAAAQSSTAPKHSDTKKNTKKRHSFTSLTMANKSSQASQNRHSMEISPPVLISSSNPTAAARISELSGLS
CSAPSQVHISTTGLIVTPPPSSPVTTGPSFTFPSDVPYQAALGTLNPPLPPPPLLAATVLASTPPGATAA
AAAAGMGPRPMAGSTDQIAHLRPQTRPSVYVAIYPYTPRKEDELELRKGEMFLVFERCQDGWFKGTSMHT
SKIGVFPGNYVAPVTRAVTNASQAKVPMSTAGQTSRGVTMVSPSTAGGPAQKLQGNGVAGSPSVVPAAVV
SAAHIQTSPQAKVLLHMTGQMTVNQARNAVRTVAAHNQERPTAAVTPIQVQNAAGLSPASVGLSHHSLAS
PQPAPLMPGSATHTAAISISRASAPLACAAAAPLTSPSITSASLEAEPSGRIVTVLPGLPTSPDSASSAC
GNSSATKPDKDS

Fig. 5

3' mRNA fragment of hPOSH (public gi:7959248; SEQ ID NO:6)
atttcatatgttgagtttaactcggctgctaagcagctgatagaatgggataagcctcctgtgccaggag
ttgatgctggagaatgttcctcggcagcagcccagagcagcactgccccaaagcactccgacaccaagaa
gaacaccaaaaagcggcactccttcacttccctcactatggccaacaagtcctcccaggcatcccagaac
cgccactccatggagatcagccccctgtcctcatcagctccagcaacccactgctgctgcacggatca
gcgagctgtctgggctctcctgcagtgccccttctcaggttcatataagtaccaccgggttaattgtgac
cccgcccccaagcagcccagtgacaactggcccctcgtttactttccatcagatgttccctaccaagct
gcccttggaactttgaatcctcctcttccaccaccccctctcctggctgccactgtccttgcctccacac
caccaggcgccaccgccgctgctgctgctgctggaatgggaccgaggcccatggcaggatccactgacca
gattgcacatttacggccgcagactcgccccagtgtgtatgttgctatatatccatacactcctcggaaa
gaggatgaactagagctgagaaaaggggagatgttttagtgtttgagcgctgccaggatggctggttca
aagggacatccatgcataccagcaagataggggttttccctggcaattatgtggcaccagtcacaagggc
ggtgacaaatgcttcccaagctaaagtccctatgtctacagctggccagacaagtcggggagtgaccatg
gtcagtccttccacggcaggagggcctgcccagaagctccagggaaatggcgtggctgggagtcccagtg
ttgtccccgcagctgtggtatcagcagctcacatccagacaagtcctcaggctaaggtcttgttgcacat
gacggggcaaatgacagtcaaccaggcccgcaatgctgtgaggacagttgcagcgcacaaccaggaacgc
cccacggcagcagtgacacccatccaggtacagaatgccgccggcctcagccctgcatctgtgggcctgt
cccatcactcgctggcctccccacaacctgcgcctctgatgccaggctcagccacgcacactgctgccat
cagtatcagtcgagccagtgcccctctggcctgtgcagcagctgctccactgacttccccaagcatcacc
agtgcttctctggaggctgagcccagtggccggatagtgaccgttctccctggactccccacatctcctg
acagtgcttcatcagcttgtgggaacagttcagcaaccaaaccagacaaggatagcaaaaaagaaaaaaa
gggtttgttgaagttgctttctggcgcctccactaaacggaagcccgcgtgtctcctccagcatcgccc
accctagaagtggagctgggcagtgcagagcttcctctccagggagcggtggggcccgaactgccaccag
gaggtggccatggcagggcaggctcctgccctgtggacggggacggaccggtcacgactgcagtggcagg
agcagcctggcccaggatgcttttcataggaaggcaagttccctggactccgcagttcccatcgctcca
cctcctcgccaggcctgttcctccctgggtcctgtcttgaatgagtctagacctgtcgtttgtgaaaggc
acagggtggtggtttcctatcctcctcagagtgaggcagaacttgaacttaaagaaggagatattgtgtt
tgttcataaaaaacgagaggatggctggttcaaaggcacattacaacgtaatgggaaaactggcctttc
ccaggaagctttgtggaaaacatatgaggagactgacactgaagaagcttaaaatcacttcacacaacaa
agtagcacaaagcagtttaacagaaagagcacatttgtggacttccagatggtcaggagatgagcaaagg
attggtatgtgactctgatgccccagcacagttacccagcgagcagagtgaagaagatgtttgtgtggg
ttttgttagtctggattcggatgtataaggtgtgccttgtactgtctgatttactacacagagaaacttt
ttttttttttttaagatatatgactaaaatggacaattgtttacaaggcttaactaatttatttgcttttt
taaacttgaacttttcgtataatagatacgttctttggattatgatttaagaaattattaatttatgaa
atgataggtaaggagaagctggattatctcctgttgagagcaagagattcgttttgacatagagtgaatg
cattttcccctctcctcctccctgctaccattatatttggggttatgttttgcttctttaagatagaaa
tcccagttctctaatttggttttcttctttgggaaaccaaacatacaaatgaatcagtatcaattagggc
ctgggggtagagagacagaaacttgagagaagagaagttagtgattccctctctttctagtttggtaggaa
tcaccctgaagacctagtcctcaatttaattgtgtgggttttaattttcctagaatgaagtgactgaaa
caatgagaaagaatacagcacaacccttgaacaaaatgtatttagaaatatattagttttatagcagaa
gcagctcaattgtttggttggaaagtaggggaaattgaagttgtagtcactgtctgagaatggctatgaa
gcgtcatttcacatttacccccaactgacctgcatgcccaggacacaagtaaaacatttgtgagatagtg
gtggtaagtgatgcactcgtgttaagtcaaaggctataagaaacactgtgaaaagttcatattcatccat
tgtgattctttccccacgtcttgcatgtattactggattcccacagtaatatagactgtgcatggtgtgt
atatttcattgcgatttcctgttaagatgagtttgtactcagaattgaccaattcaggaggtgtaaaaat
aaacagtgttctcttctctaccccaaagccactactgaccaaggtctcttcagtgcactcgctccctctc
tggctaaggcatgcattagccactacacaagtcattagtgaaagtggtctttatgtcctcccagcagac
agacatcaaggatgagttaaccaggagactactcctgtgactgtggagctctggaaggcttggtgggagt
gaatttgcccacaccttacaattgtggcaggatccagaagagcctgtcttttatatccattccttgatg
tcattggcctctcccaccgatttcattacggtgccacgcagtcatggatctgggtagtccggaaaacaaa
aggagggaagacagcctggtaatgaataagatccttaccacagttttctcatgggaaatacataataaac
cctttcatctttttttttttcctttaagaattaaaactgggaaatagaaacatgaactgaaagtcttgc
aatgacaagaggtttcatggtcttaaaaagatactttatatggttgaagatgaaatcattcctaaattaa
ccttttttttaaaaaaaaacaatgtatattatgttcctgtgtgttgaatttaaaaaaaaaaaatacttta
cttggatattcatgtaatatataaaggtttggtgaaatgaactttagttaggaaaaagctggcatcagct

Fig. 6-1

```
ttcatctgtgtaagttgacaccaatgtgtcataatattctttatttttgggaaattagtgtattttataaa
aatttttaaaaagaaaaaagactactacaggttaagataattttttttacctgtcttttctccatattttaa
gctatgtgattgaagtacctctgttcatagtttcctggtataaagttggttaaaatttcatctgttaata
gatcattaggtaatataatgtatgggttttctattggttttttgcagacagtagagggagattttgtaac
aagggcttgttacacagtgatatggtaatgataaaattgcaatttatcactccttttcatgttaataatt
tgaggactggataaaaggtttcaagattaaaatttgatgttcaaacctttgt
```

Fig. 6-2

C terminus protein fragment of hPOSH (public gi:7959249; SEQ ID NO:7)
ISYVEFNSAAKQLIEWDKPPVPGVDAGECSSAAAQSSTAPKHSDTKKNTKKRHSFTSLTMANKSSQASQN
RHSMEISPPVLISSSNPTAAARISELSGLSCSAPSQVHISTTGLIVTPPPSSPVTTGPSFTFPSDVPYQA
ALGTLNPPLPPPPLLAATVLASTPPGATAAAAAAGMGPRPMAGSTDQIAHLRPQTRPSVYVAIYPYTPRK
EDELELRKGEMFLVFERCQDGWFKGTSMHTSKIGVFPGNYVAPVTRAVTNASQAKVPMSTAGQTSRGVTM
VSPSTAGGPAQKLQGNGVAGSPSVVPAAVVSAAHIQTSPQAKVLLHMTGQMTVNQARNAVRTVAAHNQER
PTAAVTPIQVQNAAGLSPASVGLSHHSLASPQPAPLMPGSATHTAAISISRASAPLACAAAAPLTSPSIT
SASLEAEPSGRIVTVLPGLPTSPDSASSACGNSSATKPDKDSKKEKKGLLKLLSGASTKRKPRVSPPASP
TLEVELGSAELPLQGAVGPELPPGGGHGRAGSCPVDGDGPVTTAVAGAALAQDAFHRKASSLDSAVPIAP
PPRQACSSLGPVLNESRPVVCERHRVVVSYPPQSEAELELKEGDIVFVHKKREDGWFKGTLQRNGKTGLF
PGSFVENI

Fig. 7

Human POSH full mRNA, Annotated Sequence

---- - gi|10432611|dbj|AK021429.1|AK021429 Homo sapiens cDNA FLJ11367 fis, clone HEMBA1000303, highly similar to Mus musculus Plenty of SH3s (POSH) mRNA ---- - gi|7959248|dbj|AB040927.1|AB040927 Homo sapiens mRNA for KIAA1494 protein, partial cds

 - Both hPOSH and KIAA1495

 - Ring Domain

 - SH3 Domain

 - start codon and stop codon of predicted ORF

CTGAGAGACACTGCGAGCGGCGAGCGCGGTGGGGCCGCATCTGCATCAGCCGCCGCAGCCGCTGCGGGGC
CGCGAACAAAGAGGAGGAGCCGAGGCGCGAGAGCAAAGTCTGAAATGGATGTTACATGAGTCATTTTAAG
GGATGCACACAACTATGAACATTTCTGAAGATTTTTTCTCAGTAAAGTAGATAAAGATGGATGAATCAGC
CTTGTTGGATCTTTTGGAGTGTCCGGTGTGTCTAGAGCGCCTTGATGCTTCTGCGAAGGTCTTGCCTTGC
CAGCATACGTTTTGCAAGCGATGTTTGCTGGGATCGTAGGTTCTCGAAATGAACTCAGATGTCCCGAGT
GCAGGACTCTTGTTGGCTCGGGTGTCGAGGAGCTTCCCAGTAACATCTTGCTGGTCAGACTTCTGGATGG
CATCAAACAGAGGCCTTGGAAACCTGGTCCTGGTGGGGAAGTGGGACCAACTGCACAAATGCATTAAGG
TCTCAGAGCAGCACTGTGGCTAATTGTAGCTCAAAAGATCTGCAGAGCTCCCAGGGCGGACAGCAGCCTC
GGGTGCAATCCTGGAGCCCCCCAGTGAGGGGTATACCTCAGTTACCATGTGCCAAAGCGTTATACAACTA
TGAAGGAAAAGAGCCTGGAGACCTTAAATTCAGCAAAGGCGACATCATCATTTTGCGAAGACAAGTGGAT
GAAAATTGGTACCATGGGAAGTCAATGGAATCCATGGCTTTTTCCCACCAACTTTGTGCAGATTATTA
AACCGTTACCTCAGCCCCCACCTCAGTGCAAAGCACTTTATGACTTTGAAGTGAAAGACAAGGAAGCAGA
GAAAGATTGCCTTCCATTTGCAAAGGATGATGTTCTGACTGTGATCCGAAGAGTGGATGAAAACTGGGCT
GAAGGAATGCTGGCAGACAAAATAGGAATATTTCCAATTTCATATGTTGAGTTTAACTCGGCTGCTAAGC
AGCTGATAGAATGGGATAAGCCTCCTGTGCCAGGACTTGATGCTGGAGAATGTTCGTCGGCAGCAGCCCA
GAGCAGCACTGCCCCAAAGCACTCCGACACCAAGAAGAACACCAAAAAGCGGCACTCCTTCACTTCCCTC
ACTATGGCCAACAAGTCCTCCCAGGCATCCCAGAACCGCCACTCCATGGAGATCAGCCCCCCTGTCCTCA
TCAGCTCCAGCAACCCCACTGCTGCTGCACGGATCAGCGAGCTGTCTGGGCTCTCCTGCAGTGCCCCTTC
TCAGGTTCATATAAGTACCACCGGGTTAATTGTGACCCCGCCCCCAAGCAGCCCAGTGACAACTGGCCCC
TCGTTTACTTTTCCCATCAGATGTTCCCTACCAAGCTGCCCTTGGAACTTTGAATCCTCCTCTTCCACCAC
CCCCTCTCCTGGCTGCCACTGTCCTTTGCCTCCACACCACCAGGCGCCACCGCCGCCGCTGCTGCTGCTGG
AATGGGACCGAGGCCCATGGCAGGATCCACTGACCAGATTGCACATTTACGGCCGCAGACTCGCCCCAGT
GTGTATGTTGCTATATATCCATACACTCCTCGGAAAGAGGATGAACTAGAGCTGAGAAAAGGGGAGATGT
TTTAGTGTTTGAGCGCTGCCAGGATGCCTGGTTCAAAGGGACATCCATGCATACGAGCAAGCAAGATAGGGT
TTTCCCTGCCAATTATGTGGCACCAGTCACAAGGCGGTGACAAATGCTTCCCAAGCTAAAGTCCCTATC
TCTACAGCTGCCAGACAAGTCGGGGAGTGACCATGGTCAGTCCTTCCACGCCAGGAGGGCCTGCCCAGA
AGCTCCAGGGAAATGGCGTGGCTGGGAGTCCCAGTGTTGTCCCCGCAGCTGTGGTATCAGCAGCTCACAT
CCAGACAAGTCCTCAGGCTAAGGTCTTGTTGCACATGACGGGGCAAATGACAGTCAACCAGGCCCGCAAT
GCTGTGAGGACAGTTGCAGCGCACAACCAGGAACGCCCCACGGCAGCAGTGACACCCATCCAGGTACAGA
ATGCCGGCGGCCCTCAGCCCTGCATCTGTGGGCCTGTCCCATCACTCGCTGGCCTCCCCACAACCTGCGCC
TCTGATGCCAGGCTCAGCCACGCACACTGCTGCCATCAGTATCAGTCGAGCCAGTGCCCCTCTGGCCTGT
GCAGCAGCTGCTCCACTGACTTCCCCAAGCATCACCAGTGCTTCTCTGGAGGCTGAGCCCAGTGGCCGGA
TAGTGACCGTTCTCCCTGGACTCCCCACATCTCCTGACAGTGCTTCATCAGCTTGTGGGAACAGTTCAGC
AACCAAACCAGACAAGGATAGCAAAAAAGAAAAAAAGGGTTTGTTGAAGTTGCTTTCTGGCGCCTCCACT
AAACGGAAGCCCCGCGTGTCTCCTCCAGCATCGCCCACCCTAGAAGTGGAGCTGGGCAGTGCAGAGCTTC
CTCTCCAGGGAGCGGTGGGGCCCGAACTGCCACCAGGAGGTGGCCATGGCAGGGCAGGCTCCTGCCCTGT
GGACGGGGACGGACCGGTCACGACTGCAGTGGCAGGAGCAGCCCTGGCCCAGGATGCTTTTCATAGGAAG
GCAAGTTCCCTGGACTCCGCAGTTCCCATCGCTCCACCTCCTCGCCAGGCCTGTTCCTCCCTGGGTCCTG
TCTTGAATGAGTCTAGACCTGTCGTTTGTGAAAGGCACAGGGTGGTGGTTTCCTATCCTCCTCAGAGTGA

Fig. 8-1

```
GGCAGAACTTGAACTTAAAGAAGGAGATATTGTGTTTGTTCATAAAAAACGAGAGGATGGCTGGTTCAAA
GGCACATTACAACGTAATGGGAAAACTGGCCTTTTCCCAGGAAGCTTTGTGGAAAACATATGAGGAGACT
GACACTGAAGAAGCTTAAAATCACTTCACACAACAAAGTAGCACAAAGCAGTTTAACAGAAAGAGCACAT
TTGTGGACTTCCAGATGGTCAGGAGATGAGCAAAGGATTGGTATGTGACTCTGATGCCCCAGCACAGTTA
CCCCAGCGAGCAGAGTGAAGAAGATGTTTGTGTGGGTTTTGTTAGTCTGGATTCGGATGTATAAGGTGTG
CCTTGTACTGTCTGATTTACTACACAGAGAAACTTTTTTTTTTTTTAAGATATATGACTAAAATGGACA
ATTGTTTACAAGGCTTAACTAATTTATTTGCTTTTTTAAACTTGAACTTTTCGTATAATAGATACGTTCT
TTGGATTATGATTTTAAGAAATTATTAATTTATGAAATGATAGGTAAGGAGAAGCTGGATTATCTCCTGT
TGAGAGCAAGAGATTCGTTTTGACATAGAGTGAATGCATTTTCCCCTCTCCTCCTCCCTGCTACCATTAT
ATTTTGGGGTTATGTTTTGCTTCTTTAAGATAGAAATCCCAGTTCTCTAATTTGGTTTTCTTCTTTGGGA
AACCAAACATACAAATGAATCAGTATCAATTAGGGCCTGGGGTAGAGAGACAGAAACTTGAGAGAAGAGA
AGTTAGTGATTCCCTCTCTTTCTAGTTTGGTAGGAATCACCCTGAAGACCTAGTCCTCAATTTAATTGTG
TGGGTTTTTAATTTTCCTAGAATGAAGTGACTGAAACAATGAGAAAGAATACAGCACAACCCTTGAACAA
AATGTATTTAGAAATATATTTAGTTTTATAGCAGAAGCAGCTCAATTGTTTGGTTGGAAAGTAGGGGAAA
TTGAAGTTGTAGTCACTGTCTGAGAATGGCTATGAAGCGTCATTTCACATTTTACCCCAACTGACCTGCA
TGCCCAGGACACAAGTAAAACATTTGTGAGATAGTGGTGGTAAGTGATGCACTCGTGTTAAGTCAAAGGC
TATAAGAAACACTGTGAAAAGTTCATATTCATCCATTGTGATTCTTTCCCCACGTCTTGCATGTATTACT
GGATTCCCACAGTAATATAGACTGTGCATGGTGTGTATATTTCATTGCGATTTCCTGTTAAGATGAGTTT
GTACTCAGAATTGACCAATTCAGGAGGTGTAAAAATAAACAGTGTTCTCTTCTCTACCCCAAAGCCACTA
CTGACCAAGGTCTCTTCAGTGCACTCGCTCCCTCTCTGGCTAAGGCATGCATTAGCCACTACACAAGTCA
TTAGTGAAAGTGGTCTTTTATGTCCTCCCAGCAGACAGACATCAAGGATGAGTTAACCAGGAGACTACTC
CTGTGACTGTGGAGCTCTGGAAGGCTTGGTGGGAGTGAATTTGCCCACACCTTACAATTGTGGCAGGATC
CAGAAGAGCCTGTCTTTTTATATCCATTCCTTGATGTCATTGGCCTCTCCCACCGATTTCATTACGGTGC
CACGCAGTCATGGATCTGGGTAGTCCGGAAAACAAAAGGAGGGAAGACAGCCTGGTAATGAATAAGATCC
TTACCACAGTTTTCTCATGGGAAATACATAATAAACCCTTTCATCTTTTTTTTTTCCTTTAAGAATTAA
AACTGGGAAATAGAAACATGAACTGAAAGTCTTGCAATGACAAGAGGTTTCATGGTCTTAAAAAGATAC
TTTATATGGTTGAAGATGAAATCATTCCTAAATTAACCTTTTTTTAAAAAAAAACAATGTATATTATGT
TCCTGTGTGTTGAATTTAAAAAAAAAAAATACTTTACTTGGATATTCATGTAATATATAAAGGTTTGGTG
AAATGAACTTTAGTTAGGAAAAAGCTGGCATCAGCTTTCATCTGTGTAAGTTGACACCAATGTGTCATAA
TATTCTTTATTTTGGGAAATTAGTGTATTTTATAAAAATTTTAAAAAGAAAAAAGACTACTACAGGTTAA
GATAATTTTTTTACCTGTCTTTTCTCCATATTTTAAGCTATGTGATTGAAGTACCTCTGTTCATAGTTTC
CTGGTATAAAGTTGGTTAAAATTTCATCTGTTAATAGATCATTAGGTAATATAATGTATGGGTTTTCTAT
TGGTTTTTTGCAGACAGTAGAGGGAGATTTTGTAACAAGGGCTTGTTACACAGTGATATGGTAATGATAA
AATTGCAATTTATCACTCCTTTTCATGTTAATAATTTGAGGACTGGATAAAAGGTTTCAAGATTAAAATT
TGATGTTCAAACCTTTGT
```

Fig. 8-2

DOMAIN ANALYSIS OF HUMAN POSH

| DOMAIN NAME | BEGIN | END | E-VALUE |
|---|---|---|---|
| RING | 12 | 52 | 1.06e-08 |
| SH3 | 137 | 192 | 2.76e-19 |
| SH3 | 199 | 258 | 4.84e-15 |
| LOW COMPLEXITY | 366 | 384 | - |
| LOW COMPLEXITY | 390 | 434 | - |
| SH3 | 448 | 505 | 2.40e-19 |
| LOW COMPLEXITY | 547 | 563 | - |
| LOW COMPLEXITY | 652 | 668 | - |
| LOW COMPLEXITY | 705 | 729 | - |
| SH3 | 832 | 888 | 1.47e-14 |

Fig. 9

REDUCTION IN FLUU LENGTH POSH
mRNA BY siRNA DUPLEXES

POSH AFFECTS RELEASE OF VLP FROM CELLS

Mouse POSH mRNA sequence (public gi:10946921; SEQ ID NO: 8)

```
GGGCAGCGGGCTCGGCGGGGCTGCATCTACCAGCGCTGCGGGGCCGCGAACAAAGGCGAGCAGCGGAGGC
GCGAGAGCAAAGTCTGAAATGGATGTTACATGAATCACTTTAAGGGCTGCGCACAACTATGAACGTTCTG
AAGCCGTTTTCTCACTAAAGTCACTCAAGATGGATGAGTCTGCCTTGTTGGACCTTCTGGAGTGCCCTGT
GTGTCTAGAACGCCTGGATGCTTCCGCAAAGGTCTTACCCTGCCAGCATACCTTTTGCAAACGCTGTTTG
CTGGGGATTGTGGGTTCCCGGAATGAACTCAGATGTCCCGAATGCCGGACTCTTGTTGGCTCTGGGGTCG
ACGAGCTCCCCAGTAACATCCTACTGGTCAGACTTCTGGATGGCATCAAGCAGAGGCCTTGGAAACCCGG
CCCTGGTGGGGCGGCGGGACCACCTGCACAAACACATTAAGGGCGCAGGGCAGCACTGTGGTTAATTGT
GGCTCGAAAGATCTGCAGAGCTCCCAGTGTGGACAGCAGCCTCGGGTGCAAGCCTGGAGCCCCCAGTGA
GGGGAATACCTCAGTTACCGTGTGCCAAAGCATTATATAACTACGAAGGAAAAGAGCCCGGAGACCTTAA
GTTCAGCAAAGGCGACACCATCATTCTGCGCCGACAGGTGGATGAGAATTGGTACCACGGGGAAGTCAGC
GGGGTCCACGGCTTTTTCCCCACTAACTTCGTGCAGATCATCAAACCTTTACCTCAGCCCCCGCCTCAGT
GCAAAGCACTTTACGACTTTGAAGTGAAAGACAAGGAAGCTGACAAAGATTGCCTTCCCTTCGCAAAGGA
CGACGTACTGACCGTGATCCGCAGAGTGGATGAAAACTGGGCTGAAGGAATGCTGGCAGATAAAATAGGA
ATATTTCCAATTTCATACGTGGAGTTTAACTCAGCTGCCAAGCAGCTGATAGAGTGGGATAAGCCTCCCG
TGCCAGGAGTGGACACGGCAGAATGCCCCTCAGCGACGGCGCAGAGCACCTCTGCCTCAAAGCACCCCGA
CACCAAGAAGAACACCAGGAAGCGACACTCCTTCACCTCCCTCACCATGGCCAACAAGTCTTCCCAGGGG
TCCCAGAACCGCCACTCCATGGAGATCAGCCCTCCTGTGCTCATCAGTTCCAGCAACCCCACAGCCGCAG
CCCGCATCAGCGAACTGTCCGGGCTCTCCTGCAGCGCCCCGTCTCAGGTCCATATAAGCACCACTGGGTT
AATTGTGACCCCACCCCCTAGCAGCCCGGTGACAACTGGCCCTGCGTTCACGTTCCCTTCAGATGTCCCC
TACCAAGCTGCCCTTGGAAGTATGAATCCTCCACTTCCCCCACCCCCTCTCCTGGCGGCCACCGTACTCG
CCTCCACCCCGTCAGGCGCTACTGCTGCTGTTGCTGCTGCTGCTGCCGCCGCCGCTGCTGGAATGGG
ACCCAGGCCTGTGATGGGGTCCTCTGAACAGATTGCACATTTACGGCCTCAGACTCGTCCCAGTGTATAT
GTTGCTATATATCCGTACACTCCCCGGAAGGAAGACGAACTGGAGCTGAGGAAAGGGGAGATGTTTTTGG
TGTTTGAGCGTTGCCAGGACGGCTGGTACAAAGGGACATCGATGCATACCAGCAAGATAGGCGTTTTCCC
TGGCAACTATGTGGCGCCCGTCACAAGGGCGGTGACGAATGCCTCCCAAGCTAAAGTCTCTATGTCTACT
GCGGGTCAGGCAAGTCGCGGGGTGACCATGGTCAGCCCTTCCACTGCAGGAGGACCTACACAGAAGCCCC
AAGGAAACGGCGTGGCCGGAAATCCCAGCGTCGTCCCCACGGCTGTGGTGTCAGCAGCTCATATCCAGAC
AAGTCCTCAGGCTAAGGTCCTGCTGCACATGTCTGGGCAGATGACAGTCAATCAGGCCCGCAATGCTGTG
AGGACAGTTGCAGCACATAGCCAGGAACGCCCCACAGCAGCAGTGACTCCCATCCAGGTCCAGAATGCCG
CCTGCCTTGGTCCTGCATCCGTGGGCCTGCCCCATCATTCTCTGGCCTCCCAACCTCTGCCTCCAATGGC
GGGTCCTGCTGCCCACGGTGCTGCCGTCAGCATCAGTCGAACCAATGCCCCCATGGCCTGCGCTGCAGGG
GCTTCTCTGGCCTCCCCAAATATGACCAGTGCCATGTTGGAGACAGAGCCCAGTGGTCGCACAGTGACCA
TCCTCCCTGGACTCCCCACATCTCCAGAGAGTGCTGCATCAGCGTGTGGAACAGTTCAGCTGGGAAACC
AGACAAGGACAGTAAGAAAGAAAAAAAGGGCCTACTGAAGCTGCTTTCTGGTGCCTCCACCAAACGCAAG
CCCCGAGTCTCCCCTCCAGCATCACCTACCCTGGATGTGGAGCTGGGTGCTGGGGAGGCTCCCTTGCAGG
GAGCAGTAGGTCCTGAGCTGCCGCTAGGGGCAGCCACGGCAGAGTGGGTCATGCCCCACAGATGGTGA
TGGTCCAGTGGCCGCTGGAACAGCAGCCCTAGCCCAGGATGCCTTCCACCGCAAGACAAGCTCCCTGGAC
TCCGCAGTGCCCATTGCTCCACCACCTCGCCAGGCCTGCTCCTCCCTGGGCCCAGTCATGAATGAGGCCC
GGCCTGTTGTTTGTGAAAGGCACAGGGTGGTGGTTTCCTACCCTCCTCAGAGTGAGGCCGAACTTGAACT
CAAGGAAGGAGATATTGTGTTTGTTCATAAGAAACGAGAGGACGGCTGGTTCAAAGGCACGTTACAGAGG
AATGGGAAGACTGGCCTTTTCCCAGGGAGCTTTGTGGAAAACATCTGAGAAGACGGGACACGGAGAAAGC
TTATCATCACACCACGTGTGACTAAAGAGCACAAAGCAGTTTCATAGAAAGAGCACATCTGTGGACTTCC
AGATCTTCAAGAACCGAGCAGAAGATGGGCACCTGACTCCAGAGCCCCGGCCTGGTTACCCCAGGGGCAG
AGGGAAGGAGGACACACCTGTGTGGGTTCCGTCTCTCTGGGTTCTGATGTGTAAAGTGTGCCTTGTAATG
TCTAATGGACTTTACAGATAAATGTCTTTTTTTTTAAGATGTATAACTAAAATGGACAATTGTTTACA
AGGCTTAACTAATTTATTTGCTTTTTTAAAACTTGAACTTTCTTGTAATAGCAAAT
```

Fig. 14

Mouse POSH Protein sequence (Public gi: 10946922; SEQ ID NO: 9)
MDESALLDLLECPVCLERLDASAKVLPCQHTFCKRCLLGIVGSRNELRCPECRTLVGSGVDELPSNILLV
RLLDGIKQRPWKPGPGGGGGTTCTNTLRAQGSTVVNCGSKDLQSSQCGQQPRVQAWSPPVRGIPQLPCAK
ALYNYEGKEPGDLKFSKGDTIILRRQVDENWYHGEVSGVHGFFPTNFVQIIKPLPQPPPQCKALYDFEVK
DKEADKDCLPFAKDDVLTVIRRVDENWAEGMLADKIGIFPISYVEFNSAAKQLIEWDKPPVPGVDTAECP
SATAQSTSASKHPDTKKNTRKRHSFTSLTMANKSSQGSQNRHSMEISPPVLISSSNPTAAARISELSGLS
CSAPSQVHISTTGLIVTPPPSSPVTTGPAFTFPSDVPYQAALGSMNPPLPPPPLLAATVLASTPSGATAA
VAAAAAAAAAGMGPRPVMGSSEQIAHLRPQTRPSVYVAIYPYTPRKEDELELRKGEMFLVFERCQDGWY
KGTSMHTSKIGVFPGNYVAPVTRAVTNASQAKVSMSTAGQASRGVTMVSPSTAGGPTQKPQGNGVAGNPS
VVPTAVVSAAHIQTSPQAKVLLHMSGQMTVNQARNAVRTVAAHSQERPTAAVTPIQVQNAACLGPASVGL
PHHSLASQPLPPMAGPAAHGAAVSISRTNAPMACAAGASLASPNMTSAMLETEPSGRTVTILPGLPTSPE
SAASACGNSSAGKPDKDSKKEKKGLLKLLSGASTKRKPRVSPPASPTLDVELGAGEAPLQGAVGPELPLG
GSHGRVGSCPTDGDGPVAAGTAALAQDAFHRKTSSLDSAVPIAPPPRQACSSLGPVMNEARPVVCERHRV
VVSYPPQSEAELELKEGDIVFVHKKREDGWFKGTLQRNGKTGLFPGSFVENI

Fig. 15

Drosophila melanogaster POSH mRNA sequence
(public gi:17737480; SEQ ID NO:10)

CATTTGTATCCGCTTGGCCACGAGCTTTGGCTGCACTTGGCAAACTTAATAAATTAAACATTGAATCCTG
CCTATTGCAACGATAATATAATCTGATTTAGTGCATTAAGAACGACAAGTAGCGATTATAATAGTAGATT
TTAGCATTTGAGCTAAATTTATTTCCCAACCGCGTCTTGGGATTGCGTATGCGTGAGCCAGTACCTGCAT
GTGTGTGTGTTTTGGAATGTGGCCCTGCACGAAATTCAAATAGTGACCATCCTTGAGATTTTGCATACTG
GCAAGATGGACGAGCACACGTTAAACGACCTGTTGGAGTGCTCCGTGTGTCTTGAGCGACTGGACACCAC
ATCGAAGGTGCTGCCATGCCAGCACACCTTCTGCCGCAAATGCTTGCAGGACATTGTGGCCAGTCAGCAC
AAGTTGCGATGCCCGGAGTGCCGCATCCTGGTCTCTTGCAAAATTGATGAGCTGCCTCCAAACGTCTTGC
TGATGCGAATCTTAGAAGGCATGAAACAAAATGCAGCAGCTGGCAAAGGAGAAGAAAGGGAGAGGAGAC
TGAAACACAGCCGGAAAGGGCCAAACCTCAGCCGCCAGCGGAATCAGTGGCCCCGCCTGACAACCAACTA
CTCCAGCTGCAGTCACATCAGCAATCTCATCAGCCGGCTCGTCACAAGCAACGTCGATTTCTACTCCCCC
ACGCCTATGCCCTCTTTGACTTCGCCTCCGGTGAAGCCACCGATCTAAAGTTCAAGAAAGGGGATCTGAT
ACTGATCAAGCATCGCATCGACAACAACTGGTTTGTGGGTCAAGCGAATGGTCAGGAGGGCACATTTCCC
ATCAACTACGTCAAGGTATCGGTTCCGCTGCCCATGCCGCAGTGCATTGCCATGTATGACTTTAAGATGG
GGCCCAACGACGAGGAGGGATGCCTCGAATTTAAGAAAAGCACTGTAATACAGGTAATGCGCCGAGTTGA
TCATAATTGGGCAGAAGGACGAATTGGCCAGACCATCGGAATCTTTCCAATAGCATTCGTTGAGCTGAAT
GCAGCGGCCAAAAAGCTGTTGGACAGCGGGCTACACACCCATCCATTCTGCCATCCACCGAAGCAACAGG
GGCAGCGGGCCCTTCCTCCGGTTCCAGTTATTGATCCCACGGTGGTCACGGAATCCAGTTCGGGATCCTC
CAATTCCACGCCGGGCAGCAGCAATTCAAGCTCCACATCCAGCTCGAATAACTGCAGTCCGAATCACCAA
ATCTCACTGCCGAATACCCCCCAACATGTAGTAGCTTCCGGATCGGCGTCTGTTCGTTTCCGTGACAAGG
GAGCAAAGGAGAAACGCCACTCACTAAATGCTTTGCTGGGAGGAGGAGCTCCATTAAGTCTGCTGCAGAC
CAACCGCCATTCGGCTGAAATTCTTAGCCTGCCCCATGAACTAAGCCGCTTGGAAGTTTCCAGCTCAACA
GCTCTAAAACCCACGTCAGCCCCACAGACATCGCGTGTACTTAAGACCACTGTTCAGCAGCAGATGCAAC
CGAATTTACCCTGGGGATACTTAGCCCTGTTCCCATACAAACCACGCCAAACGGATGAGCTGGAATTAAA
AAAGGGTTGTGTTTACATTGTGACCGAACGATGTGTGGACGGTTGGTTCAAGGGAAAAAACTGGTTGGAC
ATCACTGGAGTGTTCCCGGGCAACTACCTGACGCCCTGCGCGCCCGCGACCAGCAGCAGTTAATGCATC
AATGGAAATATGTTCCCCAAAATGCAGACGCCCAGATGGCACAAGTACAGCAGCATCCAGTTGCACCAGA
TGTGCGACTCAACAACATGCTGTCCATGCAACCGCCTGATTTGCCACCTCGTCAGCAGCAGGCTACCGCC
ACGACCACCAGTTGCTCTGTGTGGTCGAAACCAGTGGAGGCGCTGTTCAGCAGAAAATCGGAGCCCAAGC
CTGAAACTGCCACAGCTTCGACTACGAGCAGCAGTTCCTCTGGAGCAGTGGGACTTATGAGGAGATTAAC
TCACATGAAAACACGCTCCAAATCTCCGGGAGCGTCCTTGCAGCAAGTTCCGAAAGAAGCTATTAGCACA
AATGTGGAATTTACAACAAACCCATCAGCTAAATTGCATCCAGTACATGTAAGATCCGGCTCGTGCCCCA
GTCAGCTGCAGCACAGTCAACCGCTCAATGAAACTCCAGCAGCCAAGACAGCGGCACAACAACAGCAGTT
CCTACCCAAGCAGCTGCCTTCCGCTTCTACGAACAGCGTTTCGTACGGATCGCAACGCGTGAAAGGAAGC
AAGGAACGTCCTCACTTGATTTGCGCGAGACAATCATTAGATGCAGCTACATTTCGCAGTATGTACAACA
ATGCCGCGTCGCCGCCGCCACCTACTACTTCCGTGGCCCCAGCTGTCTACGCCGGCGGTCAGCAACAGGT
GATTCCTGGAGGTGGAGCGCAATCCCAGTTGCATGCCAATATGATTATTGCACCCAGCCATCGGAAGTCG
CACAGCCTAGATGCGAGTCATGTGCTGAGTCCAGCAGCAATATGATCACGGAGGCGGCCATTAAGGCCA
GCGCCACCACTAAGTCTCCTTACTGCACGAGGGAAAGTCGATTCCGCTGCATTGTGCCGTATCCACCAAA
CAGTGACATTGAACTAGAGCTACATTTGGGCGACATTATCTACGTCCAGCGGAAGCAGAAGAACGGCTGG
TATAAGGGCACCCATGCCCGTACCCACAAAACCGGGCTGTTCCCCGCCTCCTTTGTTAACCGGATTGTT
AGGAAAGTTATGGTTCAAACTAGAATTTATTAAGCGAAATTCCAAATTACTTGTCTAAAAGGATTCAATC
GTCGGTCTATTCGGGCTTCCAAATACGCAATCTCATATTTCTCTTTTCAAAAAGAAACCGTTTGTACT
CTTCCAATCGAATGGGCAGCTCGCCGTTGTACTTTTTTATACAATGCTTGATCAAAATAGGCTAGCCATG
TAAGACTTAGGGAACAGTTACTTAAGCCTTAGCGATTAGTTAGCTAGAGAAATAATCTAACCGATCCTTG
TGCCCTCTACAAAGTTATTTGTAATATACGATACTCAGTAATAAAAAAAAAAAAAAAAAAAAAAAAAAAA

Fig. 16

Drosophila melanogaster POSH protein sequence
(public gi:17737481; SEQ ID NO:11)
MDEHTLNDLLECSVCLERLDTTSKVLPCQHTFCRKCLQDIVASQHKLRCPECRILVSCKIDELPPNVLLM
RILEGMKQNAAAGKGEEKGEETETQPERAKPQPPAESVAPPDNQLLQLQSHQQSHQPARHKQRRFLLPHA
YALFDFASGEATDLKFKKGDLILIKHRIDNNWFVGQANGQEGTFPINYVKVSVPLPMPQCIAMYDFKMGP
NDEEGCLEFKKSTVIQVMRRVDHNWAEGRIGQTIGIFPIAFVELNAAAKKLLDSGLHTHPFCHPPKQQGQ
RALPPVPVIDPTVVTESSSGSSNSTPGSSNSSSTSSSNNCSPNHQISLPNTPQHVVASGSASVRFRDKGA
KEKRHSLNALLGGGAPLSLLQTNRHSAEILSLPHELSRLEVSSSTALKPTSAPQTSRVLKTTVQQQMQPN
LPWGYLALFPYKPRQTDELELKKGCVYIVTERCVDGWFKGKNWLDITGVFPGNYLTPLRARDQQQLMHQW
KYVPQNADAQMAQVQQHPVAPDVRLNNMLSMQPPDLPPRQQQATATTTSCSVWSKPVEALFSRKSEPKPE
TATASTTSSSSSGAVGLMRRLTHMKTRSKSPGASLQQVPKEAISTNVEFTTNPSAKLHPVHVRSGSCPSQ
LQHSQPLNETPAAKTAAQQQQFLPKQLPSASTNSVSYGSQRVKGSKERPHLICARQSLDAATFRSMYNNA
ASPPPPTTSVAPAVYAGGQQQVIPGGGAQSQLHANMIIAPSHRKSHSLDASHVLSPSSNMITEAAIKASA
TTKSPYCTRESRFRCIVPYPPNSDIELELHLGDIIYVQRKQKNGWYKGTHARTHKTGLFPASFVEPDC

Fig. 17

POSH DOMAIN ANALYSIS
hPOSH protein sequence:
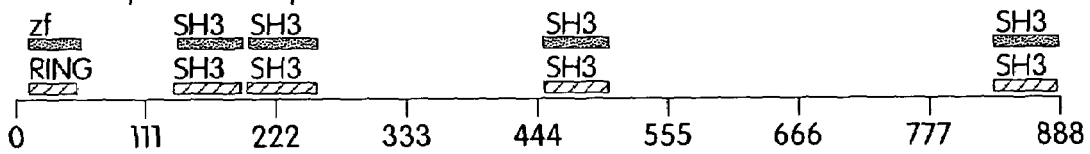
N terminus protein fragment of hPOSH (public gi:10432612):
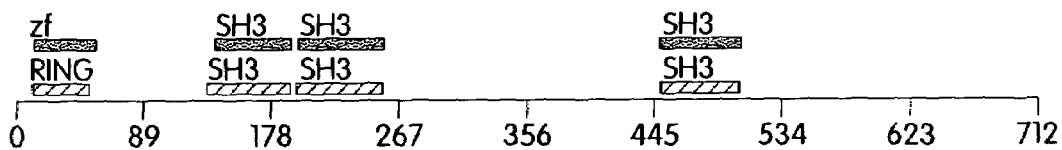
C terminus protein fragment of hPOSH (public gi:7959249):
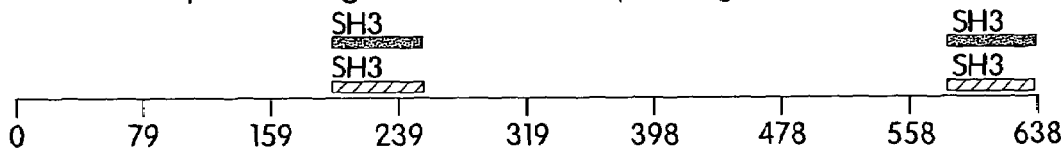
Mouse POSH Protein sequence (Public gi: 10946922):
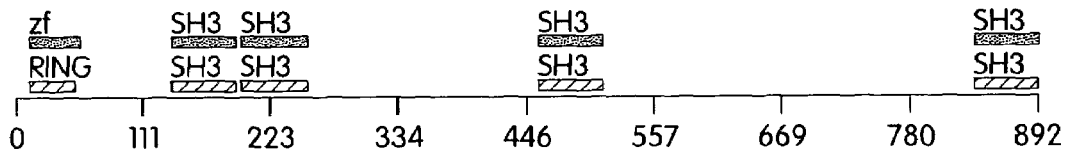
Drosophila melanogaster POSH protein sequence (public gi:17737481)
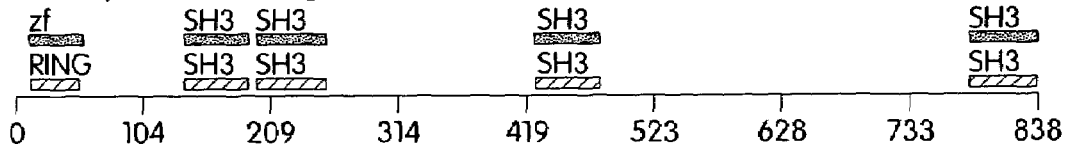
Fig. 18

POSH IS LOCALIZED AT TWO SITES ONE AT NECLEAI AND ONE AT THE GOLGI (C).
AFTER HIV TRANSFECTION RECROTMENT OF POSH TO THE GOGLI IS ENHANSED (D)

SEQUENCE LISTING

<160> NUMBER OF SEQ ID NOS: 48

<210> SEQ ID NO 1
<211> LENGTH: 2667
<212> TYPE: DNA
<213> ORGANISM: Homo sapiens

<400> SEQUENCE: 1
atggatgaat cagccttgtt ggatcttttg gagtgtccgg tgtgtctaga gcgccttgat      60
gcttctgcga aggtcttgcc ttgccagcat acgttttgca agcgatgttt gctggggatc     120

-continued

| | |
|---|---|
| gtaggttctc gaaatgaact cagatgtccc gagtgcagga ctcttgttgg ctcgggtgtc | 180 |
| gaggagcttc ccagtaacat cttgctggtc agacttctgg atggcatcaa acagaggcct | 240 |
| tggaaacctg gtcctggtgg gggaagtggg accaactgca caaatgcatt aaggtctcag | 300 |
| agcagcactg tggctaattg tagctcaaaa gatctgcaga gctcccaggg cggacagcag | 360 |
| cctcgggtgc aatcctggag ccccccagtg aggggtatac ctcagttacc atgtgccaaa | 420 |
| gcgttataca actatgaagg aaaagagcct ggagacctta aattcagcaa aggcgacatc | 480 |
| atcattttgc gaagacaagt ggatgaaaat tggtaccatg gggaagtcaa tggaatccat | 540 |
| ggcttttcc ccaccaactt tgtgcagatt attaaaccgt tacctcagcc cccacctcag | 600 |
| tgcaaagcac tttatgactt tgaagtgaaa gacaaggaag cagacaaaga ttgccttcca | 660 |
| tttgcaaagg atgatgttct gactgtgatc gaagagtgg atgaaaactg gctgaagga | 720 |
| atgctggcag acaaaatagg aatatttcca atttcatatg ttgagtttaa ctcggctgct | 780 |
| aagcagctga tagaatggga taagcctcct gtgccaggaa ttgatgctgg agaatgttcc | 840 |
| tcggcagcag cccagagcag cactgcccca aagcactccg acaccaagaa gaacaccaaa | 900 |
| aagcggcact ccttcacttc cctcactatg gccaacaagt cctcccaggc atcccagaac | 960 |
| cgccactcca tggagatcag cccccctgtc ctcatcagct ccagcaaccc cactgctgct | 1020 |
| gcacggatca gcgagctgtc tgggctctcc tgcagtgccc cttctcaggt tcatataagt | 1080 |
| accaccgggt taattgtgac cccgccccca agcagcccag tgacaactgg cccctcgttt | 1140 |
| actttcccat cagatgttcc ctaccaagct gcccttggaa ctttgaatcc tcctcttcca | 1200 |
| ccacccctc tcctggctgc cactgtcctt gcctccacac caccaggcgc caccgccgcc | 1260 |
| gctgctgctg ctggaatggg accgaggccc atggcaggat ccactgacca gattgcacat | 1320 |
| ttacggccgc agactcgccc cagtgtgtat gttgctatat atccatacac tcctcggaaa | 1380 |
| gaggatgaac tagagctgag aaaagggag atgttttttag tgtttgagcg ctgccaggat | 1440 |
| ggctggttca aagggacatc catgcatacc agcaagatag gggttttccc tggcaattat | 1500 |
| gtggcaccag tcacaaggc ggtgacaaat gcttcccaag ctaaagtccc tatgtctaca | 1560 |
| gctggccaga caagtcgggg agtgaccatg gtcagtcctt ccacggcagg agggcctgcc | 1620 |
| cagaagctcc agggaaatgg cgtggctggg agtcccagtg ttgtcccgc agctgtggta | 1680 |
| tcagcagctc acatccagac aagtcctcag gctaaggtct tgttgcacat gacggggcaa | 1740 |
| atgacagtca accaggcccg caatgctgtg aggacagttg cagcgcacaa ccaggaacgc | 1800 |
| cccacggcag cagtgacacc catccaggta cagaatgccg ccggcctcag ccctgcatct | 1860 |
| gtgggcctgt cccatcactc gctggcctcc ccacaacctg cgcctctgat gccaggctca | 1920 |
| gccacgcaca ctgctgccat cagtatcagt cgagccagtg cccctctggc ctgtgcagca | 1980 |
| gctgctccac tgacttcccc aagcatcacc agtgcttctc tggaggctga gcccagtggc | 2040 |
| cggatagtga ccgttctccc tggactcccc acatctcctg acagtgcttc atcagcttgt | 2100 |
| gggaacagtt cagcaaccaa accagacaag gatagcaaaa agaaaaaaa gggtttgttg | 2160 |
| aagttgcttt ctggcgcctc cactaaacgg aagccccgcg tgtctcctcc agcatcgccc | 2220 |
| accctagaag tggagctggg cagtgcagag cttcctctcc agggagcggt ggggcccgaa | 2280 |
| ctgccaccag gaggtggcca tgcagggca ggctcctgcc ctgtgacgg ggacggaccg | 2340 |
| gtcacgactg cagtggcagg agcagccctg gcccaggatg cttttcatag gaaggcaagt | 2400 |
| tccctggact ccgcagttcc catcgctcca cctcctcgcc aggcctgttc ctccctgggt | 2460 |
| cctgtcttga atgagtctag acctgtcgtt tgtgaaaggc acagggtggt ggtttcctat | 2520 |

```
cctcctcaga gtgaggcaga acttgaactt aaagaaggag atattgtgtt tgttcataaa    2580
aaacgagagg atggctggtt caaaggcaca ttacaacgta atgggaaaac tggccttttc    2640
ccaggaagct ttgtggaaaa catatga                                        2667
```

<210> SEQ ID NO 2
<211> LENGTH: 888
<212> TYPE: PRT
<213> ORGANISM: Homo sapiens

<400> SEQUENCE: 2

```
Met Asp Glu Ser Ala Leu Leu Asp Leu Leu Glu Cys Pro Val Cys Leu
1               5                   10                  15

Glu Arg Leu Asp Ala Ser Ala Lys Val Leu Pro Cys Gln His Thr Phe
            20                  25                  30

Cys Lys Arg Cys Leu Leu Gly Ile Val Gly Ser Arg Asn Glu Leu Arg
        35                  40                  45

Cys Pro Glu Cys Arg Thr Leu Val Gly Ser Gly Val Glu Glu Leu Pro
    50                  55                  60

Ser Asn Ile Leu Leu Val Arg Leu Leu Asp Gly Ile Lys Gln Arg Pro
65                  70                  75                  80

Trp Lys Pro Gly Pro Gly Gly Ser Gly Thr Asn Cys Thr Asn Ala
                85                  90                  95

Leu Arg Ser Gln Ser Ser Thr Val Ala Asn Cys Ser Ser Lys Asp Leu
            100                 105                 110

Gln Ser Ser Gln Gly Gly Gln Gln Pro Arg Val Gln Ser Trp Ser Pro
        115                 120                 125

Pro Val Arg Gly Ile Pro Gln Leu Pro Cys Ala Lys Ala Leu Tyr Asn
    130                 135                 140

Tyr Glu Gly Lys Glu Pro Gly Asp Leu Lys Phe Ser Lys Gly Asp Ile
145                 150                 155                 160

Ile Ile Leu Arg Arg Gln Val Asp Glu Asn Trp Tyr His Gly Glu Val
                165                 170                 175

Asn Gly Ile His Gly Phe Phe Pro Thr Asn Phe Val Gln Ile Ile Lys
            180                 185                 190

Pro Leu Pro Gln Pro Pro Pro Gln Cys Lys Ala Leu Tyr Asp Phe Glu
        195                 200                 205

Val Lys Asp Lys Glu Ala Asp Lys Asp Cys Leu Pro Phe Ala Lys Asp
    210                 215                 220

Asp Val Leu Thr Val Ile Arg Arg Val Asp Glu Asn Trp Ala Glu Gly
225                 230                 235                 240

Met Leu Ala Asp Lys Ile Gly Ile Phe Pro Ile Ser Tyr Val Glu Phe
                245                 250                 255

Asn Ser Ala Ala Lys Gln Leu Ile Glu Trp Asp Lys Pro Pro Val Pro
            260                 265                 270

Gly Val Asp Ala Gly Glu Cys Ser Ser Ala Ala Ala Gln Ser Ser Thr
        275                 280                 285

Ala Pro Lys His Ser Asp Thr Lys Lys Asn Thr Lys Lys Arg His Ser
    290                 295                 300

Phe Thr Ser Leu Thr Met Ala Asn Lys Ser Ser Gln Ala Ser Gln Asn
305                 310                 315                 320

Arg His Ser Met Glu Ile Ser Pro Pro Val Leu Ile Ser Ser Ser Asn
                325                 330                 335

Pro Thr Ala Ala Ala Arg Ile Ser Glu Leu Ser Gly Leu Ser Cys Ser
```

-continued

```
                340             345             350
Ala Pro Ser Gln Val His Ile Ser Thr Thr Gly Leu Ile Val Thr Pro
            355                 360                 365

Pro Pro Ser Ser Pro Val Thr Thr Gly Pro Ser Phe Thr Phe Pro Ser
    370                 375                 380

Asp Val Pro Tyr Gln Ala Ala Leu Gly Thr Leu Asn Pro Pro Leu Pro
385                 390                 395                 400

Pro Pro Pro Leu Leu Ala Ala Thr Val Leu Ala Ser Thr Pro Pro Gly
                405                 410                 415

Ala Thr Ala Ala Ala Ala Ala Gly Met Gly Pro Arg Pro Met Ala
            420                 425                 430

Gly Ser Thr Asp Gln Ile Ala His Leu Arg Pro Gln Thr Arg Pro Ser
            435                 440                 445

Val Tyr Val Ala Ile Tyr Pro Tyr Thr Pro Arg Lys Glu Asp Glu Leu
        450                 455                 460

Glu Leu Arg Lys Gly Glu Met Phe Leu Val Phe Glu Arg Cys Gln Asp
465                 470                 475                 480

Gly Trp Phe Lys Gly Thr Ser Met His Thr Ser Lys Ile Gly Val Phe
                485                 490                 495

Pro Gly Asn Tyr Val Ala Pro Val Thr Arg Ala Val Thr Asn Ala Ser
            500                 505                 510

Gln Ala Lys Val Pro Met Ser Thr Ala Gly Gln Thr Ser Arg Gly Val
        515                 520                 525

Thr Met Val Ser Pro Ser Thr Ala Gly Gly Pro Ala Gln Lys Leu Gln
    530                 535                 540

Gly Asn Gly Val Ala Gly Ser Pro Ser Val Val Pro Ala Ala Val Val
545                 550                 555                 560

Ser Ala Ala His Ile Gln Thr Ser Pro Gln Ala Lys Val Leu Leu His
                565                 570                 575

Met Thr Gly Gln Met Thr Val Asn Gln Ala Arg Asn Ala Val Arg Thr
            580                 585                 590

Val Ala Ala His Asn Gln Glu Arg Pro Thr Ala Ala Val Thr Pro Ile
        595                 600                 605

Gln Val Gln Asn Ala Ala Gly Leu Ser Pro Ala Ser Val Gly Leu Ser
    610                 615                 620

His His Ser Leu Ala Ser Pro Gln Pro Ala Pro Leu Met Pro Gly Ser
625                 630                 635                 640

Ala Thr His Thr Ala Ala Ile Ser Ile Ser Arg Ala Ser Ala Pro Leu
                645                 650                 655

Ala Cys Ala Ala Ala Ala Pro Leu Thr Ser Pro Ser Ile Thr Ser Ala
            660                 665                 670

Ser Leu Glu Ala Glu Pro Ser Gly Arg Ile Val Thr Val Leu Pro Gly
        675                 680                 685

Leu Pro Thr Ser Pro Asp Ser Ala Ser Ser Ala Cys Gly Asn Ser Ser
    690                 695                 700

Ala Thr Lys Pro Asp Lys Asp Ser Lys Lys Glu Lys Lys Gly Leu Leu
705                 710                 715                 720

Lys Leu Leu Ser Gly Ala Ser Thr Lys Arg Lys Pro Arg Val Ser Pro
                725                 730                 735

Pro Ala Ser Pro Thr Leu Glu Val Glu Leu Gly Ser Ala Glu Leu Pro
            740                 745                 750

Leu Gln Gly Ala Val Gly Pro Glu Leu Pro Pro Gly Gly Gly His Gly
        755                 760                 765
```

```
Arg Ala Gly Ser Cys Pro Val Asp Gly Asp Gly Pro Val Thr Thr Ala
        770             775             780

Val Ala Gly Ala Ala Leu Ala Gln Asp Ala Phe His Arg Lys Ala Ser
785             790             795                 800

Ser Leu Asp Ser Ala Val Pro Ile Ala Pro Pro Arg Gln Ala Cys
            805             810             815

Ser Ser Leu Gly Pro Val Leu Asn Glu Ser Arg Pro Val Cys Glu
            820             825             830

Arg His Arg Val Val Ser Tyr Pro Pro Gln Ser Glu Ala Glu Leu
            835             840             845

Glu Leu Lys Glu Gly Asp Ile Val Phe Val His Lys Lys Arg Glu Asp
        850             855             860

Gly Trp Phe Lys Gly Thr Leu Gln Arg Asn Gly Lys Thr Gly Leu Phe
865             870             875             880

Pro Gly Ser Phe Val Glu Asn Ile
                885
```

<210> SEQ ID NO 3
<211> LENGTH: 5128
<212> TYPE: DNA
<213> ORGANISM: Homo sapiens

<400> SEQUENCE: 3

| | | | | | |
|---|---|---|---|---|---|
| ctgagagaca | ctgcgagcgg | cgagcgcggt | ggggccgcat | ctgcatcagc | cgccgcagcc | 60 |
| gctgcgggc | cgcgaacaaa | gaggaggagc | cgaggcgcga | gagcaaagtc | tgaaatggat | 120 |
| gttacatgag | tcattttaag | ggatgcacac | aactatgaac | atttctgaag | attttttctc | 180 |
| agtaaagtag | ataagatgg | atgaatcagc | cttgttggat | cttttggagt | gtccggtgtg | 240 |
| tctagagcgc | cttgatgctt | ctgcgaaggt | cttgccttgc | cagcatacgt | tttgcaagcg | 300 |
| atgtttgctg | gggatcgtag | gttctcgaaa | tgaactcaga | tgtcccgagt | gcaggactct | 360 |
| tgttggctcg | ggtgtcgagg | agcttcccag | taacatcttg | ctggtcagac | ttctggatgg | 420 |
| catcaaacag | aggccttgga | aacctggtcc | tggtggggga | agtgggacca | actgcacaaa | 480 |
| tgcattaagg | tctcagagca | gcactgtggc | taattgtagc | tcaaaagatc | tgcagagctc | 540 |
| ccagggcgga | cagcagcctc | gggtgcaatc | ctggagcccc | ccagtgaggg | gtatacctca | 600 |
| gttaccatgt | gccaaagcgt | tatacaacta | tgaaggaaaa | gagcctggag | accttaaatt | 660 |
| cagcaaaggc | gacatcatca | tttttgcgaag | acaagtggat | gaaaattggt | accatgggga | 720 |
| agtcaatgga | atccatggct | tttcccccac | caactttgtg | cagattatta | aaccgttacc | 780 |
| tcagccccca | cctcagtgca | aagcacttta | tgactttgaa | gtgaaagaca | aggaagcaga | 840 |
| caaagattgc | cttccatttg | caaaggatga | tgttctgact | gtgatccgaa | gagtggatga | 900 |
| aaactgggct | gaaggaatgc | tggcagacaa | aataggaata | tttccaattt | catatgttga | 960 |
| gtttaactcg | gctgctaagc | agctgataga | atgggataag | cctcctgtgc | caggagttga | 1020 |
| tgctggagaa | tgttcctcgg | cagcagccca | gagcagcact | gccccaaagc | actccgacac | 1080 |
| caagaagaac | accaaaaagc | ggcactcctt | cacttccctc | actatggcca | acaagtcctc | 1140 |
| ccaggcatcc | cagaaccgcc | actccatgga | gatcagcccc | cctgtcctca | tcagctccag | 1200 |
| caaccccact | gctgctgcac | ggatcagcga | gctgtctggg | ctctcctgca | gtgcccctc | 1260 |
| tcaggttcat | ataagtacca | ccgggttaat | tgtgaccccg | cccccaagca | gcccagtgac | 1320 |
| aactggcccc | tcgtttactt | tcccatcaga | tgttccctac | caagctgccc | ttggaacttt | 1380 |

```
gaatcctcct cttccaccac cccctctcct ggctgccact gtccttgcct ccacaccacc    1440
aggcgccacc gccgccgctg ctgctgctgg aatgggaccg aggcccatgg caggatccac    1500
tgaccagatt gcacatttac ggccgcagac tcgccccagt gtgtatgttg ctatatatcc    1560
atacactcct cggaaagagg atgaactaga gctgagaaaa ggggagatgt ttttagtgtt    1620
tgagcgctgc caggatggct ggttcaaagg gacatccatg cataccagca agatagggt     1680 tttccctggc aattatgtgg caccagtcac aagggcggtg acaaatgctt cccaagctaa    1740
agtccctatg tctacagctg gccagacaag tcggggagtg accatggtca gtccttccac    1800
ggcaggaggg cctgcccaga agctccaggg aaatggcgtg gctgggagtc ccagtgttgt    1860
ccccgcagct gtggtatcag cagctcacat ccagacaagt cctcaggcta aggtcttgtt    1920
gcacatgacg gggcaaatga cagtcaacca ggcccgcaat gctgtgagga cagttgcagc    1980
gcacaaccag gaacgcccca cggcagcagt gacacccatc caggtacaga atgccgccgg    2040
cctcagccct gcatctgtgg gcctgtccca tcactcgctg gcctcccac aacctgcgcc     2100 tctgatgcca ggctcagcca cgcacactgc tgccatcagt atcagtcgag ccagtgcccc    2160
tctggcctgt gcagcagctg ctccactgac ttccccaagc atcaccagtg cttctctgga    2220
ggctgagccc agtggccgga tagtgaccgt tctccctgga ctccccacat tcctgacag     2280 tgcttcatca gcttgtggga acagttcagc aaccaaacca gacaaggata gcaaaaaga    2340 aaaaagggt ttgttgaagt tgctttctgg cgcctccact aaacggaagc ccgcgtgtc      2400 tcctccagca tcgcccaccc tagaagtgga gctgggcagt gcagagcttc ctctccaggg    2460
agcggtgggg cccgaactgc caccaggagg tggccatggc agggcaggct cctgccctgt    2520
ggacggggac ggaccggtca cgactgcagt ggcaggagca gccctggccc aggatgcttt    2580
tcataggaag gcaagttccc tggactccgc agttcccatc gctccacctc ctcgccaggc    2640
ctgttcctcc ctgggtcctg tcttgaatga gtctagacct gtcgtttgtg aaaggcacag    2700
ggtggtggtt tcctatcctc ctcagagtga ggcagaactt gaacttaaag aaggagatat    2760
tgtgtttgtt cataaaaaac gagaggatgg ctggttcaaa ggcacattac aacgtaatgg    2820
gaaaactggc cttttcccag gaagctttgt ggaaaacata tgaggagact gacactgaag    2880
aagcttaaaa tcacttcaca caacaaagta gcacaaagca gtttaacaga aagagcacat    2940
ttgtggactt ccagatggtc aggagatgag caaaggattg gtatgtgact ctgatgcccc    3000
agcacagtta ccccagcgag cagagtgaag aagatgtttg tgtgggtttt gttagtctgg    3060
attcggatgt ataaggtgtg ccttgtactg tctgatttac tacacagaga aacttttttt    3120 ttttttaag atatatgact aaaatggaca attgtttaca aggcttaact aatttatttg     3180 ctttttaaa cttgaacttt tcgtataata gatacgttct ttggattatg attttaagaa     3240
attattaatt tatgaaatga taggtaagga gaagctggat tatctcctgt tgagagcaag    3300
agattcgttt tgacatagag tgaatgcatt ttcccctctc ctcctccctg ctaccattat    3360
attttggggt tatgttttgc ttctttaaga tagaaatccc agttctctaa tttggttttc    3420
ttctttggga aaccaaacat acaaatgaat cagtatcaat tagggcctgg ggtagagaga    3480
cagaaacttg agagaagaga agttagtgat tccctctctt tctagtttgg taggaatcac    3540
cctgaagacc tagtcctcaa tttaattgtg tgggttttta attttcctag aatgaagtga    3600
ctgaaacaat gagaaagaat acagcacaac ccttgaacaa aatgtattta gaaatatatt    3660
tagttttata gcagaagcag ctcaattgtt tggttggaaa gtaggggaaa ttgaagttgt    3720
agtcactgtc tgagaatggc tatgaagcgt catttcacat tttaccccaa ctgacctgca    3780
```

-continued

```
tgcccaggac acaagtaaaa catttgtgag atagtggtgg taagtgatgc actcgtgtta    3840
agtcaaaggc tataagaaac actgtgaaaa gttcatattc atccattgtg attctttccc    3900
cacgtcttgc atgtattact ggattcccac agtaatatag actgtgcatg gtgtgtatat    3960
ttcattgcga tttcctgtta agatgagttt gtactcagaa ttgaccaatt caggaggtgt    4020
aaaaataaac agtgttctct tctctacccc aaagccacta ctgaccaagg tctcttcagt    4080
gcactcgctc cctctctggc taaggcatgc attagccact acacaagtca ttagtgaaag    4140
tggtctttta tgtcctccca gcagacagac atcaaggatg agttaaccag agactactc    4200 ctgtgactgt ggagctctgg aaggcttggt gggagtgaat ttgcccacac cttacaattg    4260
tggcaggatc cagaagagcc tgtctttta tatccattcc ttgatgtcat tggcctctcc    4320
caccgatttc attacggtgc cacgcagtca tggatctggg tagtccggaa aacaaaagga    4380
gggaagacag cctggtaatg aataagatcc ttaccacagt tttctcatgg gaaatacata    4440
ataaaccctt tcatcttttt ttttttcctt taagaattaa aactgggaaa tagaaacatg    4500
aactgaaaag tcttgcaatg acaagaggtt tcatggtctt aaaaagatac tttatatggt    4560
tgaagatgaa atcattccta aattaacctt tttttaaaa aaaacaatg tatattatgt    4620 tcctgtgtgt tgaatttaaa aaaaaaaat actttacttg gatattcatg taatatataa    4680
aggtttggtg aaatgaactt tagttaggaa aaagctggca tcagctttca tctgtgtaag    4740
ttgacaccaa tgtgtcataa tattctttat tttgggaaat tagtgtattt tataaaaatt    4800
ttaaaaagaa aaaagactac tacaggttaa gataatttt ttacctgtct tttctccata    4860
ttttaagcta tgtgattgaa gtacctctgt tcatagtttc ctggtataaa gttggttaaa    4920
atttcatctg ttaatagatc attaggtaat ataatgtatg ggttttctat tggttttttg    4980
cagacagtag agggagattt tgtaacaagg gcttgttaca cagtgatatg gtaatgataa    5040
aattgcaatt tatcactcct tttcatgtta ataatttgag gactggataa aaggtttcaa    5100
gattaaaatt tgatgttcaa acctttgt                                       5128
```

<210> SEQ ID NO 4
<211> LENGTH: 2331
<212> TYPE: DNA
<213> ORGANISM: Homo sapiens

<400> SEQUENCE: 4

```
ctgagagaca ctgcgagcgg cgagcgcggt ggggccgcat ctgcatcagc cgccgcagcc     60 gctgcgggc cgcgaacaaa gaggaggagc cgaggcgcga gagcaaagtc tgaaatggat    120
gttacatgag tcatttaag gatgcacaca actatgaaca tttctgaaga ttttttctca    180
gtaaagtaga taaagatgga tgaatcagcc ttgttggatc ttttggagtg tccggtgtgt    240
ctagagcgcc ttgatgcttc tgcgaaggtc ttgccttgcc agcatacgtt ttgcaagcga    300
tgtttgctgg ggatcgtagg ttctcgaaat gaactcagat gtcccgagtg caggactctt    360
gttggctcgg gtgtcgagga gcttcccagt aacatcttgc tggtcagact tctggatggc    420
atcaaacaga ggccttggaa acctggtcct ggtggggaa gtgggaccaa ctgcacaaat    480
gcattaaggt ctcagagcag cactgtggct aattgtagct caaaagatct gcagagctcc    540
cagggcggac agcagcctcg ggtgcaatcc tggagccccc cagtgagggg tatacctcag    600
ttaccatgtg ccaaagcgtt atacaactat gaaggaaaag agcctggaga ccttaaattc    660
agcaaaggcg acatcatcat tttgcgaaga caagtggatg aaaattggta ccatgggga    720
```

-continued

```
gtcaatggaa tccatggctt tttccccacc aactttgtgc agattattaa accgttacct    780
cagcccccac ctcagtgcaa agcactttat gactttgaag tgaaagacaa ggaagcagac    840
aaagattgcc ttccatttgc aaaggatgat gttctgactg tgatccgaag agtggatgaa    900
aactgggctg aaggaatgct ggcagacaaa ataggaatat ttccaatttc atatgttgag    960
tttaactcgg ctgctaagca gctgatagaa tgggataagc ctcctgtgcc aggagttgat   1020
gctggagaat gttcctcggc agcagcccag agcagcactg ccccaaagca ctccgacacc   1080
aagaagaaca ccaaaaagcg gcactccttc acttccctca ctatggccaa caagtcctcc   1140
caggcatccc agaaccgcca ctccatggag atcagccccc ctgtcctcat cagctccagc   1200
aaccccactg ctgctgcacg gatcagcgag ctgtctgggc tctcctgcag tgcccttct    1260
caggttcata taagtaccac cgggttaatt gtgaccccgc ccccaagcag cccagtgaca   1320
actggcccct cgtttacttt cccatcagat gttccctacc aagctgccct tggaactttg   1380
aatcctcctc ttccaccacc ccctctcctg gctgccactg tccttgcctc cacaccacca   1440
ggcgccaccg ccgccgctgc tgctgctgga atgggaccga ggcccatggc aggatccact   1500
gaccagattg cacatttacg gccgcagact cgccccagtg tgtatgttgc tatatatcca   1560
tacactcctc ggaaagagga tgaactagag ctgagaaaag gggagatgtt tttagtgttt   1620
gagcgctgcc aggatggctg gttcaaaggg acatccatgc ataccagcaa gataggggtt   1680
ttccctggca attatgtggc accagtcaca agggcggtga caaatgcttc ccaagctaaa   1740
gtccctatgt ctacagctgg ccagacaagt cggggagtga ccatggtcag tccttccacg   1800
gcaggagggc ctgcccagaa gctccaggga atggcgtgg ctgggagtcc cagtgttgtc    1860
cccgcagctg tggtatcagc agctcacatc cagacaagtc ctcaggctaa ggtcttgttg   1920
cacatgacgg ggcaaatgac agtcaaccag gcccgcaatg ctgtgaggac agttgcagcg   1980
cacaaccagg aacgccccac ggcagcagtg acacccatcc aggtacagaa tgccgccggc   2040
ctcagccctg catctgtggg cctgtcccat cactcgctgg cctccccaca acctgcgcct   2100
ctgatgccag gctcagccac gcacactgct gccatcagta tcagtcgagc cagtgccct    2160
ctggcctgtg cagcagctgc tccactgact tccccaagca tcaccagtgc ttctctggag   2220
gctgagccca gtggccggat agtgaccgtt ctccctggac tccccacatc tcctgacagt   2280
gcttcatcag cttgtgggaa cagttcagca accaaaccag acaaggatag c            2331
```

<210> SEQ ID NO 5
<211> LENGTH: 712
<212> TYPE: PRT
<213> ORGANISM: Homo sapiens

<400> SEQUENCE: 5

```
Met Asp Glu Ser Ala Leu Leu Asp Leu Leu Glu Cys Pro Val Cys Leu
1               5                   10                  15

Glu Arg Leu Asp Ala Ser Ala Lys Val Leu Pro Cys Gln His Thr Phe
            20                  25                  30

Cys Lys Arg Cys Leu Leu Gly Ile Val Gly Ser Arg Asn Glu Leu Arg
        35                  40                  45

Cys Pro Glu Cys Arg Thr Leu Val Gly Ser Gly Val Glu Glu Leu Pro
    50                  55                  60

Ser Asn Ile Leu Leu Val Arg Leu Leu Asp Gly Ile Lys Gln Arg Pro
65                  70                  75                  80

Trp Lys Pro Gly Pro Gly Gly Gly Ser Gly Thr Asn Cys Thr Asn Ala
                85                  90                  95
```

```
Leu Arg Ser Gln Ser Ser Thr Val Ala Asn Cys Ser Ser Lys Asp Leu
            100                 105                 110

Gln Ser Ser Gln Gly Gly Gln Gln Pro Arg Val Gln Ser Trp Ser Pro
        115                 120                 125

Pro Val Arg Gly Ile Pro Gln Leu Pro Cys Ala Lys Ala Leu Tyr Asn
    130                 135                 140

Tyr Glu Gly Lys Glu Pro Gly Asp Leu Lys Phe Ser Lys Gly Asp Ile
145                 150                 155                 160

Ile Ile Leu Arg Arg Gln Val Asp Glu Asn Trp Tyr His Gly Glu Val
                165                 170                 175

Asn Gly Ile His Gly Phe Phe Pro Thr Asn Phe Val Gln Ile Ile Lys
            180                 185                 190

Pro Leu Pro Gln Pro Pro Pro Gln Cys Lys Ala Leu Tyr Asp Phe Glu
        195                 200                 205

Val Lys Asp Lys Glu Ala Asp Lys Asp Cys Leu Pro Phe Ala Lys Asp
    210                 215                 220

Asp Val Leu Thr Val Ile Arg Arg Val Asp Glu Asn Trp Ala Glu Gly
225                 230                 235                 240

Met Leu Ala Asp Lys Ile Gly Ile Phe Pro Ile Ser Tyr Val Glu Phe
                245                 250                 255

Asn Ser Ala Ala Lys Gln Leu Ile Glu Trp Asp Lys Pro Pro Val Pro
            260                 265                 270

Gly Val Asp Ala Gly Glu Cys Ser Ser Ala Ala Ala Gln Ser Ser Thr
        275                 280                 285

Ala Pro Lys His Ser Asp Thr Lys Asn Thr Lys Lys Arg His Ser
    290                 295                 300

Phe Thr Ser Leu Thr Met Ala Asn Lys Ser Ser Gln Ala Ser Gln Asn
305                 310                 315                 320

Arg His Ser Met Glu Ile Ser Pro Pro Val Leu Ile Ser Ser Ser Asn
                325                 330                 335

Pro Thr Ala Ala Ala Arg Ile Ser Glu Leu Ser Gly Leu Ser Cys Ser
            340                 345                 350

Ala Pro Ser Gln Val His Ile Ser Thr Thr Gly Leu Ile Val Thr Pro
        355                 360                 365

Pro Pro Ser Ser Pro Val Thr Thr Gly Pro Ser Phe Thr Phe Pro Ser
    370                 375                 380

Asp Val Pro Tyr Gln Ala Ala Leu Gly Thr Leu Asn Pro Pro Leu Pro
385                 390                 395                 400

Pro Pro Pro Leu Leu Ala Ala Thr Val Leu Ala Ser Thr Pro Pro Gly
                405                 410                 415

Ala Thr Ala Ala Ala Ala Ala Gly Met Gly Pro Arg Pro Met Ala
            420                 425                 430

Gly Ser Thr Asp Gln Ile Ala His Leu Arg Pro Gln Thr Arg Pro Ser
        435                 440                 445

Val Tyr Val Ala Ile Tyr Pro Tyr Thr Pro Arg Lys Glu Asp Glu Leu
    450                 455                 460

Glu Leu Arg Lys Gly Glu Met Phe Leu Val Phe Glu Arg Cys Gln Asp
465                 470                 475                 480

Gly Trp Phe Lys Gly Thr Ser Met His Thr Ser Lys Ile Gly Val Phe
                485                 490                 495

Pro Gly Asn Tyr Val Ala Pro Val Thr Arg Ala Val Thr Asn Ala Ser
            500                 505                 510
```

```
Gln Ala Lys Val Pro Met Ser Thr Ala Gly Gln Thr Ser Arg Gly Val
            515                 520                 525

Thr Met Val Ser Pro Ser Thr Ala Gly Gly Pro Ala Gln Lys Leu Gln
        530                 535                 540

Gly Asn Gly Val Ala Gly Ser Pro Ser Val Val Pro Ala Ala Val Val
545                 550                 555                 560

Ser Ala Ala His Ile Gln Thr Ser Pro Gln Ala Lys Val Leu Leu His
                565                 570                 575

Met Thr Gly Gln Met Thr Val Asn Gln Ala Arg Asn Ala Val Arg Thr
            580                 585                 590

Val Ala Ala His Asn Gln Glu Arg Pro Thr Ala Ala Val Thr Pro Ile
        595                 600                 605

Gln Val Gln Asn Ala Ala Gly Leu Ser Pro Ala Ser Val Gly Leu Ser
    610                 615                 620

His His Ser Leu Ala Ser Pro Gln Pro Ala Pro Leu Met Pro Gly Ser
625                 630                 635                 640

Ala Thr His Thr Ala Ala Ile Ser Ile Ser Arg Ala Ser Ala Pro Leu
                645                 650                 655

Ala Cys Ala Ala Ala Ala Pro Leu Thr Ser Pro Ser Ile Thr Ser Ala
            660                 665                 670

Ser Leu Glu Ala Glu Pro Ser Gly Arg Ile Val Thr Val Leu Pro Gly
        675                 680                 685

Leu Pro Thr Ser Pro Asp Ser Ala Ser Ser Ala Cys Gly Asn Ser Ser
    690                 695                 700

Ala Thr Lys Pro Asp Lys Asp Ser
705                 710

<210> SEQ ID NO 6
<211> LENGTH: 4182
<212> TYPE: DNA
<213> ORGANISM: Homo sapiens

<400> SEQUENCE: 6
atttcatatg ttgagtttaa ctcggctgct aagcagctga tagaatggga taagcctcct      60
gtgccaggag ttgatgctgg agaatgttcc tcggcagcag cccagagcag cactgcccca     120
aagcactccg acaccaagaa gaacaccaaa aagcggcact ccttcacttc cctcactatg     180
gccaacaagt cctcccaggc atcccagaac cgccactcca tggagatcag ccccctgtc      240 ctcatcagct ccagcaaccc cactgctgct gcacggatca gcgagctgtc tgggctctcc     300
tgcagtgccc cttctcaggt tcatataagt accaccgggt taattgtgac cccgccccca     360
agcagcccag tgacaactgg cccctcgttt actttcccat cagatgttcc ctaccaagct     420
gcccttggaa ctttgaatcc tcctcttcca ccacccctc tcctggctgc cactgtcctt      480
gcctccacac caccaggcgc caccgccgct gctgctgctg ctggaatggg accgaggccc     540
atggcaggat ccactgacca gattgcacat ttacggccgc agactcgccc cagtgtgtat     600
gttgctatat atccatacac tcctcggaaa gaggatgaac tagagctgag aaaaggggag     660
atgtttttag tgtttgagcg ctgccaggat ggctggttca agggacatc catgcatacc      720 agcaagatag gggttttccc tggcaattat gtggcaccag tcacaaggc ggtgacaaat      780 gcttcccaag ctaaagtccc tatgtctaca gctggccaga caagtcgggg agtgaccatg     840
gtcagtcctt ccacggcagg agggcctgcc cagaagctcc agggaaatgg cgtggctggg     900
agtcccagtg ttgtccccgc agctgtggta tcagcagctc acatccagac aagtcctcag     960
```

```
gctaaggtct tgttgcacat gacggggcaa atgacagtca accaggcccg caatgctgtg    1020
aggacagttg cagcgcacaa ccaggaacgc cccacggcag cagtgacacc catccaggta    1080
cagaatgccg ccggcctcag ccctgcatct gtgggcctgt cccatcactc gctggcctcc    1140
ccacaacctg cgcctctgat gccaggctca gccacgcaca ctgctgccat cagtatcagt    1200
cgagccagtg cccctctggc ctgtgcagca gctgctccac tgacttcccc aagcatcacc    1260
agtgcttctc tggaggctga gcccagtggc cggatagtga ccgttctccc tggactcccc    1320
acatctcctg acagtgcttc atcagcttgt gggaacagtt cagcaaccaa accagacaag    1380
gatagcaaaa aagaaaaaaa gggtttgttg aagttgcttt ctggcgcctc cactaaacgg    1440
aagccccgcg tgtctcctcc agcatcgccc accctagaag tggagctggg cagtgcagag    1500
cttcctctcc agggagcggt ggggcccgaa ctgccaccag gaggtggcca tggcagggca    1560
ggctcctgcc ctgtggacgg ggacggaccg gtcacgactg cagtggcagg agcagccctg    1620
gcccaggatg cttttcatag gaaggcaagt tccctggact ccgcagttcc catcgctcca    1680
cctcctcgcc aggcctgttc ctccctgggt cctgtcttga atgagtctag acctgtcgtt    1740
tgtgaaaggc acagggtggt ggtttcctat cctcctcaga gtgaggcaga acttgaactt    1800
aaagaaggag atattgtgtt tgttcataaa aaacgagagg atggctggtt caaaggcaca    1860
ttacaacgta atgggaaaac tggccttttc ccaggaagct ttgtgaaaaa catatgagga    1920
gactgacact gaagaagctt aaaatcactt cacacaacaa agtagcacaa agcagtttaa    1980
cagaaagagc acatttgtgg acttccagat ggtcaggaga tgagcaaagg attggtatgt    2040
gactctgatg ccccagcaca gttaccccag cgagcagagt gaagaagatg tttgtgtggg    2100
ttttgttagt ctggattcgg atgtataagg tgtgccttgt actgtctgat ttactacaca    2160
gagaaacttt ttttttttt taagatatat gactaaaatg gacaattgtt tacaaggctt    2220
aactaattta tttgcttttt taaacttgaa cttttcgtat aatagatacg ttctttggat    2280
tatgatttta agaaattatt aatttatgaa atgataggta aggagaagct ggattatctc    2340
ctgttgagag caagagattc gttttgcat agagtgaatg catttttccc tctcctcctc    2400
cctgctacca ttatattttg gggttatgtt ttgcttcttt aagatagaaa tcccagttct    2460
ctaatttggt tttcttcttt gggaaaccaa acatacaaat gaatcagtat caattagggc    2520
ctggggtaga gagacagaaa cttgagagaa gagaagttag tgattccctc tctttctagt    2580
ttggtaggaa tcaccctgaa gacctagtcc tcaatttaat tgtgtgggtt tttaattttc    2640
ctagaatgaa gtgactgaaa caatgagaaa gaatacagca caaccctga acaaaatgta    2700 tttagaaata tatttagttt tatagcagaa gcagctcaat tgtttggttg gaaagtaggg    2760
gaaattgaag ttgtagtcac tgtctgagaa tggctatgaa gcgtcatttc acattttacc    2820
ccaactgacc tgcatgccca ggacacaagt aaaacatttg tgagatagtg gtggtaagtg    2880
atgcactcgt gttaagtcaa aggctataag aaacactgtg aaaagttcat attcatccat    2940
tgtgattctt tccccacgtc ttgcatgtat tactggattc ccacagtaat atagactgtg    3000
catggtgtgt atatttcatt gcgatttcct gttaagatga gtttgtactc agaattgacc    3060
aattcaggag gtgtaaaaat aaacagtgtt ctcttctcta ccccaaagcc actactgacc    3120
aagtctcttt cagtgcactc gctccctctc tggctaaggc atgcattagc cactacacaa    3180
gtcattagtg aaagtggtct tttatgtcct cccagcagac agacatcaag gatgagttaa    3240
ccaggagact actcctgtga ctgtggagct ctggaaggct tggtgggagt gaatttgccc    3300
acaccttaca attgtggcag gatccagaag agcctgtctt tttatatcca ttccttgatg    3360
```

-continued

```
tcattggcct ctcccaccga tttcattacg gtgccacgca gtcatggatc tgggtagtcc    3420
ggaaaacaaa aggagggaag acagcctggt aatgaataag atccttacca cagttttctc    3480
atgggaaata cataataaac cctttcatct ttttttttt cctttaagaa ttaaaactgg     3540
gaaatagaaa catgaactga aaagtcttgc aatgacaaga ggtttcatgg tcttaaaaag    3600
atactttata tggttgaaga tgaaatcatt cctaaattaa cctttttttt aaaaaaaaac    3660
aatgtatatt atgttcctgt gtgttgaatt taaaaaaaaa aaatacttta cttggatatt    3720
catgtaatat ataaaggttt ggtgaaatga actttagtta ggaaaaagct ggcatcagct    3780
ttcatctgtg taagttgaca ccaatgtgtc ataatattct ttattttggg aaattagtgt    3840
attttataaa aattttaaaa agaaaaaaga ctactacagg ttaagataat tttttttacct   3900 gtctttctc catattttaa gctatgtgat tgaagtacct ctgttcatag tttcctggta     3960
taaagttggt taaaatttca tctgttaata gatcattagg taatataatg tatgggtttt    4020
ctattggttt tttgcagaca gtagagggag attttgtaac aagggcttgt tacacagtga    4080
tatggtaatg ataaaattgc aatttatcac tccttttcat gttaataatt tgaggactgg    4140
ataaaaggtt tcaagattaa aatttgatgt tcaaaccttt gt                       4182
```

<210> SEQ ID NO 7
<211> LENGTH: 638
<212> TYPE: PRT
<213> ORGANISM: Homo sapiens

<400> SEQUENCE: 7

```
Ile Ser Tyr Val Glu Phe Asn Ser Ala Ala Lys Gln Leu Ile Glu Trp
1               5                   10                  15

Asp Lys Pro Pro Val Pro Gly Val Asp Ala Gly Glu Cys Ser Ser Ala
            20                  25                  30

Ala Ala Gln Ser Ser Thr Ala Pro Lys His Ser Asp Thr Lys Lys Asn
        35                  40                  45

Thr Lys Lys Arg His Ser Phe Thr Ser Leu Thr Met Ala Asn Lys Ser
    50                  55                  60

Ser Gln Ala Ser Gln Asn Arg His Ser Met Glu Ile Ser Pro Pro Val
65                  70                  75                  80

Leu Ile Ser Ser Ser Asn Pro Thr Ala Ala Ala Arg Ile Ser Glu Leu
                85                  90                  95

Ser Gly Leu Ser Cys Ser Ala Pro Ser Gln Val His Ile Ser Thr Thr
            100                 105                 110

Gly Leu Ile Val Thr Pro Pro Ser Ser Pro Val Thr Thr Gly Pro
        115                 120                 125

Ser Phe Thr Phe Pro Ser Asp Val Pro Tyr Gln Ala Ala Leu Gly Thr
    130                 135                 140

Leu Asn Pro Pro Leu Pro Pro Pro Leu Leu Ala Ala Thr Val Leu
145                 150                 155                 160

Ala Ser Thr Pro Pro Gly Ala Thr Ala Ala Ala Ala Gly Met
                165                 170                 175

Gly Pro Arg Pro Met Ala Gly Ser Thr Asp Gln Ile Ala His Leu Arg
            180                 185                 190

Pro Gln Thr Arg Pro Ser Val Tyr Val Ala Ile Tyr Pro Tyr Thr Pro
        195                 200                 205

Arg Lys Glu Asp Glu Leu Glu Leu Arg Lys Gly Glu Met Phe Leu Val
    210                 215                 220
```

-continued

```
Phe Glu Arg Cys Gln Asp Gly Trp Phe Lys Gly Thr Ser Met His Thr
225                 230                 235                 240

Ser Lys Ile Gly Val Phe Pro Gly Asn Tyr Val Ala Pro Val Thr Arg
                245                 250                 255

Ala Val Thr Asn Ala Ser Gln Ala Lys Val Pro Met Ser Thr Ala Gly
            260                 265                 270

Gln Thr Ser Arg Gly Val Thr Met Val Ser Pro Ser Thr Ala Gly Gly
        275                 280                 285

Pro Ala Gln Lys Leu Gln Gly Asn Gly Val Ala Gly Ser Pro Ser Val
    290                 295                 300

Val Pro Ala Ala Val Val Ser Ala Ala His Ile Gln Thr Ser Pro Gln
305                 310                 315                 320

Ala Lys Val Leu Leu His Met Thr Gly Gln Met Thr Val Asn Gln Ala
                325                 330                 335

Arg Asn Ala Val Arg Thr Val Ala Ala His Asn Gln Glu Arg Pro Thr
            340                 345                 350

Ala Ala Val Thr Pro Ile Gln Val Gln Asn Ala Ala Gly Leu Ser Pro
        355                 360                 365

Ala Ser Val Gly Leu Ser His His Ser Leu Ala Ser Pro Gln Pro Ala
    370                 375                 380

Pro Leu Met Pro Gly Ser Ala Thr His Thr Ala Ala Ile Ser Ile Ser
385                 390                 395                 400

Arg Ala Ser Ala Pro Leu Ala Cys Ala Ala Ala Pro Leu Thr Ser
                405                 410                 415

Pro Ser Ile Thr Ser Ala Ser Leu Glu Ala Glu Pro Ser Gly Arg Ile
            420                 425                 430

Val Thr Val Leu Pro Gly Leu Pro Thr Ser Pro Asp Ser Ala Ser Ser
        435                 440                 445

Ala Cys Gly Asn Ser Ser Ala Thr Lys Pro Asp Lys Asp Ser Lys Lys
    450                 455                 460

Glu Lys Lys Gly Leu Leu Lys Leu Leu Ser Gly Ala Ser Thr Lys Arg
465                 470                 475                 480

Lys Pro Arg Val Ser Pro Pro Ala Ser Pro Thr Leu Glu Val Glu Leu
                485                 490                 495

Gly Ser Ala Glu Leu Pro Leu Gln Gly Ala Val Gly Pro Glu Leu Pro
            500                 505                 510

Pro Gly Gly Gly His Gly Arg Ala Gly Ser Cys Pro Val Asp Gly Asp
        515                 520                 525

Gly Pro Val Thr Thr Ala Val Ala Gly Ala Ala Leu Ala Gln Asp Ala
    530                 535                 540

Phe His Arg Lys Ala Ser Ser Leu Asp Ser Ala Val Pro Ile Ala Pro
545                 550                 555                 560

Pro Pro Arg Gln Ala Cys Ser Ser Leu Gly Pro Val Leu Asn Glu Ser
                565                 570                 575

Arg Pro Val Val Cys Glu Arg His Arg Val Val Ser Tyr Pro Pro
            580                 585                 590

Gln Ser Glu Ala Glu Leu Glu Leu Lys Glu Gly Asp Ile Val Phe Val
        595                 600                 605

His Lys Lys Arg Glu Asp Gly Trp Phe Lys Gly Thr Leu Gln Arg Asn
    610                 615                 620

Gly Lys Thr Gly Leu Phe Pro Gly Ser Phe Val Glu Asn Ile
625                 630                 635
```

<210> SEQ ID NO 8
<211> LENGTH: 3206
<212> TYPE: DNA
<213> ORGANISM: Mus musculus

<400> SEQUENCE: 8

| | | | | | | |
|---|---|---|---|---|---|---|
| gggcagcggg | ctcggcgggg | ctgcatctac | cagcgctgcg | gggccgcgaa | caaaggcgag | 60 |
| cagcggaggc | gcgagagcaa | agtctgaaat | ggatgttaca | tgaatcactt | taagggctgc | 120 |
| gcacaactat | gaacgttctg | aagccgtttt | ctcactaaag | tcactcaaga | tggatgagtc | 180 |
| tgccttgttg | gaccttctgg | agtgcccgt | gtgtctagaa | cgcctggatg | cttccgcaaa | 240 |
| ggtcttaccc | tgccagcata | ccttttgcaa | acgctgtttg | ctggggattg | tgggttcccg | 300 |
| gaatgaactc | agatgtcccg | aatgccggac | tcttgttggc | tctggggtcg | acgagctccc | 360 |
| cagtaacatc | ctactggtca | gacttctgga | tggcatcaag | cagaggcctt | ggaaacccgg | 420 |
| ccctggtggg | ggcggcggga | ccacctgcac | aaacacatta | agggcgcagg | gcagcactgt | 480 |
| ggttaattgt | ggctcgaaag | atctgcagag | ctcccagtgt | ggacagcagc | ctcgggtgca | 540 |
| agcctggagc | cccccagtga | ggggaatacc | tcagttaccg | tgtgccaaag | cattatataa | 600 |
| ctacgaagga | aaagagcccg | gagaccttaa | gttcagcaaa | ggcgacacca | tcattctgcg | 660 |
| ccgacaggtg | gatgagaatt | ggtaccacgg | ggaagtcagc | ggggtccacg | gcttttttccc | 720 |
| cactaacttc | gtgcagatca | tcaaacccttt | acctcagccc | ccgcctcagt | gcaaagcact | 780 |
| ttacgacttt | gaagtgaaag | acaaggaagc | tgacaaagat | tgccttccct | tcgcaaagga | 840 |
| cgacgtactg | accgtgatcc | gcagagtgga | tgaaaactgg | gctgaaggaa | tgctggcaga | 900 |
| taaaatagga | atatttccaa | tttcatacgt | ggagtttaac | tcagctgcca | agcagctgat | 960 |
| agagtgggat | aagcctcccg | tgccaggagt | ggacacggca | gaatgcccct | cagcgacggc | 1020 |
| gcagagcacc | tctgcctcaa | agcaccccga | caccaagaag | aacaccagga | agcgacactc | 1080 |
| cttcacctcc | ctcaccatgg | ccaacaagtc | ttcccagggg | tcccgaaacc | gccactccat | 1140 |
| ggagatcagc | cctcctgtgc | tcatcagttc | cagcaacccc | acagccgcag | cccgcatcag | 1200 |
| cgaactgtcc | gggctctcct | gcagcgcccc | gtctcaggtc | catataagca | ccactgggtt | 1260 |
| aattgtgacc | ccaccccta | gcagcccggt | gacaactggc | cctgcgttca | cgttcccttc | 1320 |
| agatgtcccc | taccaagctg | cccttggaag | tatgaatcct | ccacttcccc | cacccccttct | 1380 |
| cctggcggcc | accgtactcg | cctccacccc | gtcaggcgct | actgctgctg | ttgctgctgc | 1440 |
| tgctgccgcc | gccgccgctg | ctggaatggg | acccaggcct | gtgatggggt | cctctgaaca | 1500 |
| gattgcacat | ttacggcctc | agactcgtcc | cagtgtatat | gttgctatat | atccgtacac | 1560 |
| tccccggaag | gaagacgaac | tggagctgag | gaaaggggag | atgttttttgg | tgtttgagcg | 1620 |
| ttgccaggac | ggctggtaca | aagggacatc | gatgcatacc | agcaagatag | gcgttttccc | 1680 |
| tgcaactat | gtgcgcccg | tcacaagggc | ggtgacgaat | gcctcccaag | ctaaagtctc | 1740 |
| tatgtctact | gcgggtcagg | caagtcgcgg | ggtgaccatg | gtcagccctt | ccactgcagg | 1800 |
| aggacctaca | cagaagcccc | aaggaaacg | cgtggccgga | atcccagcg | tcgtccccac | 1860 |
| ggctgtggtg | tcagcagctc | atatccagac | aagtcctcag | gctaaggtcc | tgctgcacat | 1920 |
| gtctgggcag | atgacagtca | atcaggcccg | caatgctgtg | aggacagttg | cagcacatag | 1980 |
| ccaggaacgc | cccacagcag | cagtgactcc | catccaggtc | cagaatgccg | cctgccttgg | 2040 |
| tcctgcatcc | gtgggcctgc | cccatcattc | tctggcctcc | caacctctgc | ctccaatggc | 2100 |
| gggtcctgct | gcccacggtg | ctgccgtcag | catcagtcga | accaatgccc | ccatggcctg | 2160 |

```
cgctgcaggg gcttctctgg cctccccaaa tatgaccagt gccatgttgg agacagagcc      2220
cagtggtcgc acagtgacca tcctccctgg actccccaca tctccagaga gtgctgcatc      2280
agcgtgtggg aacagttcag ctgggaaacc agacaaggac agtaagaaag aaaaaaaggg      2340
cctactgaag ctgctttctg gtgcctccac caaacgcaag ccccgagtct ccctccagc       2400 atcacctacc ctggatgtgg agctgggtgc tggggaggct cccttgcagg gagcagtagg      2460
tcctgagctg ccgctagggg gcagccacgg cagagtgggg tcatgcccca cagatggtga      2520
tggtccagtg gccgctggaa cagcagccct agcccaggat gccttccacc gcaagacaag      2580
ctccctggac tccgcagtgc ccattgctcc accacctcgc caggcctgct cctccctggg      2640
cccagtcatg aatgaggccc ggcctgttgt ttgtgaaagg cacagggtgg tggtttccta      2700
ccctcctcag agtgaggccg aacttgaact caaggaagga gatattgtgt ttgttcataa      2760
gaaacgagag gacggctggt tcaaaggcac gttacagagg aatgggaaga ctggcctttt      2820
cccagggagc tttgtggaaa acatctgaga agacgggaca cggagaaagc ttatcatcac      2880
accacgtgtg actaaagagc acaaagcagt tcatagaaa gagcacatct gtggacttcc       2940
agatcttcaa gaaccgagca gaagatgggc acctgactcc agagccccgg cctggttacc      3000 ccagggcag agggaaggag gacacacctg tgtgggttcc gtctctctgg gttctgatgt       3060
gtaaagtgtg ccttgtaatg tctaatggac tttacagata aatgtctttt ttttttttaag     3120 atgtataact aaaatggaca attgtttaca aggcttaact aatttatttg ctttttttaaa    3180 acttgaactt tcttgtaata gcaaat                                           3206
```

<210> SEQ ID NO 9
<211> LENGTH: 892
<212> TYPE: PRT
<213> ORGANISM: Mus musculus

<400> SEQUENCE: 9

```
Met Asp Glu Ser Ala Leu Leu Asp Leu Leu Glu Cys Pro Val Cys Leu
1               5                   10                  15

Glu Arg Leu Asp Ala Ser Ala Lys Val Leu Pro Cys Gln His Thr Phe
            20                  25                  30

Cys Lys Arg Cys Leu Leu Gly Ile Val Gly Ser Arg Asn Glu Leu Arg
        35                  40                  45

Cys Pro Glu Cys Arg Thr Leu Val Gly Ser Gly Val Asp Glu Leu Pro
    50                  55                  60

Ser Asn Ile Leu Leu Val Arg Leu Leu Asp Gly Ile Lys Gln Arg Pro
65                  70                  75                  80

Trp Lys Pro Gly Pro Gly Gly Gly Gly Thr Thr Cys Thr Asn Thr
                85                  90                  95

Leu Arg Ala Gln Gly Ser Thr Val Val Asn Cys Gly Ser Lys Asp Leu
            100                 105                 110

Gln Ser Ser Gln Cys Gly Gln Gln Pro Arg Val Gln Ala Trp Ser Pro
        115                 120                 125

Pro Val Arg Gly Ile Pro Gln Leu Pro Cys Ala Lys Ala Leu Tyr Asn
    130                 135                 140

Tyr Glu Gly Lys Glu Pro Gly Asp Leu Lys Phe Ser Lys Gly Asp Thr
145                 150                 155                 160

Ile Ile Leu Arg Arg Gln Val Asp Glu Asn Trp Tyr His Gly Glu Val
                165                 170                 175

Ser Gly Val His Gly Phe Phe Pro Thr Asn Phe Val Gln Ile Ile Lys
            180                 185                 190
```

-continued

```
Pro Leu Pro Gln Pro Pro Gln Cys Lys Ala Leu Tyr Asp Phe Glu
        195                 200                 205
Val Lys Asp Lys Glu Ala Asp Lys Asp Cys Leu Pro Phe Ala Lys Asp
    210                 215                 220
Asp Val Leu Thr Val Ile Arg Arg Val Asp Glu Asn Trp Ala Glu Gly
225                 230                 235                 240
Met Leu Ala Asp Lys Ile Gly Ile Phe Pro Ile Ser Tyr Val Glu Phe
                245                 250                 255
Asn Ser Ala Ala Lys Gln Leu Ile Glu Trp Asp Lys Pro Val Pro
            260                 265                 270
Gly Val Asp Thr Ala Glu Cys Pro Ser Ala Thr Ala Gln Ser Thr Ser
        275                 280                 285
Ala Ser Lys His Pro Asp Thr Lys Lys Asn Thr Arg Lys Arg His Ser
    290                 295                 300
Phe Thr Ser Leu Thr Met Ala Asn Lys Ser Ser Gln Gly Ser Gln Asn
305                 310                 315                 320
Arg His Ser Met Glu Ile Ser Pro Pro Val Leu Ile Ser Ser Ser Asn
                325                 330                 335
Pro Thr Ala Ala Ala Arg Ile Ser Glu Leu Ser Gly Leu Ser Cys Ser
            340                 345                 350
Ala Pro Ser Gln Val His Ile Ser Thr Thr Gly Leu Ile Val Thr Pro
        355                 360                 365
Pro Pro Ser Ser Pro Val Thr Thr Gly Pro Ala Phe Thr Phe Pro Ser
    370                 375                 380
Asp Val Pro Tyr Gln Ala Ala Leu Gly Ser Met Asn Pro Pro Leu Pro
385                 390                 395                 400
Pro Pro Pro Leu Leu Ala Ala Thr Val Leu Ala Ser Thr Pro Ser Gly
                405                 410                 415
Ala Thr Ala Ala Val Ala Ala Ala Ala Ala Ala Ala Ala Ala Ala Gly
            420                 425                 430
Met Gly Pro Arg Pro Val Met Gly Ser Ser Glu Gln Ile Ala His Leu
        435                 440                 445
Arg Pro Gln Thr Arg Pro Ser Val Tyr Val Ala Ile Tyr Pro Tyr Thr
    450                 455                 460
Pro Arg Lys Glu Asp Glu Leu Glu Leu Arg Lys Gly Glu Met Phe Leu
465                 470                 475                 480
Val Phe Glu Arg Cys Gln Asp Gly Trp Tyr Lys Gly Thr Ser Met His
                485                 490                 495
Thr Ser Lys Ile Gly Val Phe Pro Gly Asn Tyr Val Ala Pro Val Thr
            500                 505                 510
Arg Ala Val Thr Asn Ala Ser Gln Ala Lys Val Ser Met Ser Thr Ala
        515                 520                 525
Gly Gln Ala Ser Arg Gly Val Thr Met Val Ser Pro Ser Thr Ala Gly
    530                 535                 540
Gly Pro Thr Gln Lys Pro Gln Gly Asn Gly Val Ala Gly Asn Pro Ser
545                 550                 555                 560
Val Val Pro Thr Ala Val Val Ser Ala Ala His Ile Gln Thr Ser Pro
                565                 570                 575
Gln Ala Lys Val Leu Leu His Met Ser Gly Gln Met Thr Val Asn Gln
            580                 585                 590
Ala Arg Asn Ala Val Arg Thr Val Ala Ala His Ser Gln Glu Arg Pro
        595                 600                 605
```

-continued

```
Thr Ala Ala Val Thr Pro Ile Gln Val Gln Asn Ala Ala Cys Leu Gly
    610                 615                 620

Pro Ala Ser Val Gly Leu Pro His His Ser Leu Ala Ser Gln Pro Leu
625                 630                 635                 640

Pro Pro Met Ala Gly Pro Ala Ala His Gly Ala Ala Val Ser Ile Ser
                645                 650                 655

Arg Thr Asn Ala Pro Met Ala Cys Ala Ala Gly Ala Ser Leu Ala Ser
            660                 665                 670

Pro Asn Met Thr Ser Ala Met Leu Glu Thr Glu Pro Ser Gly Arg Thr
        675                 680                 685

Val Thr Ile Leu Pro Gly Leu Pro Thr Ser Pro Glu Ser Ala Ala Ser
    690                 695                 700

Ala Cys Gly Asn Ser Ser Ala Gly Lys Pro Asp Lys Asp Ser Lys
705                 710                 715                 720

Glu Lys Lys Gly Leu Leu Lys Leu Leu Ser Gly Ala Ser Thr Lys Arg
                725                 730                 735

Lys Pro Arg Val Ser Pro Pro Ala Ser Pro Thr Leu Asp Val Glu Leu
            740                 745                 750

Gly Ala Gly Glu Ala Pro Leu Gln Gly Ala Val Gly Pro Glu Leu Pro
        755                 760                 765

Leu Gly Gly Ser His Gly Arg Val Gly Ser Cys Pro Thr Asp Gly Asp
    770                 775                 780

Gly Pro Val Ala Ala Gly Thr Ala Ala Leu Ala Gln Asp Ala Phe His
785                 790                 795                 800

Arg Lys Thr Ser Ser Leu Asp Ser Ala Val Pro Ile Ala Pro Pro Pro
                805                 810                 815

Arg Gln Ala Cys Ser Ser Leu Gly Pro Val Met Asn Glu Ala Arg Pro
            820                 825                 830

Val Val Cys Glu Arg His Arg Val Val Ser Tyr Pro Pro Gln Ser
        835                 840                 845

Glu Ala Glu Leu Glu Leu Lys Glu Gly Asp Ile Val Phe Val His Lys
    850                 855                 860

Lys Arg Glu Asp Gly Trp Phe Lys Gly Thr Leu Gln Arg Asn Gly Lys
865                 870                 875                 880

Thr Gly Leu Phe Pro Gly Ser Phe Val Glu Asn Ile
                885                 890

<210> SEQ ID NO 10
<211> LENGTH: 3149
<212> TYPE: DNA
<213> ORGANISM: Drosophila melanogaster

<400> SEQUENCE: 10
catttgtatc cgcttggcca cgagctttgg ctgcacttgg caaacttaat aaattaaaca    60
ttgaatcctg cctattgcaa cgataatata atctgattta gtgcattaag aacgacaagt   120
agcgattata atagtagatt ttagcatttg agctaaattt atttcccaac cgcgtcttgg   180
gattgcgtat gcgtgagcca gtacctgcat gtgtgtgtgt tttggaatgt ggccctgcac   240
gaaattcaaa tagtgaccat ccttgagatt ttgcatactg gcaagatgga cgagcacacg   300
ttaaacgacc tgttggagtg ctccgtgtgt cttgagcgac tggacaccac atcgaaggtg   360
ctgccatgcc agcacaccct ctgccgcaaa tgcttgcagg acattgtggc cagtcagcac   420
aagttgcgat gcccggagtg ccgcatcctg gtctcttgca aaattgatga gctgcctcca   480
aacgtcttgc tgatgcgaat cttagaaggc atgaaacaaa atgcagcagc tggcaaagga   540
```

```
gaagaaaagg gagaggagac tgaaacacag ccggaaaggg ccaaacctca gccgccagcg      600
gaatcagtgg ccccgcctga caaccaacta ctccagctgc agtcacatca gcaatctcat      660
cagccggctc gtcacaagca acgtcgattt ctactccccc acgcctatgc cctctttgac      720
ttcgcctccg gtgaagccac cgatctaaag ttcaagaaag gggatctgat actgatcaag      780
catcgcatcg acaacaactg gtttgtgggt caagcgaatg gtcaggaggg cacatttccc      840
atcaactacg tcaaggtatc ggttccgctg cccatgccgc agtgcattgc catgtatgac      900
tttaagatgg ggcccaacga cgaggaggga tgcctcgaat ttaagaaaag cactgtaata      960
caggtaatgc gccgagttga tcataattgg gcagaaggac gaattggcca gaccatcgga     1020
atctttccaa tagcattcgt tgagctgaat gcagcggcca aaaagctgtt ggacagcggg     1080
ctacacaccc atccattctg ccatccaccg aagcaacagg ggcagcgggc ccttcctccg     1140
gttccagtta ttgatcccac ggtggtcacg aatccagtt cgggatcctc caattccacg     1200
ccgggcagca gcaattcaag ctccacatcc agctcgaata actgcagtcc gaatcaccaa     1260
atctcactgc cgaataccc ccaacatgta gtagcttccg gatcggcgtc tgttcgtttc     1320
cgtgacaagg gagcaaagga gaaacgccac tcactaaatg ctttgctggg aggaggagct     1380
ccattaagtc tgctgcagac caaccgccat tcggctgaaa ttcttagcct gccccatgaa     1440
ctaagccgct tggaagtttc cagctcaaca gctctaaaac ccacgtcagc cccacagaca     1500
tcgcgtgtac ttaagaccac tgttcagcag cagatgcaac cgaatttacc ctggggatac     1560
ttagccctgt tcccatacaa accacgccaa acggatgagc tggaattaaa aaagggttgt     1620
gtttacattg tgaccgaacg atgtgtggac ggttggttca agggaaaaaa ctggttggac     1680
atcactggag tgttcccggg caactacctg acgcccctgc gcgcccgcga ccagcagcag     1740
ttaatgcatc aatggaaata tgttccccaa aatgcagacg cccagatggc acaagtacag     1800
cagcatccag ttgcaccaga tgtgcgactc aacaacatgc tgtccatgca accgcctgat     1860
ttgccacctc gtcagcagca ggctaccgcc acgaccacca gttgctctgt gtggtcgaaa     1920
ccagtggagg cgctgttcag cagaaaatcg gagcccaagc tgaaactgc cacagcttcg     1980
actacgagca gcagttcctc tggagcagtg ggacttatga ggagattaac tcacatgaaa     2040
acacgctcca atctccgggg agcgtccttg cagcaagttc cgaaagaagc tattagcaca     2100
aatgtggaat ttacaacaaa cccatcagct aaattgcatc cagtacatgt aagatccggc     2160
tcgtgcccca gtcagctgca gcacagtcaa ccgctcaatg aaactccagc agccaagaca     2220
gcggcacaac aacagcagtt cctacccaag cagctgcctt ccgcttctac gaacagcgtt     2280
tcgtacggat cgcaacgcgt gaaggaagc aaggaacgtc ctcacttgat ttgcgcgaga     2340
caatcattag atgcagctac atttcgcagt atgtacaaca atgccgcgtc gccgccgcca     2400
cctactactt ccgtgggccc agctgtctac gccggcggtc agcaacaggt gattcctgga     2460
ggtggagcgc aatcccagtt gcatgccaat atgattattg cacccagcca tcggaagtcg     2520
cacagcctag atgcgagtca tgtgctgagt cccagcagca atatgatcac ggaggcggcc     2580
attaaggcca gcgccaccac taagtctcct tactgcacga gggaaagtcg attccgctgc     2640
attgtgccgt atccaccaaa cagtgacatt gaactagagc tacatttggg cgacattatc     2700
tacgtccagc ggaagcagaa gaacggctgg tataagggca cccatgcccg tacccacaaa     2760
accgggctgt tccccgcctc ctttgttgaa ccggattgtt aggaaagtta tggttcaaac     2820
tagaatttat taagcgaaat tccaaattac ttgtctaaaa ggattcaatc gtcggtctat     2880
```

-continued

```
tcgggcttcc aaatacgcaa tctcatatttt ctcttttcaa aaagaaacc gttttgtact    2940 cttccaatcg aatgggcagc tcgccgttgt acttttttat acaatgcttg atcaaaatag    3000
gctagccatg taagacttag ggaacagtta cttaagcctt agcgattagt tagctagaga    3060
aataatctaa ccgatccttg tgccctctac aaagttattt gtaatatacg atactcagta    3120
ataaaaaaaa aaaaaaaaa aaaaaaaa                                        3149
```

<210> SEQ ID NO 11
<211> LENGTH: 838
<212> TYPE: PRT
<213> ORGANISM: Drosophila melanogaster

<400> SEQUENCE: 11

```
Met Asp Glu His Thr Leu Asn Asp Leu Leu Glu Cys Ser Val Cys Leu
1               5                   10                  15

Glu Arg Leu Asp Thr Thr Ser Lys Val Leu Pro Cys Gln His Thr Phe
            20                  25                  30

Cys Arg Lys Cys Leu Gln Asp Ile Val Ala Ser Gln His Lys Leu Arg
        35                  40                  45

Cys Pro Glu Cys Arg Ile Leu Val Ser Cys Lys Ile Asp Glu Leu Pro
    50                  55                  60

Pro Asn Val Leu Leu Met Arg Ile Leu Glu Gly Met Lys Gln Asn Ala
65                  70                  75                  80

Ala Ala Gly Lys Gly Glu Glu Lys Gly Glu Glu Thr Glu Thr Gln Pro
                85                  90                  95

Glu Arg Ala Lys Pro Gln Pro Pro Ala Glu Ser Val Ala Pro Pro Asp
            100                 105                 110

Asn Gln Leu Leu Gln Leu Gln Ser His Gln Gln Ser His Gln Pro Ala
        115                 120                 125

Arg His Lys Gln Arg Arg Phe Leu Leu Pro His Ala Tyr Ala Leu Phe
    130                 135                 140

Asp Phe Ala Ser Gly Glu Ala Thr Asp Leu Lys Phe Lys Lys Gly Asp
145                 150                 155                 160

Leu Ile Leu Ile Lys His Arg Ile Asp Asn Asn Trp Phe Val Gly Gln
                165                 170                 175

Ala Asn Gly Gln Glu Gly Thr Phe Pro Ile Asn Tyr Val Lys Val Ser
            180                 185                 190

Val Pro Leu Pro Met Pro Gln Cys Ile Ala Met Tyr Asp Phe Lys Met
        195                 200                 205

Gly Pro Asn Asp Glu Glu Gly Cys Leu Glu Phe Lys Lys Ser Thr Val
    210                 215                 220

Ile Gln Val Met Arg Arg Val Asp His Asn Trp Ala Glu Gly Arg Ile
225                 230                 235                 240

Gly Gln Thr Ile Gly Ile Phe Pro Ile Ala Phe Val Glu Leu Asn Ala
                245                 250                 255

Ala Ala Lys Lys Leu Leu Asp Ser Gly Leu His Thr His Pro Phe Cys
            260                 265                 270

His Pro Pro Lys Gln Gly Gln Arg Ala Leu Pro Pro Val Pro Val
        275                 280                 285

Ile Asp Pro Thr Val Val Thr Glu Ser Ser Ser Gly Ser Ser Asn Ser
    290                 295                 300

Thr Pro Gly Ser Ser Asn Ser Ser Ser Thr Ser Ser Ser Asn Asn Cys
305                 310                 315                 320

Ser Pro Asn His Gln Ile Ser Leu Pro Asn Thr Pro Gln His Val Val
```

```
                    325                 330                 335
Ala Ser Gly Ser Ala Ser Val Arg Phe Arg Asp Lys Gly Ala Lys Glu
                340                 345                 350

Lys Arg His Ser Leu Asn Ala Leu Leu Gly Gly Gly Ala Pro Leu Ser
            355                 360                 365

Leu Leu Gln Thr Asn Arg His Ser Ala Glu Ile Leu Ser Leu Pro His
        370                 375                 380

Glu Leu Ser Arg Leu Glu Val Ser Ser Ser Thr Ala Leu Lys Pro Thr
385                 390                 395                 400

Ser Ala Pro Gln Thr Ser Arg Val Leu Lys Thr Thr Val Gln Gln Gln
                405                 410                 415

Met Gln Pro Asn Leu Pro Trp Gly Tyr Leu Ala Leu Phe Pro Tyr Lys
            420                 425                 430

Pro Arg Gln Thr Asp Glu Leu Glu Leu Lys Lys Gly Cys Val Tyr Ile
        435                 440                 445

Val Thr Glu Arg Cys Val Asp Gly Trp Phe Lys Gly Lys Asn Trp Leu
    450                 455                 460

Asp Ile Thr Gly Val Phe Pro Gly Asn Tyr Leu Thr Pro Leu Arg Ala
465                 470                 475                 480

Arg Asp Gln Gln Gln Leu Met His Gln Trp Lys Tyr Val Pro Gln Asn
                485                 490                 495

Ala Asp Ala Gln Met Ala Gln Val Gln Gln His Pro Val Ala Pro Asp
            500                 505                 510

Val Arg Leu Asn Asn Met Leu Ser Met Gln Pro Pro Asp Leu Pro Pro
        515                 520                 525

Arg Gln Gln Gln Ala Thr Ala Thr Thr Thr Ser Cys Ser Val Trp Ser
    530                 535                 540

Lys Pro Val Glu Ala Leu Phe Ser Arg Lys Ser Glu Pro Lys Pro Glu
545                 550                 555                 560

Thr Ala Thr Ala Ser Thr Thr Ser Ser Ser Ser Gly Ala Val Gly
                565                 570                 575

Leu Met Arg Arg Leu Thr His Met Lys Thr Arg Ser Lys Ser Pro Gly
            580                 585                 590

Ala Ser Leu Gln Gln Val Pro Lys Glu Ala Ile Ser Thr Asn Val Glu
        595                 600                 605

Phe Thr Thr Asn Pro Ser Ala Lys Leu His Pro Val His Val Arg Ser
    610                 615                 620

Gly Ser Cys Pro Ser Gln Leu Gln His Ser Gln Pro Leu Asn Glu Thr
625                 630                 635                 640

Pro Ala Ala Lys Thr Ala Ala Gln Gln Gln Phe Leu Pro Lys Gln
                645                 650                 655

Leu Pro Ser Ala Ser Thr Asn Ser Val Ser Tyr Gly Ser Gln Arg Val
            660                 665                 670

Lys Gly Ser Lys Glu Arg Pro His Leu Ile Cys Ala Arg Gln Ser Leu
        675                 680                 685

Asp Ala Ala Thr Phe Arg Ser Met Tyr Asn Asn Ala Ala Ser Pro Pro
    690                 695                 700

Pro Pro Thr Thr Ser Val Ala Pro Ala Val Tyr Ala Gly Gly Gln Gln
705                 710                 715                 720

Gln Val Ile Pro Gly Gly Ala Gln Ser Gln Leu His Ala Asn Met
                725                 730                 735

Ile Ile Ala Pro Ser His Arg Lys Ser His Ser Leu Asp Ala Ser His
            740                 745                 750
```

```
Val Leu Ser Pro Ser Ser Asn Met Ile Thr Glu Ala Ala Ile Lys Ala
        755                 760                 765

Ser Ala Thr Thr Lys Ser Pro Tyr Cys Thr Arg Glu Ser Arg Phe Arg
    770                 775                 780

Cys Ile Val Pro Tyr Pro Asn Ser Asp Ile Glu Leu Glu Leu His
785                 790                 795                 800

Leu Gly Asp Ile Ile Tyr Val Gln Arg Lys Gln Lys Asn Gly Trp Tyr
                805                 810                 815

Lys Gly Thr His Ala Arg Thr His Lys Thr Gly Leu Phe Pro Ala Ser
            820                 825                 830

Phe Val Glu Pro Asp Cys
        835

<210> SEQ ID NO 12
<211> LENGTH: 18
<212> TYPE: DNA
<213> ORGANISM: Artificial Sequence
<220> FEATURE:
<223> OTHER INFORMATION: sense primer

<400> SEQUENCE: 12
cttgccttgc cagcatac                                                18

<210> SEQ ID NO 13
<211> LENGTH: 18
<212> TYPE: DNA
<213> ORGANISM: Artificial Sequence
<220> FEATURE:
<223> OTHER INFORMATION: anti-sense primer

<400> SEQUENCE: 13
ctgccagcat tccttcag                                                18

<210> SEQ ID NO 14
<211> LENGTH: 21
<212> TYPE: DNA
<213> ORGANISM: Artificial Sequence
<220> FEATURE:
<223> OTHER INFORMATION: target sequence

<400> SEQUENCE: 14
aacagaggcc ttggaaacct g                                            21

<210> SEQ ID NO 15
<211> LENGTH: 21
<212> TYPE: DNA
<213> ORGANISM: Artificial Sequence
<220> FEATURE:
<223> OTHER INFORMATION: siRNA sense strand

<400> SEQUENCE: 15
ttcagaggcc uuggaaaccu g                                            21

<210> SEQ ID NO 16
<211> LENGTH: 21
<212> TYPE: DNA
<213> ORGANISM: Artificial Sequence
<220> FEATURE:
<223> OTHER INFORMATION: siRNA anti-sense strand

<400> SEQUENCE: 16
ttcagguuuc caaggccucu g                                            21
```

<210> SEQ ID NO 17
<211> LENGTH: 21
<212> TYPE: DNA
<213> ORGANISM: Artificial Sequence
<220> FEATURE:
<223> OTHER INFORMATION: target sequence

<400> SEQUENCE: 17
aaagagcctg gagaccttaa a                                              21

<210> SEQ ID NO 18
<211> LENGTH: 21
<212> TYPE: DNA
<213> ORGANISM: Artificial Sequence
<220> FEATURE:
<223> OTHER INFORMATION: siRNA sense strand

<400> SEQUENCE: 18
ttagagccug gagaccuuaa a                                              21

<210> SEQ ID NO 19
<211> LENGTH: 21
<212> TYPE: DNA
<213> ORGANISM: Artificial Sequence
<220> FEATURE:
<223> OTHER INFORMATION: siRNA anti-sense strand

<400> SEQUENCE: 19
ttuuuaaggu cuccaggcuc u                                              21

<210> SEQ ID NO 20
<211> LENGTH: 21
<212> TYPE: DNA
<213> ORGANISM: Artificial Sequence
<220> FEATURE:
<223> OTHER INFORMATION: target sequence

<400> SEQUENCE: 20
aaggattggt atgtgactct g                                              21

<210> SEQ ID NO 21
<211> LENGTH: 22
<212> TYPE: DNA
<213> ORGANISM: Artificial Sequence
<220> FEATURE:
<223> OTHER INFORMATION: siRNA sense strand

<400> SEQUENCE: 21
ttggaauugg uaugugacuc ug                                             22

<210> SEQ ID NO 22
<211> LENGTH: 21
<212> TYPE: DNA
<213> ORGANISM: Artificial Sequence
<220> FEATURE:
<223> OTHER INFORMATION: siRNA anti-sense strand

<400> SEQUENCE: 22
ttcagaguca cauaccaauc c                                              21

<210> SEQ ID NO 23
<211> LENGTH: 21
<212> TYPE: DNA
<213> ORGANISM: Artificial Sequence
<220> FEATURE:
<223> OTHER INFORMATION: target sequence

```
<400> SEQUENCE: 23
aagctggatt atctcctgtt g                                              21

<210> SEQ ID NO 24
<211> LENGTH: 21
<212> TYPE: DNA
<213> ORGANISM: Artificial Sequence
<220> FEATURE:
<223> OTHER INFORMATION: siRNA sense strand

<400> SEQUENCE: 24
ttgcuggauu aucuccuguu g                                              21

<210> SEQ ID NO 25
<211> LENGTH: 21
<212> TYPE: DNA
<213> ORGANISM: Artificial Sequence
<220> FEATURE:
<223> OTHER INFORMATION: siRNA anti-sense strand

<400> SEQUENCE: 25
ttcaacagga gauaauccag c                                              21

<210> SEQ ID NO 26
<211> LENGTH: 41
<212> TYPE: PRT
<213> ORGANISM: Homo sapiens

<400> SEQUENCE: 26

Cys Pro Val Cys Leu Glu Arg Leu Asp Ala Ser Ala Lys Val Leu Pro
1               5                   10                  15

Cys Gln His Thr Phe Cys Lys Arg Cys Leu Leu Gly Ile Val Gly Ser
            20                  25                  30

Arg Asn Glu Leu Arg Cys Pro Glu Cys
        35                  40

<210> SEQ ID NO 27
<211> LENGTH: 56
<212> TYPE: PRT
<213> ORGANISM: Homo sapiens

<400> SEQUENCE: 27

Pro Cys Ala Lys Ala Leu Tyr Asn Tyr Glu Gly Lys Glu Pro Gly Asp
1               5                   10                  15

Leu Lys Phe Ser Lys Gly Asp Ile Ile Leu Arg Arg Gln Val Asp
            20                  25                  30

Glu Asn Trp Tyr His Gly Glu Val Asn Gly Ile His Gly Phe Phe Pro
        35                  40                  45

Thr Asn Phe Val Gln Ile Ile Lys
    50                  55

<210> SEQ ID NO 28
<211> LENGTH: 60
<212> TYPE: PRT
<213> ORGANISM: Homo sapiens

<400> SEQUENCE: 28

Pro Gln Cys Lys Ala Leu Tyr Asp Phe Glu Val Lys Asp Lys Glu Ala
1               5                   10                  15

Asp Lys Asp Cys Leu Pro Phe Ala Lys Asp Asp Val Leu Thr Val Ile
            20                  25                  30
```

```
Arg Arg Val Asp Glu Asn Trp Ala Glu Gly Met Leu Ala Asp Lys Ile
        35                  40                  45

Gly Ile Phe Pro Ile Ser Tyr Val Glu Phe Asn Ser
    50                  55                  60

<210> SEQ ID NO 29
<211> LENGTH: 58
<212> TYPE: PRT
<213> ORGANISM: Homo sapiens

<400> SEQUENCE: 29

Ser Val Tyr Val Ala Ile Tyr Pro Tyr Thr Pro Arg Lys Glu Asp Glu
  1               5                  10                  15

Leu Glu Leu Arg Lys Gly Glu Met Phe Leu Val Phe Glu Arg Cys Gln
                 20                  25                  30

Asp Gly Trp Phe Lys Gly Thr Ser Met His Thr Ser Lys Ile Gly Val
            35                  40                  45

Phe Pro Gly Asn Tyr Val Ala Pro Val Thr
    50                  55

<210> SEQ ID NO 30
<211> LENGTH: 57
<212> TYPE: PRT
<213> ORGANISM: Homo sapiens

<400> SEQUENCE: 30

Glu Arg His Arg Val Val Ser Tyr Pro Pro Gln Ser Glu Ala Glu
  1               5                  10                  15

Leu Glu Leu Lys Glu Gly Asp Ile Val Phe Val His Lys Lys Arg Glu
                 20                  25                  30

Asp Gly Trp Phe Lys Gly Thr Leu Gln Arg Asn Gly Lys Thr Gly Leu
            35                  40                  45

Phe Pro Gly Ser Phe Val Glu Asn Ile
    50                  55

<210> SEQ ID NO 31
<211> LENGTH: 121
<212> TYPE: DNA
<213> ORGANISM: Homo sapiens

<400> SEQUENCE: 31
tgtccggtgt gtctagagcg ccttgatgct tctgcgaagg tcttgccttg ccagcatacg      60
ttttgcaagc gatgtttgct ggggatcgta ggttctcgaa atgaactcag atgtcccgag     120
t                                                                     121

<210> SEQ ID NO 32
<211> LENGTH: 165
<212> TYPE: DNA
<213> ORGANISM: Homo sapiens

<400> SEQUENCE: 32
ccatgtgcca aagcgttata caactatgaa ggaaaagagc ctggagacct taaattcagc      60
aaaggcgaca tcatcatttt gcgaagacaa gtggatgaaa attggtacca tggggaagtc     120
aatggaatcc atggcttttt ccccaccaac tttgtgcaga ttatt                     165

<210> SEQ ID NO 33
<211> LENGTH: 177
<212> TYPE: DNA
```

<213> ORGANISM: Homo sapiens

<400> SEQUENCE: 33

```
cctcagtgca aagcacttta tgactttgaa gtgaaagaca aggaagcaga caaagattgc    60
cttccatttg caaaggatga tgttctgact gtgatccgaa gagtggatga aaactgggct   120
gaaggaatgc tggcagacaa aataggaata tttccaattt catatgttga gtttaac      177
```

<210> SEQ ID NO 34
<211> LENGTH: 171
<212> TYPE: DNA
<213> ORGANISM: Homo sapiens

<400> SEQUENCE: 34

```
agtgtgtatg ttgctatata tccatacact cctcggaaag aggatgaact agagctgaga    60
aaagggaga tgttttagt gtttgagcgc tgccaggatg gctggttcaa agggacatcc    120
atgcatacca gcaagatagg ggttttccct ggcaattatg tggcaccagt c            171
```

<210> SEQ ID NO 35
<211> LENGTH: 171
<212> TYPE: DNA
<213> ORGANISM: Homo sapiens

<400> SEQUENCE: 35

```
gaaaggcaca gggtggtggt ttcctatcct cctcagagtg aggcagaact gaacttaaa    60
gaaggagata ttgtgtttgt tcataaaaaa cgagaggat gctggttcaa aggcacatta   120
caacgtaatg ggaaaactgg ccttttccca ggaagctttg tggaaaacat a            171
```

<210> SEQ ID NO 36
<211> LENGTH: 7
<212> TYPE: PRT
<213> ORGANISM: Artificial Sequence
<220> FEATURE:
<223> OTHER INFORMATION: chemically synthesized

<400> SEQUENCE: 36

Arg Pro Asp Pro Thr Ala Pro
1               5

<210> SEQ ID NO 37
<211> LENGTH: 7
<212> TYPE: PRT
<213> ORGANISM: Artificial Sequence
<220> FEATURE:
<223> OTHER INFORMATION: chemically synthesized

<400> SEQUENCE: 37

Arg Pro Leu Pro Val Ala Pro
1               5

<210> SEQ ID NO 38
<211> LENGTH: 7
<212> TYPE: PRT
<213> ORGANISM: Artificial Sequence
<220> FEATURE:
<223> OTHER INFORMATION: chemically synthesized

<400> SEQUENCE: 38

Arg Pro Glu Pro Thr Ala Pro
1               5

<210> SEQ ID NO 39

<211> LENGTH: 4
<212> TYPE: PRT
<213> ORGANISM: Artificial Sequence
<220> FEATURE:
<223> OTHER INFORMATION: chemically synthesized

<400> SEQUENCE: 39

Tyr Glu Asp Leu
 1

<210> SEQ ID NO 40
<211> LENGTH: 7
<212> TYPE: PRT
<213> ORGANISM: Artificial Sequence
<220> FEATURE:
<223> OTHER INFORMATION: chemically synthesized

<400> SEQUENCE: 40

Pro Thr Ala Pro Pro Glu Tyr
 1               5

<210> SEQ ID NO 41
<211> LENGTH: 10
<212> TYPE: PRT
<213> ORGANISM: Artificial Sequence
<220> FEATURE:
<223> OTHER INFORMATION: chemically synthesized

<400> SEQUENCE: 41

Arg Pro Glu Pro Thr Ala Pro Pro Glu Glu
 1               5                  10

<210> SEQ ID NO 42
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: VARIANT
<222> LOCATION: 2
<223> OTHER INFORMATION: Xaa = Thr or Ser

<400> SEQUENCE: 42

Pro Xaa Ala Pro
 1

<210> SEQ ID NO 43
<211> LENGTH: 5
<212> TYPE: PRT
<213> ORGANISM: Artificial Sequence
<220> FEATURE:
<223> OTHER INFORMATION: chemically synthesized

<400> SEQUENCE: 43

Pro Phe Arg Asp Tyr
 1               5

<210> SEQ ID NO 44
<211> LENGTH: 7
<212> TYPE: PRT
<213> ORGANISM: Artificial Sequence
<220> FEATURE:
<223> OTHER INFORMATION: chemically synthesized

<400> SEQUENCE: 44

Arg Gln Gly Pro Lys Glu Pro
 1               5

```
<210> SEQ ID NO 45
<211> LENGTH: 9
<212> TYPE: PRT
<213> ORGANISM: Artificial Sequence
<220> FEATURE:
<223> OTHER INFORMATION: chemically synthesized

<400> SEQUENCE: 45

Arg Gln Gly Pro Lys Glu Pro Phe Arg
 1               5

<210> SEQ ID NO 46
<211> LENGTH: 9
<212> TYPE: PRT
<213> ORGANISM: Artificial Sequence
<220> FEATURE:
<223> OTHER INFORMATION: chemically synthesized

<400> SEQUENCE: 46

Arg Pro Glu Pro Thr Ala Pro Glu Glu
 1               5

<210> SEQ ID NO 47
<211> LENGTH: 7
<212> TYPE: PRT
<213> ORGANISM: Artificial Sequence
<220> FEATURE:
<223> OTHER INFORMATION: chemically synthesized
<220> FEATURE:
<221> NAME/KEY: VARIANT
<222> LOCATION: 2, 3
<223> OTHER INFORMATION: Xaa = Any Amino Acid
<220> FEATURE:
<221> NAME/KEY: VARIANT
<222> LOCATION: 5
<223> OTHER INFORMATION: Xaa = Thr or Ser

<400> SEQUENCE: 47

Arg Xaa Xaa Pro Xaa Ala Pro
 1               5

<210> SEQ ID NO 48
<211> LENGTH: 4
<212> TYPE: PRT
<213> ORGANISM: Artificial Sequence
<220> FEATURE:
<223> OTHER INFORMATION: chemically synthesized

<400> SEQUENCE: 48

Pro Thr Ala Pro
 1
```

POSH NUCLEIC ACIDS, POLYPEPTIDES AND RELATED METHODS

RELATED APPLICATIONS

This application claims the benefit of the filing date of U.S. Provisional Applications No. 60/345,846, filed Nov. 9, 2001, and No. 60/364,530, filed Mar. 15, 2002, the specifications of which are hereby incorporated by reference in their entirety.

BACKGROUND

Potential drug target validation involves determining whether a DNA, RNA or protein molecule is implicated in a disease process and is therefore a suitable target for development of new therapeutic drugs. Drug discovery, the process by which bioactive compounds are identified and characterized, is a critical step in the development of new treatments for human diseases. The landscape of drug discovery has changed dramatically due to the genomics revolution. DNA and protein sequences are yielding a host of new drug targets and an enormous amount of associated information.

The identification of genes and proteins involved in various disease states or key biological processes, such as inflammation and immune response, is a vital part of the drug design process. Many diseases and disorders could be treated or prevented by decreasing the expression of one or more genes involved in the molecular etiology of the condition if the appropriate molecular target could be identified and appropriate antagonists developed. For example, cancer, in which one or more cellular oncogenes become activated and result in the unchecked progression of cell cycle processes, could be treated by antagonizing appropriate cell cycle control genes. Furthermore many human genetic diseases, such as Huntington's disease, and certain prior conditions, which are influenced by both genetic and epigenetic factors, result from the inappropriate activity of a polypeptide as opposed to the complete loss of its function. Accordingly, antagonizing the aberrant function of such mutant genes would provide a means of treatment. Additionally, infectious diseases such as HIV have been successfully treated with molecular antagonists targeted to specific essential retroviral proteins such as HIV protease or reverse transcriptase. Drug therapy strategies for treating such diseases and disorders have frequently employed molecular antagonists which target the polypeptide product of the disease gene(s). However the discovery of relevant gene or protein targets is often difficult and time consuming.

One area of particular interest is the identification of host genes and proteins that are co-opted by viruses during the viral life cycle. The serious and incurable nature of many viral diseases, coupled with the high rate of mutations found in many viruses, makes the identification of antiviral agents a high priority for the improvement of world health. Genes and proteins involved in a viral life cycle are also appealing as a subject for investigation because such genes and proteins will typically have additional activities in the host cell and may play a role in other non-viral disease states.

Viral maturation involves the proteolytic processing of the Gag proteins and the activity of various host proteins. It is believed that cellular machineries for exo/endocytosis and for ubiquitin conjugation may be involved in the maturation. In particular, the assembly, budding and subsequent release of retroid viruses, RNA viruses and envelop viruses, such as various retroviruses, rhabdoviruses, lentiviruses, and filoviruses may involve the Gag polyprotein. After its synthesis, Gag is targeted to the plasma membrane where it induces budding of nascent virus particles.

The role of ubiquitin in virus assembly was suggested by Dunigan et al. (1988, Virology 165, 310, Meyers et al. 1991, Virology 180, 602), who observed that mature virus particles were enriched in unconjugated ubiquitin. More recently, it was shown that proteasome inhibitors suppress the release of HIV-1, HIV-2 and virus-like particles derived from SIV and RSV Gag. Also, inhibitors affect Gag processing and maturation into infectious particles (Schubert et al 2000, PNAS 97, 13057, Harty et al. 2000, PNAS 97, 13871, Strack et al. 2000, PNAS 97, 13063, Patnaik et al. 2000, PNAS 97, 13069).

It is well known in the art that ubiquitin-mediated proteolysis is the major pathway for the selective, controlled degradation of intracellular proteins in eukaryotic cells. Ubiquitin modification of a variety of protein targets within the cell appears to be important in a number of basic cellular functions such as regulation of gene expression, regulation of the cell-cycle, modification of cell surface receptors, biogenesis of ribosomes, and DNA repair. One major function of the ubiquitin-mediated system is to control the half-lives of cellular proteins. The half-life of different proteins can range from a few minutes to several days, and can vary considerably depending on the cell-type, nutritional and environmental conditions, as well as the stage of the cell-cycle.

Targeted proteins undergoing selective degradation, presumably through the actions of a ubiquitin-dependent proteosome, are covalently tagged with ubiquitin through the formation of an isopeptide bond between the C-terminal glycyl residue of ubiquitin and a specific lysyl residue in the substrate protein. This process is catalyzed by a ubiquitin-activating enzyme (E1) and a ubiquitin-conjugating enzyme (E2), and in some instances may also require auxiliary substrate recognition proteins (E3s). Following the linkage of the first ubiquitin chain, additional molecules of ubiquitin may be attached to lysine side chains of the previously conjugated moiety to form branched multi-ubiquitin chains.

The conjugation of ubiquitin to protein substrates is a multi-step process. In an initial ATP requiring step, a thioester is formed between the C-terminus of ubiquitin and an internal cysteine residue of an E1 enzyme. Activated ubiquitin may then be transferred to a specific cysteine on one of several E2 enzymes. Finally, these E2 enzymes donate ubiquitin to protein substrates, typically with the assistance of a C3 protein, also known as a ubiquitin enzyme. In certain instances, substrates are recognized directly by the ubiquitin-conjugated E2 enzyme.

It is also known that the ubiquitin system plays a role in a wide range of cellular processes including cell cycle progression, apoptosis, and turnover of many membrane receptors. In viral infections, the ubiquitin system is involved not only with assembly, budding and release, but also with repression of host proteins such as p53, which may lead to a viral-induced neoplasm. The HIV Vpu protein interacts with an E3 protein that regulates IκB degradation, and is thought to promote apoptosis of infected cells by indirectly inhibiting NF-κB activity (Bour et al. (2001) J Exp Med 194:1299-311; U.S. Pat. No. 5,932,425). The ubiquitin system regulates protein function by both mono-ubiquitinotin and poly-ubiquitinotin, and poly-ubiquitinotin is primarily associated with protein degradation.

The vesicular trafficking systems are the major pathways for the distribution of proteins among cell organelles, the plasma membrane and the extracellular medium. The vesicular trafficking systems may be directly or indirectly involved in a variety of disease states. The major vesicle trafficking systems in eukaryotic cells include those systems that are mediated by clathrin-coated vesicles and coatomer-coated vesicles. Clathrin-coated vesicles are generally involved in transport, such as in the case of receptor mediated endocytosis, between the plasma membrane and the early endosomes, as well as from the trans-Golgi network to endosomes. Coatomer-coated vesicles include coat protein I (COP-I) coated vesicles and COP-II coated vesicles, both of which tend to mediate transport of a variety of molecules between the ER and Golgi cisternae. In each case, a vesicle is formed by budding out from a portion of membrane that is coated with coat proteins, and the vesicle sheds its coat prior to fusing with the target membrane.

Clathrin coats assemble on the cytoplasmic face of a membrane, forming pits that ultimately pinch off to become vesicles. Clathrin itself is composed of two subunits, the clathrin heavy chain and the clathrin light chain, that form the clathrin triskelion. Clathrins associate with a host of other proteins, including the assembly protein, AP180, the adaptor complexes (AP1, AP2, AP3 and AP4), beta-arrestin, arrestin 3, auxilin, epsin, Eps15, v-SNAREs, amphiphysins, dynamin, synaptojanin and endophilin. The adaptor complexes promote clathrin cage formation, and help connect clathrin up to the membrane, membrane proteins, and many of the preceding components. AP1 associates with clathrin coated vesicles derived from the trans-Golgi network and contains $\gamma$, $\beta1$, $\mu1$ and $\sigma1$ polypeptide chains. AP2 associates with endocytic clathrin coated vesicles and contains $\alpha$, $\beta2$, $\mu2$, and $\sigma2$ polypeptides. Interactions between the clathrin complex and other proteins are mediated by a variety of domains found in the complex proteins, such as SH3 (Src homology 3) domains, PH (pleckstrin homology) domains, EH domains and NPF domains. (Marsh et al. (1999) Science 285:215-20; Pearse et al. (2000) Curr Opin Struct Biol 10(2):220-8).

Coatomer-coated vesicle formation is initiated by recruitment of a small GTPase (eg. ARF or SAR) by its cognate guanine nucleotide excahnge factor (e.g. SEC12, GEA1, GEA2). The initial complex is recognized by a coat protein complex (COPI or COPII). The coat then grows across the membrane, and various cargo proteins become entrapped in the growing network. The membrane ultimately bulges and becomes a vesicle. The coat proteins stimulate the GTPase activity of the GTPase, and upon hydrolysis of the GTP, the coat proteins are released from the complex, uncoating the vesicle. Other proteins associated with coatomer coated vesicles include v-SNAREs, Rab GTPases and various receptors that help recruit the appropriate cargo proteins. (Springer et al. (1999) Cell 97:145-48).

It would be beneficial to identify proteins involved in one or more of these processs for use in, among other things, drug screening methods.

SUMMARY

In part, the application provides a novel ubiquitin ligase, POSH (Plenty Of SH3 domains) nucleic acid sequences and proteins encoded thereby. In certain embodiments, POSH proteins play a role in viral maturation. Optionally, POSH acts in the assembly or trafficking of complexes that mediate viral release. In one embodiment, POSH polypeptides may stimulate ubiquitylation of certain proteins or stimulate membrane fusion or both. As one of skill in the art can readily appreciate, a POSH protein may form multiple different complexes at different times. In certain embodiments, the invention provides polypeptides that associate with POSH (POSH AP) and polypeptides that involved in POSH mediated biological processes. In certain embodiments, a POSH polypeptide functions in vesicular trafficking. In further embodiments, a POSH polypeptide regulates a Rac signaling pathway. In yet another embodiment, a POSH polypeptide regulates a JNK pathway. In an additional embodiment, a POSH polypeptide regulates NF-κB. In another embodiment, a POSH polypeptide regulates apoptosis.

In some aspects, the invention provides nucleic acid sequences and proteins encoded thereby, as well as oligonucleotides derived from the nucleic acid sequences, antibodies directed to the encoded proteins, screening assays to identify agents that modulate POSH, and diagnostic methods for detecting cells infected with a virus, preferably an envelop virus, an RNA virus and particulalry a retroidvirus.

In one aspect, the invention provides an isolated nucleic acid comprising a nucleotide sequence which hybridizes under stringent conditions to a sequence of SEQ ID NOs: 1, 3, 4, 6, 8 and/or 10 or a sequence complementary thereto. In a related embodiment, the nucleic acid is at least about 80%, 90%, 95%, or 97-98%, or 100% identical to a sequence corresponding to at least about 12, at least about 15, at least about 25, at least about 40, at least about 100, at least about 300, at least about 500, at least about 1000, or at least about 2500 consecutive nucleotides up to the full length of SEQ ID NO: 1, 3, 4, 6, 8 and/or 10, or a sequence complementary thereto.

In one aspect, the invention provides an isolated nucleic acid comprising a nucleotide sequence which hybridizes under stringent conditions to a sequence of SEQ ID NOs: 31-35 or a sequence complementary thereto. In a related embodiment, the nucleic acid is at least about 80%, 90%, 95%, or 97-98%, or 100% identical to a sequence corresponding to at least about 12, at least about 15, at least about 25, consecutive nucleotides up to the full length of SEQ ID NO: 31-35, or a sequence complementary thereto.

In other embodiments, the invention provides a nucleic acid comprising a nucleotide sequence which hybridizes under stringent conditions to a sequence of SEQ ID Nos. 1, 3, 4, 6, 8 and/or 10, or a nucleotide sequence that is at least about 80%, 90%, 95%, or 97-98%, or 100% identical to a sequence corresponding to at least about 12, at least about 15, at least about 25, at least about 40, at least about 100, at least about 300, at least about 500, at least about 1000, or at least about 2500 consecutive nucleotides up to the full length of SEQ ID NO: 1, 3, 4, 6, 8 and/or 10, or a sequence complementary thereto, and a transcriptional regulatory sequence operably linked to the nucleotide sequence to render the nucleotide sequence suitable for use as an expression vector. In another embodiment, the nucleic acid may be included in an expression vector capable of replicating in a prokaryotic or eukaryotic cell. In a related embodiment, the invention provides a host cell transfected with the expression vector.

In yet another embodiment, the invention provides a substantially pure nucleic acid which hybridizes under stringent conditions to a nucleic acid probe corresponding to at least about 12, at least about 15, at least about 25, or at least about 40 consecutive nucleotides up to the full length of SEQ ID NO:1, 3, 4, 6, 8 and/or 10, or a sequence complementary thereto or up to the full length of the gene of which said sequence is a fragment. The invention also provides an antisense oligonucleotide analog which hybridizes under stringent conditions to at least 12, at least 25, or at least 50 consecutive nucleotides up to the full length of SEQ ID NO:1 and/or 3, or a sequence complementary thereto.

In a further embodiment, the invention provides a nucleic acid comprising a nucleic acid encoding an amino acid sequence as set forth in any of SEQ ID Nos: 2, 5, 7, 9 or 11, or a nucleic acid complement thereof. In a related embodiment, the encoded amino acid sequence is at least about 80%, 90%, 95%, or 97-98%, or 100% identical to a sequence corresponding to at least about 12, at least about 15, at least about 25, or at least about 40, at least about 100, at least about 200, at least about 300, at least about 400 or at least about 500 consecutive amino acids up to the full length of any of SEQ ID Nos:2, 5, 7, 9 or 11.

In another embodiment, the invention provides a probe/primer comprising a substantially purified oligonucleotide, said oligonucleotide containing a region of nucleotide sequence which hybridizes under stringent conditions to at least about 12, at least about 15, at least about 25, or at least about 40 consecutive nucleotides of sense or antisense sequence selected from SEQ ID Nos: 1, 3, 4, 6, 8 and/or 10, or a sequence complementary thereto. In preferred embodiments, the probe selectively hybridizes with a target nucleic acid. In another embodiment, the probe may include a label group attached thereto and able to be detected. The label group may be selected from radioisotopes, fluorescent compounds, enzymes, and enzyme co-factors. The invention further provides arrays of at least about 10, at least about 25, at least about 50, or at least about 100 different probes as described above attached to a solid support.

In another aspect, the invention provides polypeptides. In one embodiment, the invention pertains to a polypeptide including an amino acid sequence encoded by a nucleic acid comprising a nucleotide sequence which hybridizes under stringent conditions to a sequence of SEQ ID Nos:1, 3, 4, 6, 8 and/or 10, or a sequence complementary thereto, or a fragment comprising at least about 25, or at least about 40 amino acids thereof.

In a preferred embodiment, the POSH polypeptide comprises a sequence that is identical with or homologous to any of SEQ ID Nos: 2, 5, 7, 9 or 11. For instance, a POSH polypeptide preferably has an amino acid sequence at least 60% homologous to a polypeptide represented by any of SEQ ID Nos:2, 5, 7, 9 or 11 and polypeptides with higher sequence homologies of, for example, 80%, 90% or 95% are also contemplated. The POSH polypeptide can comprise a full length protein, such as represented in the sequence listings, or it can comprise a fragment of, for instance, at least 5, 10, 20, 50, 100, 150, 200, 250, 300, 400 or 500 or more amino acids in length.

In another embodiment, the application provides polypeptides comprising a sequence that is at least 80%, 90% or 95% identical with or homologous to any of SEQ ID Nos: 26-30.

In another preferred embodiment, the invention features a purified or recombinant polypeptide fragment of a POSH polypeptide, which polypeptide has the ability to modulate, e.g., mimic or antagonize, an activity of a wild-type POSH protein. Preferably, the polypeptide fragment comprises a sequence identical or homologous to an amino acid sequence designated in any of SEQ ID Nos: 2, 5, 7, 9 or 11.

Moreover, as described below, the POSH polypeptide can be either an agonist (e.g. mimics), or alternatively, an antagonist of a biological activity of a naturally occurring form of the protein, e.g., the polypeptide is able to modulate the intrinsic biological activity of a POSH protein or a POSH complex, such as an enzymatic activity, binding to other cellular components, cellular compartmentalization, membrane reorganization and the like.

The subject proteins can also be provided as chimeric molecules, such as in the form of fusion proteins. For instance, the POSH polypeptide can be provided as a recombinant fusion protein which includes a second polypeptide portion, e.g., a second polypeptide having an amino acid sequence unrelated (heterologous) to POSH, e.g. the second polypeptide portion is glutathione-S-transferase, e.g. the second polypeptide portion is an enzymatic activity such as alkaline phosphatase, e.g. the second polypeptide portion is an epitope tag, etc.

Yet another aspect of the present invention concerns an immunogen comprising a POSH polypeptide in an immunogenic preparation, the immunogen being capable of eliciting an immune response specific for the POSH polypeptide; e.g. a humoral response, e.g. an antibody response; e.g. a cellular response. In preferred embodiments, the immunogen comprises an antigenic determinant, e.g. a unique determinant, from a protein represented by SEQ ID NO:2.

In yet another aspect, this invention provides antibodies immunoreactive with one or more POSH polypeptides. In one embodiment, antibodies are specific for an SH3 domain or a RING domain derived from a POSH polypeptide. In a more specific embodiment, the domain is part of an amino acid sequence set forth in SEQ ID NO:2. In a set of exemplary embodiments, an antibody binds to one or more SH3 domains represented by amino acids 137-192, 199-258, 448-505 and 832-888 of SEQ ID NO:2 and are set forth in any one of SEQ ID Nos: 27-20. In another exemplary embodiment, an antibody binds to a RING domain represented by amino acids 12-52 of SEQ ID NO:2 and is set forth in SEQ ID No: 26. In another embodiment, the antibodies are immunoreactive with one or more proteins having an amino acid sequence that is at least 80% identical, at least 90% identical or at least 95% identical to an amino acid sequence as set forth in SEQ ID NO:2. In other embodiments, an antibody is immunoreactive with one or more proteins having an amino acid sequence that is 85%, 90%, 95%, 98%, 99% or identical to an amino acid sequence as set forth in SEQ ID NO:2.

In certain embodiments, the subject POSH nucleic acids will include a transcriptional regulatory sequence, e.g. at least one of a transcriptional promoter or transcriptional enhancer sequence, which regulatory sequence is operably linked to the POSH sequence. Such regulatory sequences can be used to render the POSH sequence suitable for use as an expression vector.

In yet another aspect, the invention provides an assay for screening test compounds for inhibitors, or alternatively, potentiators, of an interaction between a POSH polypeptide and a POSH-associated protein (POSH-AP) such as a GTPase or a late domain region of an RNA virus such as a retrovirus. An exemplary method includes the steps of (i) combining POSH-AP, a POSH polypeptide, and a test compound, e.g., under conditions wherein, but for the test compound, the POSH polypeptide and POSH-AP are able to interact; and (ii) detecting the formation of a complex which includes the POSH polypeptide and a POSH-AP. A statistically significant change, such as a decrease, in the formation of the complex in the presence of a test compound (relative to what is seen in the absence of the test compound) is indicative of a modulation, e.g., inhibition, of the interaction between the POSH polypeptide and POSH-AP.

In a further embodiment, the invention provides an assay for identifying a test compound which inhibits or potentiates the interaction of a POSH polypeptide to a POSH-AP, comprising (a) forming a reaction mixture including POSH polypeptide, a POSH-AP; and a test compound; and detecting binding of said POSH polypeptide to said POSH-AP; wherein a change in the binding of said POSH polypeptide to said POSH-AP in the presence of the test compound, relative to binding in the absence of the test compound, indicates that said test compound potentiates or inhibits binding of said POSH polypeptide to said POSH-AP.

In additional embodiment, the invention relates to a method for identifying modulators of protein complexes, comprising (a) forming a reaction mixture comprising a POSH polypeptide, a POSH-AP; and a test compound; (b) contacting the reaction mixture with a test agent, and (c) determining the effect of the test agent for one or more activities. Exemplary activities include a change in the level of the protein complex, a change in the enzymatic activity of the complex, where the reaction mixture is a whole cell, a change in the plasma membrane localization of the complex or a component thereof or a change in the interaction between the POSH polypeptide and the POSH-AP.

An additional embodiment is a screening assay to identify agents that inhibit or potentiate the interaction of a POSH polypeptide and a POSH-AP, comprising providing a two-hybrid assay system including a first fusion protein comprising a POSH polypeptide portion of SEQ ID NO:2, and a second fusion protein comprising a POSH-AP portion, under conditions wherein said two hybrid assay is sensitive to interactions between the POSH polypeptide portion of said first fusion protein and said POSH-AP portion of said second polypeptide; measuring a level of interactions between said fusion proteins in the presence and in the absence of a test agent; and comparing the level of interaction of said fusion proteins, wherein a decrease in the level of interaction is indicative of an agent that will inhibit the interaction between a POSH polypeptide and a POSH-AP.

In additional aspects, the invention provides isolated protein complexes including a combination of a POSH polypeptide and at least one POSH-AP. In certain embodiments, a POSH complex is related to clathrin-coated vesicle formation. In a further embodiment, a POSH complex comprises a viral protein, such as Gag. In certain embodiments, a POSH complex relates to a ubiquitin related activity of POSH, as in the case of POSH complexes comprising ubiquitin (e.g., covalent or non-covalent POSH ubiquitin conjugates), an E2, an E1 or a ubiquitination target.

In an additional aspect, the invention provides nucleic acid therapies for manipulating POSH. In one embodiment, the invention provides a ribonucleic acid comprising between 5 and 1000 consecutive nucleotides of a nucleic acid sequence that is at least 90%, 95%, 98%, 99% or optionally 100% identical to a sequence of SEQ ID NO:1 and/or 3 or a complement thereof. Optionally the ribonucleic acid comprises at least 10, 15, 20, 25, or 30 consecutive nucleotides, and no more than 1000, 750, 500 and 250 consecutive nucleotides of a POSH nucleic acid. In certain embodiments the ribonucleic acid is an RNAi oligomer or a ribozyme. Preferably, the ribonucleic acid decreases the level of a POSH mRNA. Preferred ribonucleic acids comprise a sequence selected from any of SEQ ID Nos: 15, 16, 18, 19, 21, 22, 24 and 25.

The invention also features transgenic non-human animals, e.g. mice, rats, rabbits, goats, sheep, dogs, cats, cows, or non-human primates, having a transgene, e.g., animals which include (and preferably express) a heterologous form of the POSH gene described herein. Such a transgenic animal can serve as an animal model for studying viral infections such as HIV infection or for use in drug screening for viral infections.

In further aspects, the invention provides compositions for the delivery of a nucleic acid therapy, such as, for example, compositions comprising a liposome and/or a pharmaceutically acceptable excipient or carrier.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I-IV (D. M. Weir and C. C. Blackwell, eds., 1986); *Manipulating the Mouse Embryo,* (Cold Spring Harbor Laboratory Press, Cold Spring Harbor, N.Y., 1986).

Other features and advantages of the invention will be apparent from the following detailed description, and from the claims.

BRIEF DESCRIPTION OF THE DRAWINGS

FIG. 1: Human POSH Coding Sequence (SEQ ID NO:1)

FIG. 2: Human POSH Amino Acid Sequence (SEQ ID NO:2)

FIG. 3: Human POSH cDNA Sequence (SEQ ID NO:3)

FIG. 4: 5' cDNA fragment of human POSH (public gi: 10432611; SEQ ID NO:4)

FIG. 5: N terminus protein fragment of hPOSH (public gi:10432612; SEQ ID NO:5)

FIG. 6: 3' mRNA fragment of hPOSH (public gi:7959248; SEQ ID NO:6)

FIG. 7: C terminus protein fragment of hPOSH (public gi:7959249; SEQ ID NO:7)

FIG. 8: Human POSH full mRNA, annotated sequence

FIG. 9: Domain analysis of human POSH

FIG. 14: Mouse POSH mRNA sequence (public gi:10946921; SEQ ID NO: 8)

FIG. 15: Mouse POSH Protein sequence (Public gi: 10946922; SEQ ID NO: 9)

FIG. 16: *Drosophila melanogaster* POSH mRNA sequence (public gi:17737480; SEQ ID NO: 10)

FIG. 17: *Drosophila melanogaster* POSH protein sequence (public gi:17737481; SEQ ID NO:11)

FIG. 18: POSH Domain Analysis

DETAILED DESCRIPTION OF THE INVENTION

1. Definitions

Figure 10:
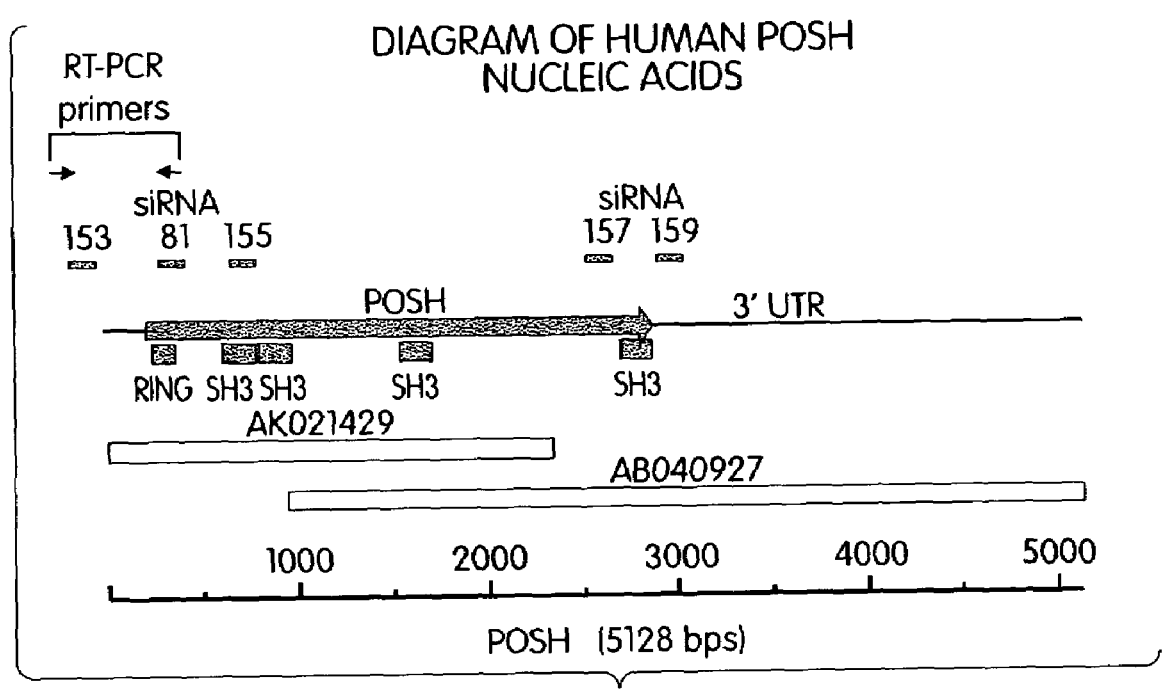
FIG. 10: Diagram of human POSH nucleic acids. The diagram shows the full-length POSH gene and the position of regions amplified by RT-PCR or targeted by siRNA used in FIG. 11.

The term "binding" refers to a direct association between two molecules, due to, for example, covalent, electrostatic, hydrophobic, ionic and/or hydrogen-bond interactions under physiological conditions.

A "chimeric protein" or "fusion protein" is a fusion of a first amino acid sequence encoding a polypeptide with a second amino acid sequence defining a domain foreign to and not substantially homologous with any domain of the first amino acid sequence. A chimeric protein may present a foreign domain which is found (albeit in a different protein) in an organism which also expresses the first protein, or it may be an "interspecies", "intergenic", etc. fusion of protein structures expressed by different kinds of organisms.

The terms "compound", "test compound" and "molecule" are used herein interchangeably and are meant to include, but are not limited to, peptides, nucleic acids, carbohydrates, small organic molecules, natural product extract libraries, and any other molecules (including, but not limited to, chemicals, metals and organometallic compounds).

The phrase "conservative amino acid substitution" refers to grouping of amino acids on the basis of certain common properties. A functional way to define common properties between individual amino acids is to analyze the normalized frequencies of amino acid changes between corresponding proteins of homologous organisms (Schulz, G. E. and R. H. Schirmer., Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer., Principles of Protein Structure, Springer-Verlag). Examples of amino acid groups defined in this manner include:

(i) a charged group, consisting of Glu and Asp, Lys, Arg and His,
(ii) a positively-charged group, consisting of Lys, Arg and His,
(iii) a negatively-charged group, consisting of Glu and Asp,
(iv) an aromatic group, consisting of Phe, Tyr and Trp,
(v) a nitrogen ring group, consisting of His and Trp,
(vi) a large aliphatic nonpolar group, consisting of Val, Leu and Ile,
(vii) a slightly-polar group, consisting of Met and Cys,
(viii) a small-residue group, consisting of Ser, Thr, Asp, Asn, Gly, Ala, Glu, Gln and Pro, (ix) an aliphatic group consisting of Val, Leu, Ile, Met and Cys, and (x) a small hydroxyl group consisting of Ser and Thr.

In addition to the groups presented above, each amino acid residue may form its own group, and the group formed by an individual amino acid may be referred to simply by the one and/or three letter abbreviation for that amino acid commonly used in the art.

A "conserved residue" is an amino acid that is relatively invariant across a range of similar proteins. Often conserved residues will vary only by being replaced with a similar amino acid, as described above for "conservative amino acid substitution".

The term "domain" as used herein refers to a region of a protein that comprises a particular structure and/or performs a particular function.

The term "envelop virus" as used herein refers to any virus that uses cellular membrane and/or any organelle membrane in the viral release process.

"Homology" or "identity" or "similarity" refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated" or "non-homologous" shares less than 40% identity, though preferably less than 25% identity with a sequence of the present invention. In comparing two sequences, the absence of residues (amino acids or nucleic acids) or presence of extra residues also decreases the identity and homology/similarity.

The term "homology" describes a mathematically based comparison of sequence similarities which is used to identify genes or proteins with similar functions or motifs. The nucleic acid and protein sequences of the present invention may be used as a "query sequence" to perform a search against public databases to, for example, identify other family members, related sequences or homologs. Such searches can be performed using the NBLAST and XBLAST programs (version 2.0) of Altschul, et al. (1990) J Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and BLAST) can be used. See http://www.ncbi.nlm.nih.gov.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids, Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well known Smith Waterman algorithm may also be used to determine identity.

The term "intron" refers to a portion of nucleic acid that is intially transcribed into RNA but later removed such that it is not, for the most part, represented in the processed mRNA. Intron removal occurs through reactions at the 5' and 3' ends, typically referred to as 5' and 3' splice sites, respectively. Alternate use of different splice sites results in splice variants. An intron is not necessarily situated between two "exons", or portions that code for amino acids, but may instead be positioned, for example, between the promoter and the first exon. An intron may be self-splicing or may require cellular components to be spliced out of the mRNA. A "heterologous intron" is an intron that is inserted into a coding sequence that is not naturally associated with that coding sequence. In addition, a heterologous intron may be a genrally natural intron wherein one or both of the splice sites have been altered to provide a desired quality, such as increased or descreased splice efficiency. Heterologous introns are often inserted, for example, to improve expression of a gene in a heterologous host, or to increase the production of one splice variant relative to another. As an example, the rabbit beta-globin gene may be used, and is commercially available on the pCI vector from Promega Inc. Other exemplary introns are provided in Lacy-Hulbert et al. (2001) Gene Ther 8(8):649-53.

The term "isolated", as used herein with reference to the subject proteins and protein complexes, refers to a preparation of protein or protein complex that is essentially free from contaminating proteins that normally would be present with the protein or complex, e.g., in the cellular milieu in which the protein or complex is found endogenously. Thus, an isolated protein complex is isolated from cellular components that normally would "contaminate" or interfere with the study of the complex in isolation, for instance while screening for modulators thereof. It is to be understood, however, that such an "isolated" complex may incorporate other proteins the modulation of which, by the subject protein or protein complex, is being investigated.

The term "isolated" as also used herein with respect to nucleic acids, such as DNA or RNA, refers to molecules in a form which does not occur in nature. Moreover, an "isolated nucleic acid" is meant to include nucleic acid fragments which are not naturally occurring as fragments and would not be found in the natural state.

Lentiviruses include primate lentiviruses, e.g., human immunodeficiency virus types 1 and 2 (HIV-1/HIV-2); simian immunodeficiency virus (SIV) from Chimpanzee (SIVcpz), Sooty mangabey (SIVsmm), African Green Monkey (SIVagm), Syke's monkey (SIVsyk), Mandrill (SIVmnd) and Macaque (SIVmac). Lentiviruses also include feline lentiviruses, e.g., Feline immunodeficiency virus (FIV); Bovine lentiviruses, e.g., Bovine immunodeficiency virus (BIV); Ovine lentiviruses, e.g., Maedi/Visna virus (MVV) and Caprine arthritis encephalitis virus (CAEV); and Equine lentiviruses, e.g., Equine infectious anemia virus (EIAV). All lentiviruses express at least two additional regulatory proteins (Tat, Rev) in addition to Gag, Pol, and Env proteins. Primate lentiviruses produce other accessory proteins including Nef, Vpr, Vpu, Vpx, and Vif. Generally, lentiviruses are the causative agents of a variety of disease, including, in addition to immunodeficiency, neurological degeneration, and arthritis. Nucleotide sequences of the various lentiviruses can be found in Genbank under the following Accession Nos. (from J. M. Coffin, S. H. Hughes, and H. E. Varmus, "Retroviruses" Cold Spring Harbor Laboratory Press, 199,7 p 804): 1) HIV-1: K03455, M19921, K02013, M3843 1, M38429, K02007 and M174 2) HIV-2: M30502, J04542, M30895, J04498, M15390, M31113 and L07625; 3) SIV:M29975, M30931, M58410, M66437, L06042, M33262, M19499, M32741, M31345 and L03295; 4) FIV: M25381, M36968 and U1 1820; 5)BIV. M32690; 6)E1AV: M16575, M87581 and U01866; 6)Visna: M10608, M51543, L06906, M60609 and M60610; 7) CAEV: M33677; and 8) Ovine lentivirus M31646 and M34193. Lentiviral DNA can also be obtained from the American Type Culture Collection (ATCC). For example, feline immunodeficiency virus is available under ATCC Designation No. VR-2333 and VR-3112. Equine infectious anemia virus A is available under ATCC Designation No. VR-778. Caprine arthritis-encephalitis virus is available under ATCC Designation No. VR-905. Visna virus is available under ATCC Designation No. VR-779.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

The term "maturation" as used herein refers to the production, post-translational processing, assembly and/or release of proteins that form a viral particle. Accordingly, this includes the processing of viral proteins leading to the pinching off of nascent virion from the cell membrane.

A "membrane associated protein" is meant to include proteins that are integral membrane proteins as well as proteins that are stably associated with a membrane.

The term "p6" or "p6gag" is used herein to refer to a protein comprising a viral L domain. Antibodies that bind to a p6 domain are referred to as "anti-p6 antibodies". p6 also refers to proteins that comprise artificially engineered L domains including, for example, L domains comprising a series of L motifs. The term "Gag protein" or "Gag polypeptide" refers to a polypeptide having Gag activity and preferably comprising an L (or late) domain. Exemplary Gag proteins include a motif such as PXXP, PPXY, RXXPXXP, RPDPTAP (SEQ ID NO: 36), RPLPVAP (SEQ ID NO: 37), RPEPTAP (SEQ ID NO: 38), YEDL (SEQ ID NO: 39), PTAPPEY (SEQ ID NO: 40) and/or RPEPTAPPEE (SEQ ID NO: 41). HIV p24 is an exemplary Gag polypeptide.

A "POSH nucleic acid" is a nucleic acid comprising a sequence as represented in any of SEQ ID Nos:1, 3, 4, 6, 8, and 10 as well as any of the variants described herein.

A "POSH polypeptide" or "POSH protein" is a polypeptide comprising a sequence as represented in any of SEQ ID Nos: 2, 5, 7, 9 and 11 as well as any of the variations described herein.

A "POSH-associated protein" or "POSH-AP" refers to a protein capable of interacting with and/or binding to a POSH polypeptide. Generally, the POSH-AP may interact directly or indirectly with the POSH polypeptide. Exemplary POSH-APs are provided throughout.

The terms peptides, proteins and polypeptides are used interchangeably herein.

The term "purified protein" refers to a preparation of a protein or proteins which are preferably isolated from, or otherwise substantially free of, other proteins normally associated with the protein(s) in a cell or cell lysate. The term "substantially free of other cellular proteins" (also referred to herein as "substantially free of other contaminating proteins") is defined as encompassing individual preparations of each of the component proteins comprising less than 20% (by dry weight) contaminating protein, and preferably comprises less than 5% contaminating protein. Functional forms of each of the component proteins can be prepared as purified preparations by using a cloned gene as described in the attached examples. By "purified", it is meant, when referring to component protein preparations used to generate a reconstituted protein mixture, that the indicated molecule is present in the substantial absence of other biological macromolecules, such as other proteins (particularly other proteins which may substantially mask, diminish, confuse or alter the characteristics of the component proteins either as purified preparations or in their function in the subject reconstituted mixture). The term "purified" as used herein preferably means at least 80% by dry weight, more preferably in the range of 85% by weight, more preferably 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above.

A "receptor" or "protein having a receptor function" is a protein that interacts with an extracellular ligand or a ligand that is within the cell but in a space that is topologically equivalent to the extracellular space (eg. inside the Golgi, inside the endoplasmic reticulum, inside the nuclear membrane, inside a lysosome or transport vesicle, etc.). Exemplary receptors are identified herein by annotation as such in various public databases. Receptors often have membrane domains.

A "recombinant nucleic acid" is any nucleic acid that has been placed adjacent to another nucleic acid by recombinant DNA techniques. A "recombined nucleic acid" also includes any nucleic acid that has been placed next to a second nucleic acid by a laboratory genetic technique such as, for example, tranformation and integration, transposon hopping or viral insertion. In general, a recombined nucleic acid is not naturally located adjacent to the second nucleic acid.

The term "recombinant protein" refers to a protein of the present invention which is produced by recombinant DNA techniques, wherein generally DNA encoding the expressed protein is inserted into a suitable expression vector which is in turn used to transform a host cell to produce the heterologous protein. Moreover, the phrase "derived from", with respect to a recombinant gene encoding the recombinant protein is meant to include within the meaning of "recombinant protein" those proteins having an amino acid sequence of a native protein, or an amino acid sequence similar thereto which is generated by mutations including substitutions and deletions of a naturally occurring protein.

A "RING domain" or "Ring Finger" is a zinc-binding domain with a defined octet of cysteine and histidine residues. Certain RING domains comprise the consensus sequences as set forth below (amino acid nomenclature is as set forth in Table 1): Cys Xaa Xaa Cys $Xaa_{10-20}$ Cys Xaa His $Xaa_{2-5}$ Cys Xaa Xaa Cys $Xaa1_{13-50}$ Cys Xaa Xaa Cys or Cys Xaa Xaa Cys $Xaa_{10-20}$ Cys Xaa His $Xaa_{2-5}$ His Xaa Xaa Cys $Xaa_{13-50}$ Cys Xaa Xaa Cys. Certain RING domains are represented as amino acid sequences that are at least 80% identical to amino acids 12-52 of SEQ ID NO: 2 and is set forth in SEQ ID No: 26. Preferred RING domains are 85%, 90%, 95%, 98% and, most preferably, 100% identical to the amino acid sequence of SEQ ID NO: 26. Preferred RING domains of the invention bind to various protein partners to form a complex that has ubiquitin ligase activity. RING domains preferably interact with at least one of the following protein types: F box proteins, E2 ubiquitin conjugating enzymes and cullins.

The term "RNA interference" or "RNAi" refers to any method by which expression of a gene or gene product is decreased by introducing into a target cell one or more double-stranded RNAs which are homologous to the gene of interest (particularly to the messenger RNA of the gene of interest).

"Small molecule" as used herein, is meant to refer to a composition, which has a molecular weight of less than about 5 kD and most preferably less than about 2.5 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures comprising arrays of small molecules, often fungal, bacterial, or algal extracts, which can be screened with any of the assays of the invention.

An "SH3" or "Src Homology 3" domain is a protein domain of generally about 60 amino acid residues first identified as a conserved sequence in the non-catalytic part of several cytoplasmic protein tyrosine kinases (e.g. Src, Abl, Lck). SH3 domains mediate assembly of specific protein complexes via binding to proline-rich peptides. Exemplary SH3 domains are represented by amino acids 137-192, 199-258, 448-505 and 832-888 of SEQ ID NO:2 and are set forth in SEQ ID Nos: 27-30. In certain embodiments, an SH3 domain interacts with a consensus sequence of RXaaXaaPXaaX6P (where X6, as defined in table 1 below, is a hydrophobic amino acid). In certain embodiments, an SH3 domain interacts with one or more of the following sequences: P(T/S)AP (SEQ ID NO: 42), PFRDY (SEQ ID NO: 43), RPEPTAP (SEQ ID NO: 38), RQGPKEP (SEQ ID NO: 44), RQGPKEPFR (SEQ ID NO: 45), RPEPTAPEE (SEQ ID NO: 46) and RPLPVAP (SEQ ID NO: 37).

As used herein, the term "specifically hybridizes" refers to the ability of a nucleic acid probe/primer of the invention to hybridize to at least 12, 15, 20, 25, 30, 35, 40, 45, 50 or 100 consecutive nucleotides of a POSH sequence, or a sequence complementary thereto, or naturally occurring mutants thereof, such that it has less than 15%, preferably less than 10%, and more preferably less than 5% background hybridization to a cellular nucleic acid (e.g., mRNA or genomic DNA) other than the POSH gene. A variety of hybridization conditions may be used to detect specific hybridization, and the stringency is determined primarily by the wash stage of the hybridization assay. Generally high temperatures and low salt concentrations give high stringency, while low temperatures and high salt concentrations give low stringency. Low stringency hybridization is achieved by washing in, for example, about 2.0×SSC at 50° C., and high stringency is acheived with about 0.2×SSC at 50° C. Further descriptions of stringency are provided below.

As applied to polypeptides, "substantial sequence identity" means that two peptide sequences, when optimally aligned, such as by the programs GAP or BESTFIT using default gap which share at least 90 percent sequence identity, preferably at least 95 percent sequence identity, more preferably at least 99 percent sequence identity or more. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant protein gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the protein.

As used herein, a "transgenic animal" is any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant human POSH protein. The "non-human animals" of the invention include vertebrates such as rodents, non-human primates, sheep, dog, cow, chickens, amphibians, reptiles, etc. Preferred non-human animals are selected from the rodent family including rat and mouse, most preferably mouse, though transgenic amphibians, such as members of the *Xenopus* genus, and transgenic chickens can also provide important tools for understanding and identifying agents which can affect, for example, embryogenesis and tissue formation. The term "chimeric animal" is used herein to refer to animals in which the recombinant gene is found, or in which the recombinant is expressed in some but not all cells of the animal. The term "tissue specific chimeric animal" indicates that the recombinant human POSH genes is present and/or expressed in some tissues but not others.

As used herein, the term "transgene" means a nucleic acid sequence (encoding, e.g., human POSH polypeptides), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity.

A "virion" is a complete viral particle; nucleic acid and capsid (and a lipid envelope in some viruses.

TABLE 1

Abbreviations for classes of amino acids*

| Symbol | Category | Amino Acids Represented |
|---|---|---|
| X1 | Alcohol | Ser, Thr |
| X2 | Aliphatic | Ile, Leu, Val |
| Xaa | Any | Ala, Cys, Asp, Glu, Phe, Gly, His, Ile, Lys, Leu, Met, Asn, Pro, Gln, Arg, Ser, Thr, Val, Trp, Tyr |
| X4 | Aromatic | Phe, His, Trp, Tyr |
| X5 | Charged | Asp, Glu, His, Lys, Arg |
| X6 | Hydrophobic | Ala, Cys, Phe, Gly, His, Ile, Lys, Leu, Met, Thr, Val, Trp, Tyr |
| X7 | Negative | Asp, Glu |
| X8 | Polar | Cys, Asp, Glu, His, Lys, Asn, Gln, Arg, Ser, Thr |
| X9 | Positive | His, Lys, Arg |
| X10 | Small | Ala, Cys, Asp, Gly, Asn, Pro, Ser, Thr, Val |
| X11 | Tiny | Ala, Gly, Ser |
| X12 | Turnlike | Ala, Cys, Asp, Glu, Gly, His, Lys, Asn, Gln, Arg, Ser, Thr |
| X13 | Asparagine-Aspartate | Asn, Asp |

*Abbreviations as adopted from http://smart.embl-heidelberg.de/SMART_DATA/alignments/consensus/grouping.html.

2. Overview

In certain aspects, the invention relates to novel human POSH nucleic acids and proteins, and related methods and compositions. In certain aspects, the invention relates to novel associations between certain disease states and POSH nucleic acids and proteins. POSH intersects with and regulates a wide range of key cellular functions that may be manipulated by affecting the level of and/or activity of POSH polypeptides. In certain aspects, by identifying the human POSH gene the present invention provides methods for identifying diseases that are associated with defects in the POSH gene and methods for ameliorating such diseases. In further aspects, the invention provides nucleic acid agents (e.g. RNAi probes, antisense), antibody-related agents, small molecules and other agents that affect POSH function. In further aspects, the invention provides methods for identifying agents that affect POSH function, and the function of proteins that associate with POSH and/or participate in a POSH mediated process. Other aspects and embodiments are described herein.

In certain aspects, the invention relates to the discovery that certain POSH polypeptides function as E3 enzymes in the ubiquitination system. Accordingly, downregulation or upregulation of POSH ubiquitin ligase activity can be used to manipulate biological processes that are affected by protein ubiquitination. Downregulation or upregulation may be achieved at any stage of POSH formation and regulation, including transcriptional, translational or post-translational regulation. For example, POSH transcript levels may be decreased by RNAi targeted at a POSH gene sequence. As another example, POSH ubiquitin ligase activity may be inhibited by contacting POSH with an antibody that binds to and interferes with a POSH RING domain or a domain of POSH that mediates interaction with a target protein (a protein that is ubiquitinated at least in part because of POSH activity). As another example, POSH activity may be increased by causing increased expression of POSH or an active portion thereof. A ubiquitin ligase, such as POSH, may participate in biological processes including, for example, one or more of the various stages of a viral lifecycle, such as viral entry into a cell, production of viral proteins, assembly of viral proteins and release of viral particles from the cell. POSH may participate in diseases characterized by the accumulation of ubiquitinated proteins, such as dementias (e.g. Alzheimer's and Pick's), inclusion body myositis and myopathies, polyglucosan body myopathy, and certain forms of amyotrophic lateral sclerosis. POSH may participate in diseases characterized by the excessive or inappropriate ubiquitination and/or protein degradation. In addition, POSH may participate in oncological processes, such as the failure of cell division control systems, the failure of cell death regulatory systems, and the failure to downregulate hyperactive oncogenes, such as hyperactive membrane-bound growth factor receptors. By identifying certain POSH polypeptides as ubiquitin ligases, aspects of the present invention permit one of ordinary skill in the art to identify diseases that are associated with an altered POSH ubiquitin ligase activity.

In certain aspects, the invention relates to the discovery that certain POSH polypeptides are involved in viral maturation, including the production, post-translational processing, assembly and/or release of proteins in a viral particle. Accordingly, viral infections may be ameliorated by inhibiting an activity (e.g. ubiquitin ligase activity or target protein interaction) of POSH, and in preferred embodiments, the virus is a retroid virus, an RNA virus and an envelop virus, including HIV, Ebola, HBV, HCV and HTLV. Additional viral species are described in greater detail below. In certain instances, a decrease of a POSH function is lethal to cells infected with a virus that employs POSH in release of viral particles. While not wishing to be bound to mechanism, it appears that loss of POSH function in such cells leads to cell death through an overaccumulation of viral particles, or portions thereof, in a the cell. In certain embodiments, the inhibition of a POSH activity, e.g. by siRNA knockdown may be used to destroy infected cells, even cells with nearly latent virus, because such cells will die from eventual overaccumulation of viral particles or portions thereof.

In certain aspects, the invention relates to the discovery that hPOSH interacts with Rac, a small GTPase. Rho, Rac and Cdc42 operate together to regulate organization of the actin cytoskeleton and the JNK MAP kinase pathway.

Ectopic expression of mouse POSH ("mPOSH") activates the JNK pathway and causes nuclear localization of NF-κB. Overexpression of mPOSH in fibroblasts stimulates apoptosis. (Tapon et al. (1998) EMBO J. 17:1395-404). In *Drosophila*, POSH may interact, or otherwise influence the signaling of, another GTPase, Ras. (Schnorr et al. (2001) Genetics 159: 609-22). The JNK pathway and NF-κB regulate a variety of key genes involved in, for example, immune responses, inflammation, cell proliferation and apoptosis. For example, NF-κB regulates the production of interleukin 1, interleukin 8, tumor necrosis factor and many cell adhesion molecules. NF-κB has both pro-apoptotic and anti-apoptotic roles in the cell (e.g. in FAS-induced cell death and TNF-alpha signaling, respectively). NF-κB is negatively regulated, in part, by the inhibitor proteins IκBα and IκBβ (collectively termed "IκB"). Phosphorylation of IκB permits activation and nuclear localization of NF-κB. Phosphorylation of IκB triggers its degradation by the ubiquitin system. Accordingly, in yet another embodiment, a POSH polypeptide stimulates the JNK pathway. In an additional embodiment, a POSH polypeptide promotes nuclear localization of NF-κB. In further embodiments, manipulation of POSH levels and/or activities may be used to manipulate apoptosis. By upregulating POSH, apoptosis may be stimulated in certain cells, and this will generally be desirable in conditions characterized by excessive cell proliferation (e.g. in certain cancers). By downregulating POSH, apoptosis may be diminished in certain cells, and this will generally be desirable in conditions characterized by excessive cell death, such as myocardial infarction, stroke, degenerative diseases of muscle and nerve, and for organ preservation prior to transplant. In a further embodiment, a POSH polypeptide associates with a vesicular trafficking complex, such as a clathrin- or coatomer-containing complex, and particularly a trafficking complex that localizes to the nucleus and/or Golgi apparatus.

3. Exemplary Nucleic Acids and Expression Vectors

In certain aspects the invention provides nucleic acids encoding POSH polypeptides, such as, for example, SEQ ID Nos: 2, 5, 7, 9, 11, 26, 27, 28, 29 and 30. Nucleic acids of the invention are further understood to include nucleic acids that comprise variants of SEQ ID Nos:1, 3, 4, 6, 8, 10, 31, 32, 33, 34, and 35. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID Nos:1, 3, 4, 6, 8 10, 31, 32, 33, 34, and 35, e.g., due to the degeneracy of the genetic code. In other embodiments, variants will also include sequences that will hybridize under highly stringent conditions to a nucleotide sequence of a coding sequence designated in any of SEQ ID Nos:1, 3, 4, 6, 8 10, 31, 32, 33, 34, and 35. Preferred nucleic acids of the invention are human POSH sequences, including, for example, any of SEQ ID Nos: 1, 3, 4, 6, 31, 32, 33, 34, 35 and variants thereof and nucleic acids encoding an amino acid sequence selected from among SEQ ID Nos: 2, 5, 7, 26, 27, 28, 29 and 30.

One of ordinary skill in the art will understand readily that appropriate stringency conditions which promote DNA hybridization can be varied. For example, one could perform the hybridization at 6.0×sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from SEQ ID Nos:1, 3, 4, 6, 8, 10, 31, 32, 33, 34, and 35 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

Optionally, a POSH nucleic acid of the invention will genetically complement a partial or complete POSH loss of function phenotype in a cell. For example, a POSH nucleic acid of the invention may be expressed in a cell in which endogenous POSH has been reduced by RNAi, and the introduced POSH nucleic acid will mitigate a phenotype resulting from the RNAi. An exemplary POSH loss of function phenotype is a decrease in virus-like particle production in a cell transfected with a viral vector, optionally an HIV vector. In certain embodiments, a POSH nucleic acid, when expressed at an effective level in a cell, induces apoptosis.

Another aspect of the invention relates to POSH nucleic acids that are used for antisense, RNAi or ribozymes. As used herein, nucleic acid therapy refers to administration or in situ generation of a nucleic acid or a derivative thereof which specifically hybridizes (e.g. binds) under cellular conditions with the cellular mRNA and/or genomic DNA encoding one of the subject POSH polypeptides so as to inhibit production of that protein, e.g. by inhibiting transcription and/or translation. The binding may be by conventional base pair complementarity, or, for example, in the case of binding to DNA duplexes, through specific interactions in the major groove of the double helix.

An nucleic acid therapy construct of the present invention can be delivered, for example, as an expression plasmid which, when transcribed in the cell, produces RNA which is complementary to at least a unique portion of the cellular mRNA which encodes a POSH polypeptide. Alternatively, the the construct is an oligonucleotide which is generated ex vivo and which, when introduced into the cell causes inhibition of expression by hybridizing with the mRNA and/or genomic sequences encoding a POSH polypeptide. Such oligonucleotide probes are optionally modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in nucleic acid therapy have been reviewed, for example, by van der Krol et al., (1988) *Biotechniques* 6:958-976; and Stein et al., (1988) *Cancer Res* 48:2659-2668.

Accordingly, the modified oligomers of the invention are useful in therapeutic, diagnostic, and research contexts. In therapeutic applications, the oligomers are utilized in a manner appropriate for nucleic acid therapy in general.

In addition to use in therapy, the oligomers of the invention may be used as diagnostic reagents to detect the presence or absence of the POSH DNA or RNA sequences to which they specifically bind, such as for determining the level of expression of a gene of the invention or for determining whether a gene of the invention contains a genetic lesion.

In another aspect of the invention, the subject nucleic acid is provided in an expression vector comprising a nucleotide sequence encoding a subject POSH polypeptide and operably linked to at least one regulatory sequence. Regulatory sequences are art-recognized and are selected to direct expression of the POSH polypeptide. Accordingly, the term regulatory sequence includes promoters, enhancers and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a POSH polypeptide. Such useful expression control sequences, include, for example, the early and late promoters of SV40, tet promoter, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

As will be apparent, the subject gene constructs can be used to cause expression of the subject POSH polypeptides in cells propagated in culture, e.g. to produce proteins or polypeptides, including fusion proteins or polypeptides, for purification.

This invention also pertains to a host cell transfected with a recombinant gene including a coding sequence for one or more of the subject POSH polypeptides. The host cell may be any prokaryotic or eukaryotic cell. For example, a polypeptide of the present invention may be expressed in bacterial cells such as *E. coli*, insect cells (e.g., using a baculovirus expression system), yeast, or mammalian cells. Other suitable host cells are known to those skilled in the art.

Accordingly, the present invention further pertains to methods of producing the subject POSH polypeptides. For example, a host cell transfected with an expression vector encoding a POSH polypeptide can be cultured under appropriate conditions to allow expression of the polypeptide to occur. The polypeptide may be secreted and isolated from a mixture of cells and medium containing the polypeptide. Alternatively, the polypeptide may be retained cytoplasmically and the cells harvested, lysed and the protein isolated. A cell culture includes host cells, media and other byproducts. Suitable media for cell culture are well known in the art. The polypeptide can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the polypeptide. In a preferred embodiment, the POSH polypeptide is a fusion protein containing a domain which facilitates its purification, such as a POSH-GST fusion protein, POSH-intein fusion protein, POSH-cellulose binding domain fusion protein, POSH-polyhistidine fusion protein etc.

A nucleotide sequence encoding a POSH polypeptide can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial) cells, are standard procedures.

A recombinant POSH nucleic acid can be produced by ligating the cloned gene, or a portion thereof, into a vector suitable for expression in either prokaryotic cells, eukaryotic cells, or both. Expression vehicles for production of a recombinant POSH polypeptides include plasmids and other vectors. For instance, suitable vectors for the expression of a POSH polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP 17 are cloning and expression vehicles useful in the introduction of genetic constructs into *S. cerevisiae* (see, for example, Broach et al., (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant POSH polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

It is well known in the art that a methionine at the N-terminal position can be enzymatically cleaved by the use of the enzyme methionine aminopeptidase (MAP). MAP has been cloned from *E. coli* (Ben-Bassat et al., (1987) *J. Bacteriol.* 169:751-757) and *Salmonella typhimurium* and its in vitro activity has been demonstrated on recombinant proteins (Miller et al., (1987) *PNAS USA* 84:2718-1722). Therefore, removal of an N-terminal methionine, if desired, can be achieved either in vivo by expressing such recombinant polypeptides in a host which produces MAP (e.g., *E. coli* or CM89 or *S. cerevisiae*), or in vitro by use of purified MAP (e.g., procedure of Miller et al.).

Alternatively, the coding sequences for the polypeptide can be incorporated as a part of a fusion gene including a nucleotide sequence encoding a different polypeptide. This type of expression system can be useful under conditions where it is desirable, e.g., to produce an immunogenic fragment of a POSH polypeptide. For example, the VP6 capsid protein of rotavirus can be used as an immunologic carrier protein for portions of polypeptide, either in the monomeric form or in the form of a viral particle. The nucleic acid sequences corresponding to the portion of the POSH polypeptide to which antibodies are to be raised can be incorporated into a fusion gene construct which includes coding sequences for a late vaccinia virus structural protein to produce a set of recombinant viruses expressing fusion proteins comprising a portion of the protein as part of the virion. The Hepatitis B surface antigen can also be utilized in this role as well. Similarly, chimeric constructs coding for fusion proteins containing a portion of a POSH polypeptide and the poliovirus capsid protein can be created to enhance immunogenicity (see, for example, EP Publication NO: 0259149; and Evans et al., (1989) *Nature* 339:385; Huang et al., (1988) *J Virol.* 62:3855; and Schlienger et al., (1992) *J. Virol* 66:2).

The Multiple Antigen Peptide system for peptide-based immunization can be utilized, wherein a desired portion of a POSH polypeptide is obtained directly from organo-chemical synthesis of the peptide onto an oligomeric branching lysine core (see, for example, Posnett et al., (1988) *JBC* 263:1719 and Nardelli et al., (1992) *J. Immunol.* 148:914). Antigenic determinants of a POSH polypeptide can also be expressed and presented by bacterial cells.

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a Ni$^{2+}$ metal resin. The purification leader sequence can then be subsequently removed by treatment with enterokinase to provide the purified POSH polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

TABLE 2

Exemplary POSH nucleic acids

| Sequence Name | Organism | Accession Number |
|---|---|---|
| cDNA FLJ11367 fis, clone HEMBA1000303 | *Homo sapiens* | AK021429 |
| Plenty of SH3 domains (POSH) mRNA | *Mus musculus* | NM_021506 |
| Plenty of SH3s (POSH) mRNA | *Mus musculus* | AF030131 |
| Plenty of SH3s (POSH) mRNA | *Drosophila melanogaster* | NM_079052 |
| Plenty of SH3s (POSH) mRNA | *Drosophila melanogaster* | AF220364 |

TABLE 3

Exemplary POSH polypeptides

| Sequence Name | Organism | Accession Number |
|---|---|---|
| SH3 domains-containing protein POSH | *Mus musculus* | T09071 |
| plenty of SH3 domains | *Mus musculus* | NP_067481 |
| Plenty of SH3s; POSH | *Mus musculus* | AAC40070 |
| Plenty of SH3s | *Drosophila melanogaster* | AAF37265 |
| LD45365p | *Drosophila melanogaster* | AAK93408 |
| POSH gene product | *Drosophila melanogaster* | AAF57833 |
| Plenty of SH3s | *Drosophila melanogaster* | NP_523776 |

In addition the following Tables provide the nucleic acid sequence and related SEQ ID NOs for domains of human POSH protein and a summary of sequence identification numbers used in this application.

TABLE 4

Nucleic Acid Sequences and related SEQ ID NOs for domains in human POSH

| Name of the sequence | Sequence | SEQ ID NO |
|---|---|---|
| RING domain | TGTCCGGTGTGTCTAGAGCGCCTTGATGCTTCTGCGAAGGTCTTGCCTTGCCAGCATACGTTTT GCAAGCGATGTTTGCT GGGGATCGTAGGTTCTCGAAATGAACTCAGATGTCCCGAGT | 31 |

TABLE 4-continued

Nucleic Acid Sequences and related SEQ ID NOs for domains in human POSH

| Name of the sequence | Sequence | SEQ ID NO |
|---|---|---|
| 1st SH3 domain | CCATGTGCCAAAGCGTTATACAACTATGAAGGAAAAGAGCCTGGAGACCTTAAATTCAGCAAAG GCGACATCATCATTTT GCGAAGACAAGTGGATGAAAATTGGTACCATGGGGAAGTCAATGGAATCCATGGCTTTTTCCCC ACCAACTTTGTGCAGA TTATT | 32 |
| 2nd SH3 domain | CCTCAGTGCAAAGCACTTTATGACTTTGAAGTGAAAGACAAGGAAGCAGACAAAGATTGCCTTC CATTTGCAAAGGATGA TGTTCTGACTGTGATCCGAAGAGTGGATGAAAACTGGGCTGAAGGAATGCTGGCAGACAAAATA GGAATATTTCCAATTT CATATGTTGAGTTTAAC | 33 |
| 3rd SH3 domain | AGTGTGTATGTTGCTATATATCCATACACTCCTCGGAAAGAGGATGAACTAGAGCTGAGAAAAG GGGAGATGTTTTTAGT GTTTGAGCGCTGCCAGGATGGCTGGTTCAAAGGGACATCCATGCATACCAGCAAGATAGGGGTT TTCCCTGGCAATTATG TGGCACCAGTC | 34 |
| 4th SH3 domain | GAAAGGCACAGGGTGGTGGTTTCCTATCCTCCTCAGAGTGAGGCAGAACTTGAACTTAAAGAAG GAGATATTGTGTTTGT TCATAAAAAACGAGAGGATGGCTGGTTCAAAGGCACATTACAACGTAATGGGAAAACTGGCCTT TTCCCAGGAAGCTTTG TGGAAAACA | 35 |

TABLE 5

Summary of Sequence Identification Numbers

| Sequence Information | Sequence Identification Number (SEQ ID NO) |
|---|---|
| Human POSH Coding Sequence | SEQ ID No: 1 |
| Human POSH Amino Acid Sequence | SEQ ID No: 2 |
| Human POSH cDNA Sequence | SEQ ID No: 3 |
| 5' cDNA Fragment of Human POSH | SEQ ID No: 4 |
| N-terminus Protein Fragment of Human POSH | SEQ ID No: 5 |
| 3' mRNA Fragment of Human POSH | SEQ ID No: 6 |
| C-terminus Protein Fragment of Human POSH | SEQ ID No: 7 |
| Mouse POSH mRNA Sequence | SEQ ID No: 8 |
| Mouse POSH Protein Sequence | SEQ ID No: 9 |
| Drosophila melanogaster POSH mRNA Sequence | SEQ ID No: 10 |
| Drosophila melanogaster POSH Protein Sequence | SEQ ID No: 11 |
| Human POSH RING Domain Amino Acid Sequence | SEQ ID No: 26 |
| Human POSH 1st SH3 Domain Amino Acid Sequence | SEQ ID No: 27 |
| Human POSH 2nd SH3 Domain Amino Acid Sequence | SEQ ID No: 28 |
| Human POSH 3rd SH3 Domain Amino Acid Sequence | SEQ ID No: 29 |
| Human POSH 4th SH3 Domain Amino Acid Sequence | SEQ ID No: 30 |
| Human POSH RING Domain Nucleic Acid Sequence | SEQ ID No: 31 |
| Human POSH 1st SH3 Domain Nucleic Acid Sequence | SEQ ID No: 32 |
| Human POSH 2nd SH3 Domain Nucleic Acid Sequence | SEQ ID No: 33 |
| Human POSH 3rd SH3 Domain Nucleic Acid Sequence | SEQ ID No: 34 |
| Human POSH 4th SH3 Domain Nucleic Acid Sequence | SEQ ID No: 35 |

4. Exemplary Polypeptides

The present invention also makes available isolated and/or purified forms of the subject POSH polypeptides, which are isolated from, or otherwise substantially free of, other intracellular proteins which might normally be associated with the protein or a particular complex including the protein. In certain embodiments, POSH polypeptides have an amino acid sequence that is at least 60% identical to an amino acid sequence as set forth in any of SEQ ID Nos: 2, 5, 7, 9, 11, 26, 27, 28, 29 and 30. In other embodiments, the polypeptide has an amino acid sequence at least 65%, 70%, 75%, 80%, 85%, 90%, 95%, 97%, 98%, 99% or 100% identical to an amino acid sequence as set forth in any of SEQ ID Nos: 2, 5, 7, 9, 11, 26, 27, 28, 29 and 30.

Optionally, a POSH polypeptide of the invention will function in place of an endogenous POSH polypeptide, for example by mitigating a partial or complete POSH loss of function phenotype in a cell. For example, a POSH polypeptide of the invention may be produced in a cell in which endogenous POSH has been reduced by RNAi, and the introduced POSH polypeptide will mitigate a phenotype resulting from the RNAi. An exemplary POSH loss of function phenotype is a decrease in virus-like particle production in a cell transfected with a viral vector, optionally an HIV vector. In certain embodiments, a POSH polypeptide, when produced at an effective level in a cell, induces apoptosis.

In certain embodiments, a POSH polypeptide of the invention interacts with a viral Gag protein through one or more SH3 domain. In additional embodiments, POSH polypeptides may also, or alternatively, function in ubiquitylation in part through the activity of a RING domain.

In another aspect, the invention provides polypeptides that are agonists or antagonists of a POSH polypeptide. Variants and fragments of a POSH polypeptide may have a hyperactive or constitutive activity, or, alternatively, act to prevent POSH polypeptides from performing one or more functions. For example, a truncated form lacking one or more domain may have a dominant negative effect.

Another aspect of the invention relates to polypeptides derived from a full-length POSH polypeptide. Isolated peptidyl portions of the subject proteins can be obtained by screening polypeptides recombinantly produced from the corresponding fragment of the nucleic acid encoding such polypeptides. In addition, fragments can be chemically synthesized using techniques known in the art such as conventional Merrifield solid phase f-Moc or t-Boc chemistry. For example, any one of the subject proteins can be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of the formation of a specific protein complex, or more generally of a POSH complex, such as by microinjection assays.

It is also possible to modify the structure of the subject POSH polypeptides for such purposes as enhancing therapeutic or prophylactic efficacy, or stability (e.g., ex vivo shelf life and resistance to proteolytic degradation in vivo). Such modified polypeptides, when designed to retain at least one activity of the naturally-occurring form of the protein, are considered functional equivalents of the POSH polypeptides described in more detail herein. Such modified polypeptides can be produced, for instance, by amino acid substitution, deletion, or addition.

For instance, it is reasonable to expect, for example, that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed., Ed. by L. Stryer, W. H. Freeman and Co., 1981). Whether a change in the amino acid sequence of a polypeptide results in a functional homolog can be readily determined by assessing the ability of the variant polypeptide to produce a response in cells in a fashion similar to the wild-type protein. For instance, such variant forms of a POSH polypeptide can be assessed, e.g., for their ability to bind to another polypeptide, e.g., another POSH polypeptide or another protein involved in viral maturation. Polypeptides in which more than one replacement has taken place can readily be tested in the same manner.

This invention further contemplates a method of generating sets of combinatorial mutants of the subject POSH polypeptides, as well as truncation mutants, and is especially useful for identifying potential variant sequences (e.g. homologs) that are functional in binding to a POSH polypeptide. The purpose of screening such combinatorial libraries is to generate, for example, POSH homologs which can act as either agonists or antagonist, or alternatively, which possess novel activities all together. Combinatorially-derived homologs can be generated which have a selective potency relative to a naturally occurring POSH polypeptide. Such proteins, when expressed from recombinant DNA constructs, can be used in gene therapy protocols.

Likewise, mutagenesis can give rise to homologs which have intracellular half-lives dramatically different than the corresponding wild-type protein. For example, the altered protein can be rendered either more stable or less stable to proteolytic degradation or other cellular process which result in destruction of, or otherwise inactivation of the POSH polypeptide of interest. Such homologs, and the genes which encode them, can be utilized to alter POSH levels by modulating the half-life of the protein. For instance, a short half-life can give rise to more transient biological effects and, when part of an inducible expression system, can allow tighter control of recombinant POSH levels within the cell. As above, such proteins, and particularly their recombinant nucleic acid constructs, can be used in gene therapy protocols.

In similar fashion, POSH homologs can be generated by the present combinatorial approach to act as antagonists, in that they are able to interfere with the ability of the corresponding wild-type protein to function.

In a representative embodiment of this method, the amino acid sequences for a population of POSH homologs are aligned, preferably to promote the highest homology possible. Such a population of variants can include, for example, homologs from one or more species, or homologs from the same species but which differ due to mutation. Amino acids which appear at each position of the aligned sequences are selected to create a degenerate set of combinatorial sequences. In a preferred embodiment, the combinatorial library is produced by way of a degenerate library of genes encoding a library of polypeptides which each include at least a portion of potential POSH sequences. For instance, a mixture of synthetic oligonucleotides can be enzymatically ligated into gene sequences such that the degenerate set of potential POSH nucleotide sequences are expressible as individual polypeptides, or alternatively, as a set of larger fusion proteins (e.g. for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential POSH sequences. The synthesis of degenerate oligonucleotides is well known in the art (see for example, Narang, SA (1983) Tetrahedron 39:3; Itakura et al., (1981) Recombinant DNA, Proc. 3rd Cleveland Sympos. Macromolecules, ed. A G Walton, Amsterdam: Elsevier pp273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, POSH homologs (both agonist and antagonist forms) can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of POSH polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of POSH homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In an illustrative embodiment of a screening assay, candidate combinatorial gene products of one of the subject proteins are displayed on the surface of a cell or virus, and the ability of particular cells or viral particles to bind a POSH polypeptide is detected in a "panning assay". For instance, a library of POSH variants can be cloned into the gene for a surface membrane protein of a bacterial cell (Ladner et al., WO 88/06630; Fuchs et al., (1991) Bio/Technology 9:1370-1371; and Goward et al., (1992) TIBS 18:136-140), and the resulting fusion protein detected by panning, e.g. using a fluorescently labeled molecule which binds the POSH polypeptide, to score for potentially functional homologs. Cells can be visually inspected and separated under a fluorescence microscope, or, where the morphology of the cell permits, separated by a fluorescence-activated cell sorter.

In similar fashion, the gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and fl are most often used in phage display libraries, as either of the phage gIII or gVII coat proteins can be used to generate fusion proteins without disrupting the ultimate packaging of the viral particle (Ladner et al., PCT publication WO 90/02909; Garrard et al., PCT publication WO 92/09690; Marks et al., (1992) J. Biol. Chem. 267:16007-16010; Griffiths et al., (1993) EMBO J. 12:725-734; Clackson et al., (1991) Nature 352:624-628; and Barbas et al., (1992) PNAS USA 89:4457-4461).

The invention also provides for reduction of the subject POSH polypeptides to generate mimetics, e.g. peptide or non-peptide agents, which are able to mimic binding of the authentic protein to another cellular partner. Such mutagenic techniques as described above, as well as the thioredoxin system, are also particularly useful for mapping the determinants of a POSH polypeptide which participate in protein-protein interactions involved in, for example, binding of proteins involved in viral maturation to each other. To illustrate, the critical residues of a POSH polypeptide which are involved in molecular recognition of a substrate protein can be determined and used to generate POSH polypeptide-derived peptidomimetics which bind to the substrate protein, and by inhibiting POSH binding, act to inhibit its biological activity. By employing, for example, scanning mutagenesis to map the amino acid residues of a POSH polypeptide which are involved in binding to another polypeptide, peptidomimetic compounds can be generated which mimic those residues involved in binding. For instance, non-hydrolyzable peptide analogs of such residues can be generated using benzodiazepine (e.g., see Freidinger et al., in Peptides: Chemistry and Biology, G. R. Marshall ed., ESCOM Publisher: Leiden, Netherlands, 1988), azepine (e.g., see Huffman et al., in Peptides: Chemistry and Biology, G. R. Marshall ed., ESCOM Publisher: Leiden, Netherlands, 1988), substituted gamma lactam rings (Garvey et al., in Peptides: Chemistry and Biology, G. R. Marshall ed., ESCOM Publisher: Leiden, Netherlands, 1988), keto-methylene pseudopeptides (Ewenson et al., (1986) J. Med. Chem. 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., (1985) Tetrahedron Lett 26:647; and Sato et al., (1986) J Chem Soc Perkin Trans 1:1231), and b-aminoalcohols (Gordon et al., (1985) Biochem Biophys Res Commun 126:419; and Dann et al., (1986) Biochem Biophys Res Commun 134:71).

The following table provides the sequences of the RING domain and the various SH3 domains.

TABLE 6

Amino Acid Sequences and related SEQ ID NOs for domains in human POSH

| Name of the sequence | Sequence | SEQ ID NO. |
|---|---|---|
| RING domain | CPVCLERLDASAKVLPCQHTFCKRCLLGIVGSRNELRCPEC | 26 |

TABLE 6-continued

Amino Acid Sequences and related SEQ ID NOs for domains in human POSH

| Name of the sequence | Sequence | SEQ ID NO. |
|---|---|---|
| 1st SH3 domain | PCAKALYNYEGKEPGDLKFSKGDIIILRRQVDENWYHGEVNGIHGFFPTNFVQIIK | 27 |
| 2nd SH3 domain | PQCKALYDFEVKDKEADKDCLPFAKDDVLTVIRRVDENWAEGMLADKIGIFPISYVEFNS | 28 |
| 3rd SH3 domain | SVYVAIYPYTPRKEDELELRKGEMFLVFERCQDGWFKGTSMHTSKIGVFPGNYVAPVT | 29 |
| 4th SH3 domain | ERHRVVVSYPPQSEAELELKEGDIVFVHKKREDGWFKGTLQRNGKTGLFPGSFVENI | 30 |

5. Antibodies and Uses Thereof

Another aspect of the invention pertains to an antibody specifically reactive with a POSH polypeptide. For example, by using immunogens derived from a POSH polypeptide, e.g., based on the cDNA sequences, anti-protein/anti-peptide antisera or monoclonal antibodies can be made by standard protocols (See, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., a POSH polypeptide or an antigenic fragment which is capable of eliciting an antibody response, or a fusion protein as described above). Techniques for conferring immunogenicity on a protein or peptide include conjugation to carriers or other techniques well known in the art. An immunogenic portion of a POSH polypeptide can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a POSH polypeptide of a mammal, e.g., antigenic determinants of a protein set forth in SEQ ID NO:2.

In one embodiment, antibodies are specific for a RING domain or an SH3 domain, and preferably the domain is part of a POSH polypeptide. In a more specific embodiment, the domain is part of an amino acid sequence set forth in SEQ ID NO:2. In a set of exemplary embodiments, an antibody binds to one or more SH3 domains represented by amino acids 137-192 of SEQ ID NO:2, amino acids 199-258 of SEQ ID NO:2, amino acids 448-505 of SEQ ID NO:2, and/or amino acids 832-888 of SEQ ID NO:2. In another exemplary embodiment, an antibody binds to a RING domain represented by amino acids 12-52 of SEQ ID NO:2. In another embodiment, the antibodies are immunoreactive with one or more proteins having an amino acid sequence that is at least 80% identical to an amino acid sequence as set forth in SEQ ID NO:2. In other embodiments, an antibody is immunoreactive with one or more proteins having an amino acid sequence that is 85%, 90%, 95%, 98%, 99% or identical to an amino acid sequence as set forth in SEQ ID NO:2.

Following immunization of an animal with an antigenic preparation of a POSH polypeptide, anti-POSH antisera can be obtained and, if desired, polyclonal anti-POSH antibodies isolated from the serum. To produce monoclonal antibodies, antibody-producing cells (lymphocytes) can be harvested from an immunized animal and fused by standard somatic cell-fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with a mammalian POSH polypeptide of the present invention and monoclonal antibodies isolated from a culture comprising such hybridoma cells. In one embodiment anti-human POSH antibodies specifically react with the protein encoded by a nucleic acid having SEQ ID NO:2.

The term antibody as used herein is intended to include fragments thereof which are also specifically reactive with one of the subject POSH polypeptides. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific, single-chain, and chimeric and humanized molecules having affinity for a POSH polypeptide conferred by at least one CDR region of the antibody. In preferred embodiments, the antibodies, the antibody further comprises a label attached thereto and able to be detected, (e.g., the label can be a radioisotope, fluorescent compound, enzyme or enzyme co-factor).

Anti-POSH antibodies can be used, e.g., to monitor POSH polypeptide levels in an individual, particularly the presence of POSH at the plasma membrane for determining whether or not said patient is infected with a virus such as an RNA virus, a retroid virus, and an envelop virus, or allowing determination of the efficacy of a given treatment regimen for an individual afflicted with such a disorder. In addition, POSH polypeptides are expected to localize, occasionally, to the released viral particle. Viral particles may be collected and assayed for the presence of a POSH polypeptide. The level of POSH polypeptide may be measured in a variety of sample types such as, for example, cells and/or in bodily fluid, such as in blood samples.

Another application of anti-POSH antibodies of the present invention is in the immunological screening of cDNA libraries constructed in expression vectors such as gt11, gt18-23, ZAP, and ORF8. Messenger libraries of this type, having coding sequences inserted in the correct reading frame and orientation, can produce fusion proteins. For instance, gt11 will produce fusion proteins whose amino termini consist of β-galactosidase amino acid sequences and whose carboxy termini consist of a foreign polypeptide. Antigenic epitopes of a POSH polypeptide, e.g., other orthologs of a particular protein or other paralogs from the same species, can then be detected with antibodies, as, for example, reacting nitrocellulose filters lifted from infected plates with the appropriate anti-POSH antibodies. Positive phage detected by this assay can then be isolated from the infected plate. Thus, the presence of POSH homologs can be detected and cloned from other animals, as can alternate isoforms (including splice variants) from humans.

6. Homology Searching of Nucleotide and Polypeptide Sequences

The nucleotide or amino acid sequences of the invention may be used as query sequences against databases such as GenBank, SwissProt, BLOCKS, and Pima II. These databases contain previously identified and annotated sequences that can be searched for regions of homology (similarity) using BLAST, which stands for Basic Local Alignment Search Tool (Altschul S F (1993) J Mol Evol 36:290-300; Altschul, S F et al (1990) J Mol Biol 215:403-10).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith, R. F. and T. F. Smith (1992; Protein Engineering 5:35-51), incorporated herein by reference, can be used when dealing with primary sequence patterns and secondary structure gap penalties. As disclosed in this application, sequences have lengths of at least 49 nucleotides and no more than 12% uncalled bases (where N is recorded rather than A, C, G, or T).

The BLAST approach, as detailed in Karlin and Altschul (1993; Proc Nat Acad Sci 90:5873-7) and incorporated herein by reference, searches matches between a query sequence and a database sequence, to evaluate the statistical significance of any matches found, and to report only those matches which satisfy the user-selected threshold of significance. Preferably the threshold is set at 10-25 for nucleotides and 3-15 for peptides.

7. Transgenic Animals and Uses Thereof

Another aspect of the invention features transgenic non-human animals which express a heterologous POSH gene, preferentially a human POSH gene of the present invention, and/or which have had one or both copies of the endogenous POSH genes disrupted in at least one of the tissue or cell-types of the animal. Accordingly, the invention features an animal model for viral infection. In one embodiment, the transgenic non-human animals is a mammal such as a mouse, rat, rabbit, goat, sheep, dog, cat, cow, or non-human primate. Without being bound to theory, it is proposed that such an animal may be susceptible to infection with envelop viruses, retroid viruses and RNA viruses such as various rhabdoviruses, lentiviruses, and filoviruses. Accordingly, such a transgenic animal may serve as a useful animal model to study the progression of diseases caused by such viruses.

Alternatively, such an animal can be useful as a basis to introduce one or more other human transgenes, to create a transgenic animal carrying multiple human genes involved in infection caused by retroid viruses, or RNA viruses, and envelop viruses. Retroid viruses include lentiviruses such as HIV. Other RNA viruses include filoviruses such as Ebola virus. As a result of the introduction of multiple human transgenes, the transgenic animal may become susceptible to certain viral infection and therefore provide an useful animal model to study these viral infection.

In a preferred embodiment, the transgenic animal carrying human POSH gene is useful as a basis to introduce other human genes involved in HIV infection, such as Cyclin T1, CD34, CCR5, and fusin (CRCX4). In a further embodiment, the additional human transgene is a gene involved in a disease or condition that is associated with AIDS (e.g. hypertension, Kaposi's sarcoma, cachexia, etc.) Such an animal may be an useful animal model for studying HIV infection, AIDS and related disease development.

Another aspect of the present invention concerns transgenic animals which are comprised of cells (of that animal) which contain a transgene of the present invention and which preferably (though optionally) express an exogenous POSH protein in one or more cells in the animal. A POSH transgene can encode the wild-type form of the protein, or can encode homologs thereof, as well as antisense constructs. Moreover, it may be desirable to express the heterologous POSH transgene conditionally such that either the timing or the level of POSH gene expression can be regulated. Such conditional expression can be provided using prokaryotic promoter sequences which require prokaryotic proteins to be simultaneous expressed in order to facilitate expression of the POSH transgene. Exemplary promoters and the corresponding trans-activating prokaryotic proteins are given in U.S. Pat. No. 4,833,080.

Moreover, transgenic animals exhibiting tissue specific expression can be generated, for example, by inserting a tissue specific regulatory element, such as an enhancer, into the transgene. For example, the endogenous POSH gene promoter or a portion thereof can be replaced with another promoter and/or enhancer, e.g., a CMV or a Moloney murine leukemia virus (MLV) promoter and/or enhancer.

Alternatively, non-human transgenic animals that only express HIV transgenes in the brain can be generated using brain specific promoters (e.g. myelin basic protein (MBP) promoter, the neurofilament protein (NF-L) promoter, the gonadotropin-releasing hormone promoter, the vasopressin promoter and the neuron-specific enolase promoter, see So Forss-Petter et al., Neuron, 5, 187, (1990). Such animals can provide a useful in vivo model to evaluate the ability of a potential anti-HIV drug to cross the blood-brain barrier. Other target cells for which specific promoters can be used are, for example, macrophages, T cells and B cells. Other tissue specific promoters are well-known in the art, see e.g. R. Jaenisch, Science, 240, 1468 (1988).

Non-human transgenic animals containing an inducible POSH transgene can be generated using inducible regulatory elements (e.g. metallothionein promoter), which are well-known in the art. POSH transgene expression can then be initiated in these animals by administering to the animal a compound which induces gene expression (e.g. heavy metals). Another preferred inducible system comprises a tetracycline-inducible transcriptional activator (U.S. Pat. No. 5,654,168 issued Aug. 5, 1997 to Bujard and Gossen and U.S. Pat. No. 5,650,298 issued Jul. 22, 1997 to Bujard et al.).

In general, transgenic animal lines can be obtained by generating transgenic animals having incorporated into their genome at least one transgene, selecting at least one founder from these animals and breeding the founder or founders to establish at least one line of transgenic animals having the selected transgene incorporated into their genome.

Animals for obtaining eggs or other nucleated cells (e.g. embryonic stem cells) for generating transgenic animals can be obtained from standard commercial sources such as Charles River Laboratories (Wilmington, Mass.), Taconic (Germantown, N.Y.), Harlan Sprague Dawley (Indianapolis, Ind.).

Eggs can be obtained from suitable animals, e.g., by flushing from the oviduct or using techniques described in U.S. Pat. No. 5,489,742 issued Feb. 6, 1996 to Hammer and Taurog; U.S. Pat. No. 5,625,125 issued on Apr. 29, 1997 to Bennett et al.; Gordon et al., 1980, Proc. Natl. Acad. Sci. USA 77:7380-7384; Gordon & Ruddle, 1981, Science 214: 1244-1246; U.S. Pat. No. 4,873,191 to T. E. Wagner and P. C. Hoppe; U.S. Pat. No. 5,604,131; Armstrong, et al. (1988) J. of Reproduction, 39:511 or PCT application No. PCT/FR93/00598 (WO 94/00568) by Mehtali et al. Preferably, the female is subjected to hormonal conditions effective to promote superovulation prior to obtaining the eggs.

Many techniques can be used to introduce DNA into an egg or other nucleated cell, including in vitro fertilization using sperm as a carrier of exogenous DNA ("sperm-mediated gene transfer", e.g., Lavitrano et al., 1989, Cell 57: 717-723), microinjection, gene targeting (Thompson et al., 1989, Cell 56: 313-321), electroporation (Lo, 1983, Mol. Cell. Biol. 3: 1803-1814), transfection, or retrovirus mediated gene transfer (Van der Putten et al., 1985, Proc. Natl. Acad. Sci. USA 82: 6148-6152). For a review of such techniques, see Gordon (1989), Transgenic Animals, Intl. Rev. Cytol. 115:171-229.

Except for sperm-mediated gene transfer, eggs should be fertilized in conjunction with (before, during or after) other transgene transfer techniques. A preferred method for fertilizing eggs is by breeding the female with a fertile male. However, eggs can also be fertilized by in vitro fertilization techniques.

Fertilized, transgene containing eggs can than be transferred to pseudopregnant animals, also termed "foster mother animals", using suitable techniques. Pseudopregnant animals can be obtained, for example, by placing 40-80 day old female animals, which are more than 8 weeks of age, in cages with infertile males, e.g., vasectomized males. The next morning females are checked for vaginal plugs. Females who have mated with vasectomized males are held aside until the time of transfer.

Recipient females can be synchronized, e.g. using GNRH agonist (GnRH-a): des-gly10, (D-Ala6)-LH-RH Ethylamide, SigmaChemical Co.,St. Louis, Mo. Alternatively, a unilateral pregnancy can be achieved by a brief surgical procedure involving the "peeling" away of the bursa membrane on the left uterine horn. Injected embryos can then be transferred to the left uterine horn via the infundibulum. Potential transgenic founders can typically be identified immediately at birth from the endogenous litter mates. For generating transgenic animals from embryonic stem cells, see e.g. Teratocarcinomas and embryonic stem cells, a practical approach, ed. E. J. Robertson, (IRL Press 1987) or in Potter et al Proc. Natl. Acad. Sci. USA 81, 7161 (1984), the teachings of which are incorporated herein by reference.

Founders that express the gene can then bred to establish a transgenic line. Accordingly, founder animals can be bred, inbred, crossbred or outbred to produce colonies of animals of the present invention. Animals comprising multiple transgenes can be generated by crossing different founder animals (e.g. an HIV transgenic animal and a transgenic animal, which expresses human CD4), as well as by introducing multiple transgenes into an egg or embryonic cell as described above. Furthermore, embryos from A-transgenic animals can be stored as frozen embryos, which are thawed and implanted into pseudo-pregnant animals when needed (See e.g. Hirabayashi et al. (1997) Exp Anim 46: 111 and Anzai (1994) Jikken Dobutsu 43: 247).

The present invention provides for transgenic animals that carry the transgene in all their cells, as well as animals that carry the transgene in some, but not all cells, i.e., mosaic animals. The transgene can be integrated as a single transgene or in tandem, e.g., head to head tandems, or head to tail or tail to tail or as multiple copies.

The successful expression of the transgene can be detected by any of several means well known to those skilled in the art. Non-limiting examples include Northern blot, in situ hybridization of mRNA analysis, Western blot analysis, immunohistochemistry, and FACS analysis of protein expression.

In a further aspect, the invention features non-human animal cells containing a POSH transgene, preferentially a human POSH transgene. For example, the animal cell (e.g. somatic cell or germ cell (i.e. egg or sperm)) can be obtained from the transgenic animal. Transgenic somatic cells or cell lines can be used, for example, in drug screening assays. Transgenic germ cells, on the other hand, can be used in generating transgenic progeny, as described above.

The invention further provides methods for identifying (screening) or for determining the safety and/or efficacy of virus therapeutics, i.e. compounds which are useful for treating and/or preventing the development of diseases or conditions, which are caused by, or contributed to by viral infection (e.g. AIDS). In addition the assays are useful for further improving known anti-viral compounds, e.g, by modifying their structure to increase their stability and/or activity and/or toxicity.

In addition to providing cells for in vitro assays, the transgenic animals themselves can be used in in vivo assays to identify viral therapeutics. For example, the animals can be used in assays to identify compounds which reduce or inhibit any phase of the viral life cycle, e.g., expression of one or more viral genes, activity of one or more viral proteins, glycosylation of one or more viral proteins, processing of one or more viral proteins, viral replication, assembly of virions, and/or budding of infectious virions.

In an exemplary embodiment, the assay comprises administering a test compound to a transgenic animal of the invention infected with a virus including RNA viruses, DNA viruses, retroidvirus and/or envelop viruses, and comparing a phenotypic change in the animal relative to a transgenic animal which has not received the test compound. For example, where the animal is infected with HIV, the phenotypic change can be the amelioration in an AIDS related complex (ARC), cataracts, inflammatory lesions in the central nervous system (CNV), a mild kidney sclerotic lesion, or a skin lesion, such as psoratic dermatitis, hyperkerstotic lesions, Kaposi's sarcoma or cachexia. The effect of a compound on inhibition of Kaposi's sarcoma can be determined, as described, e.g., in PCT/US97/11202 (WO97/49373) by Gallo et al. These and other HIV related symptoms or phenotypes are further described in Leonard et al. (1988) Science 242:1665.

In another embodiment, the phenotypic change is release/budding of virus particles. In yet another embodiment, the phenotypic change is the number of CD4+ T cells or the ratio of CD4+ T cells versus CD8+ T cells. In HIV infected humans as well as in HIV transgenic mice, analysis of lymph nodes indicate that the number of CD4+ T cells decreases and the number of CD8+ T cells increases. Numbers of CD4+ and CD8+ T cells can be determined, for example, by indirect immunofluorescence and flow cytometry, as described, e.g., in Santoro et al., supra.

Alternatively, a phenotypic change, e.g. a change in the expression level of an HIV gene can be monitored. The HIV RNA can be selected from the group consisting of gag mRNA, gag-pro-pol mRNA, vif mRNA, vpr mRNA, tat mRNA, rev mRNA, vpu/env mRNA, nef mRNA, and vpx mRNA. The HIV protein can be selected from the group consisting of Pr55 Gag and fragments thereof (p17 MA, p24 CA, p7 NC, p1, p9, p6, and p2), Pr160 Gag-Pro-Pol, and fragments thereof (p10 PR, p51 RT, p66 RT, p32 IN), p23 Vif, p15 Vpr, p14 Tat, p19 Rev, p16 Vpu, gPr 160 Env or fragments thereof (gp120 SU and gp41 TM), p27 Nef, and p14 Vpx. The level of any of these mRNAs or proteins can be determined in cells from a tissue sample, such as a skin biopsy, as described in, e.g., PCT/US97/11202 (WO97/49373) by Gallo et al. Quantitation of HIV mRNA and protein is further described elsewhere herein and also in, e.g., Dickie et al. (1996) AIDS Res. Human Retroviruses 12:1103. In a preferred embodiment, the level of gp120 on the surface of PBMC is determined. This can be done, as described in the examples, e.g., by immunofluorescence on PBMC obtained from the animals.

A further phenotypic change is the production level or rate of viral particles in the serum and/or tissue of the animal. This can be determined, e.g., by determining reverse transcriptase (RT activity) or viral load as described elsewhere herein as well as in PCT/US97/11202 (WO97/49373) by Gallo et al., such as by determining p24 antigen.

Yet another phenotypic change, which can indicate HIV infection or AIDS progression is the production of inflammatory cytokines such as IL-6, IL-8 and TNF-.alpha.; thus, efficacy of a compound as an anti-HIV therapeutic can be assessed by ELISA tests for the reduction of serum levels of any or all of these cytokines.

A vaccine can be tested by administering a test antigen to a transgenic animal of the invention. The animal can optionally be boosted with the same or a different antigen. Such animal is then infected with a virus such as HIV. The production of viral particles or expression of viral proteins is then measured at various times following the administration of the test vaccine. A decrease in the amount of viral particles produced or viral expression will indicate that the test vaccine is efficient in reducing or inhibiting viral production and/or expression. The amount of antibody produced by the animal in response to the vaccine antigen can also be determined according to methods known in the art and provides a relative indication of the immunogenicity of the particular antigen.

Cells from the transgenic animals of the invention can be established in culture and immortalized to establish cell lines. For example, immortalized cell lines can be established from the livers of transgenic rats, as described in Bulera et al. (1997) Hepatology 25: 1192. Cell lines from other types of cells can be established according to methods known in the art."

In one cell-based assay, cells expressing a POSH transgene can be infected with a virus of interest and incubated in the presence a test compound or a control compound. The production of viral particles is then compared. This assay system thus provides a means of identifying molecular antagonists which, for example, function by interfering with viral release/budding.

Cell based assays can also be used to identify compounds which modulate expression of a viral gene, modulate translation of a viral mRNA, or which modulate the stability of a viral mRNA or protein. Accordingly, a cell which is capable of expressing a particular viral protein can be incubated with a test compound and the amount of the viral protein produced in the cell medium can be measured and compared to that produced from a cell which has not been contacted with the test compound. The specificity of the compound for regulating the expression of the particular virus gene can be confirmed by various control analyses, e.g., measuring the expression of one or more control genes. This type of cellular assay can be particularly useful for determining the efficacy of antisense molecules or ribozymes.

8. RNA Interference, Ribozymes, Antisense and DNA Enzyme

In certain aspects, the invention relates to RNAi, ribozyme, antisense and other nucleic acid-related methods and compositions for manipulating (typically decreasing) a POSH activity. Exemplary RNAi and ribozyme molecules may comprise a sequence as shown in any of SEQ ID Nos: 15, 16, 18, 19, 21, 22, 24 and 25.

Certain embodiments of the invention make use of materials and methods for effecting knockdown of one or more POSH genes by means of RNA interference (RNAi). RNAi is a process of sequence-specific post-transcriptional gene repression which can occur in eukaryotic cells. In general, this process involves degradation of an mRNA of a particular sequence induced by double-stranded RNA (dsRNA) that is homologous to that sequence. For example, the expression of a long dsRNA corresponding to the sequence of a particular single-stranded mRNA (ss mRNA) will labilize that message, thereby "interfering" with expression of the corresponding gene. Accordingly, any selected gene may be repressed by introducing a dsRNA which corresponds to all or a substantial part of the mRNA for that gene. It appears that when a long dsRNA is expressed, it is initially processed by a ribonuclease III into shorter dsRNA oligonucleotides of as few as 21 to 22 base pairs in length. Furthermore, Accordingly, RNAi may be effected by introduction or expression of relatively short homologous dsRNAs. Indeed the use of relatively short homologous dsRNAs may have certain advantages as discussed below.

Mammalian cells have at least two pathways that are affected by double-stranded RNA (dsRNA). In the RNAi (sequence-specific) pathway, the initiating dsRNA is first broken into short interfering (si) RNAs, as described above. The siRNAs have sense and antisense strands of about 21 nucleotides that form approximately 19 nucleotide si RNAs with overhangs of two nucleotides at each 3' end. Short interfering RNAs are thought to provide the sequence information that allows a specific messenger RNA to be targeted for degradation. In contrast, the nonspecific pathway is triggered by dsRNA of any sequence, as long as it is at least about 30 base pairs in length. The nonspecific effects occur because dsRNA activates two enzymes: PKR, which in its active form phosphorylates the translation initiation factor eIF2 to shut down all protein synthesis, and 2', 5' oligoadenylate synthetase (2', 5'-AS), which synthesizes a molecule that activates Rnase L, a nonspecific enzyme that targets all mRNAs. The nonspecific pathway may represents a host response to stress or viral infection, and, in general, the effects of the nonspecific pathway are preferably minimized under preferred methods of the present invention. Significantly, longer dsRNAs appear to be required to induce the nonspecific pathway and, accordingly, dsRNAs shorter than about 30 bases pairs are preferred to effect gene repression by RNAi (see Hunter et al. (1975) J Biol Chem 250: 409-17; Manche et al. (1992) Mol Cell Biol 12: 5239-48; Minks et al. (1979) J Biol Chem 254: 10180-3; and Elbashir et al. (2001) Nature 411: 494-8).

RNAi has been shown to be effective in reducing or eliminating the expression of a POSH gene in a number of different organisms including Caenorhabditiis elegans (see e.g. Fire et al. (1998) Nature 391: 806-11), mouse eggs and embryos (Wianny et al. (2000) Nature Cell Biol 2: 70-5; Svoboda et al. (2000) Development 127: 4147-56), and cultured RAT-1 fibroblasts (Bahramina et al. (1999) Mol Cell Biol 19: 274-83), and appears to be an anciently evolved pathway available in eukaryotic plants and animals (Sharp (2001) Genes Dev. 15: 485-90). RNAi has proven to be an effective means of decreasing gene expression in a variety of cell types including HeLa cells, NIH/3T3 cells, COS cells, 293 cells and BHK-21 cells, and typically decreases expression of a gene to lower levels than that achieved using antisense techniques and, indeed, frequently eliminates expression entirely (see Bass (2001) Nature 411: 428-9). In mammalian cells, siRNAs are effective at concentrations that are several orders of magnitude below the concentrations typically used in antisense experiments (Elbashir et al. (2001) Nature 411: 494-8).

The double stranded oligonucleotides used to effect RNAi are preferably less than 30 base pairs in length and, more preferably, comprise about 25, 24, 23, 22, 21, 20, 19, 18 or 17 base pairs of ribonucleic acid. Optionally the dsRNA oligonucleotides of the invention may include 3' overhang ends. Exemplary 2-nucleotide 3' overhangs may be composed of ribonucleotide residues of any type and may even be composed of 2'-deoxythymidine resides, which lowers the cost of RNA synthesis and may enhance nuclease resistance of siRNAs in the cell culture medium and within transfected cells (see Elbashi et al. (2001) Nature 411: 494-8). Longer dsRNAs of 50, 75, 100 or even 500 base pairs or more may also be utilized in certain embodiments of the invention. Exemplary concentrations of dsRNAs for effecting RNAi are about 0.05 nM, 0.1 nM, 0.5 nM, 1.0 nM, 1.5 nM, 25 nM or 100 nM, although other concentrations may be utilized depending upon the nature of the cells treated, the gene target and other factors readily discernable the skilled artisan. Exemplary dsRNAs may be synthesized chemically or produced in vitro or in vivo using appropriate expression vectors. Exemplary synthetic RNAs include 21 nucleotide RNAs chemically synthesized using methods known in the art (e.g. Expedite RNA phophoramidites and thymidine phosphoramidite (Proligo, Germany). Synthetic oligonucleotides are preferably deprotected and gel-purified using methods known in the art (see e.g. Elbashir et al. (2001) Genes Dev. 15: 188-200). Longer RNAs may be transcribed from promoters, such as T7 RNA polymerase promoters, known in the art. A single RNA target, placed in both possible orientations downstream of an in vitro promoter, will transcribe both strands of the target to create a dsRNA oligonucleotide of the desired target sequence. Any of the above RNA species will be designed to include a portion of nucleic acid sequence represented in a POSH nucleic acid, such as, for example, a nucleic acid that hybridizes, under stringent and/or physiological conditions, to any of SEQ ID Nos: 1, 3, 4, 6, 8 and 10 and complements thereof.

The specific sequence utilized in design of the oligonucleotides may be any contiguous sequence of nucleotides contained within the expressed gene message of the target. Programs and algorithms, known in the art, may be used to select appropriate target sequences. In addition, optimal sequences may be selected utilizing programs designed to predict the secondary structure of a specified single stranded nucleic acid sequence and allowing selection of those sequences likely to occur in exposed single stranded regions of a folded mRNA. Methods and compositions for designing appropriate oligonucleotides may be found, for example, in U.S. Pat. No. 6,251,588, the contents of which are incorporated herein by reference. Messenger RNA (mRNA) is generally thought of as a linear molecule which contains the information for directing protein synthesis within the sequence of ribonucleotides, however studies have revealed a number of secondary and tertiary structures that exist in most mRNAs. Secondary structure elements in RNA are formed largely by Watson-Crick type interactions between different regions of the same RNA molecule. Important secondary structural elements include intramolecular double stranded regions, hairpin loops, bulges in duplex RNA and internal loops. Tertiary structural elements are formed when secondary structural elements come in contact with each other or with single stranded regions to produce a more complex three dimensional structure. A number of researchers have measured the binding energies of a large number of RNA duplex structures and have derived a set of rules which can be used to predict the secondary structure of RNA (see e.g. Jaeger et al. (1989) Proc. Natl. Acad. Sci. USA 86:7706 (1989); and Turner et al. (1988) Annu. Rev. Biophys. Biophys. Chem. 17:167). The rules are useful in identification of RNA structural elements and, in particular, for identifying single stranded RNA regions which may represent preferred segments of the mRNA to target for silencing RNAi, ribozyme or antisense technologies. Accordingly, preferred segments of the mRNA target can be identified for design of the RNAi mediating dsRNA oligonucleotides as well as for design of appropriate ribozyme and hammerheadribozyme compositions of the invention.

The dsRNA oligonucleotides may be introduced into the cell by transfection with an heterologous target gene using carrier compositions such as liposomes, which are known in the art—e.g. Lipofectamine 2000 (Life Technologies) as described by the manufacturer for adherent cell lines. Transfection of dsRNA oligonucleotides for targeting endogenous genes may be carried out using Oligofectamine (Life Technologies). Transfection efficiency may be checked using fluorescence microscopy for mammalian cell lines after co-transfection of hGFP-encoding pAD3 (Kehlenback et al. (1998) J Cell Biol 141: 863-74). The effectiveness of the RNAi may be assessed by any of a number of assays following introduction of the dsRNAs. These include Western blot analysis using antibodies which recognize the POSH gene product following sufficient time for turnover of the endogenous pool after new protein synthesis is repressed, reverse transcriptase polymerase chain reaction and Northern blot analysis to determine the level of existing POSH target mRNA.

Further compositions, methods and applications of RNAi technology are provided in U.S. Pat. Nos. 6,278,039, 5,723, 750 and 5,244,805, which are incorporated herein by reference.

Ribozyme molecules designed to, catalytically cleave POSH mRNA transcripts can also be used to prevent translation of suject POSH mRNAs and/or expression of POSH (see, e.g., PCT International Publication WO90/11364, published Oct. 4, 1990; Sarver et al. (1990) Science 247:1222-1225 and U.S. Pat. No. 5,093,246). Ribozymes are enzymatic RNA molecules capable of catalyzing the specific cleavage of RNA. (For a review, see Rossi (1994) Current Biology 4: 469-471). The mechanism of ribozyme action involves sequence specific hybridization of the ribozyme molecule to complementary target RNA, followed by an endonucleolytic cleavage event. The composition of ribozyme molecules preferably includes one or more sequences complementary to a POSH mRNA, and the well known catalytic sequence responsible for mRNA cleavage or a functionally equivalent sequence (see, e.g., U.S. Pat. No. 5,093,246, which is incorporated herein by reference in its entirety).

While ribozymes that cleave mRNA at site specific recognition sequences can be used to destroy target mRNAs, the use of hammerhead ribozymes is preferred. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art and is described more fully in Haseloff and Gerlach ((1988) Nature 334:585-591; and see PCT Appln. No. WO89/05852, the contents of which are incorporated herein by reference). Hammerhead ribozyme sequences can be embedded in a stable RNA such as a transfer RNA (tRNA) to increase cleavage efficiency in vivo (Perriman et al. (1995) Proc. Natl. Acad. Sci. USA, 92: 6175-79; de Feyter, and Gaudron, Methods in Molecular Biology, Vol. 74, Chapter 43, "Expressing Ribozymes in Plants", Edited by Turner, P. C, Humana Press Inc., Totowa, N.J.). In particular, RNA polymerase III-mediated expression of tRNA fusion ribozymes are well known in the art (see Kawasaki et al. (1998) Nature 393: 284-9; Kuwabara et al. (1998) Nature Biotechnol. 16: 961-5; and Kuwabara et al. (1998) Mol. Cell 2: 617-27; Koseki et al. (1999) J Virol 73: 1868-77; Kuwabara et al. (1999) Proc Natl Acad Sci USA 96: 1886-91; Tanabe et al. (2000) Nature 406: 473-4). There are typically a number of potential hammerhead ribozyme cleavage sites within a given target cDNA sequence. Preferably the ribozyme is engineered so that the cleavage recognition site is located near the 5' end of the target mRNA- to increase efficiency and minimize the intracellular accumulation of non-functional mRNA transcripts. Furthermore, the use of any cleavage recognition site located in the target sequence encoding different portions of the C-terminal amino acid domains of, for example, long and short forms of target would allow the selective targeting of one or the other form of the target, and thus, have a selective effect on one form of the target gene product.

Gene targeting ribozymes necessarily contain a hybridizing region complementary to two regions, each of at least 5 and preferably each 6, 7, 8, 9, 10, 11, 12, 13, 14, 15, 16, 17, 18, 19 or 20 contiguous nucleotides in length of a POSH mRNA, such as an mRNA of a sequence represented in any of SEQ ID Nos: 1, 3, 4, 6, 8 or 10. In addition, ribozymes possess highly specific endoribonuclease activity, which autocatalytically cleaves the target sense mRNA. The present invention extends to ribozymes which hybridize to a sense mRNA encoding a POSH gene such as a therapeutic drug target candidate gene, thereby hybridising to the sense mRNA and cleaving it, such that it is no longer capable of being translated to synthesize a functional polypeptide product.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al. (1984) Science 224:574-578; Zaug, et al. (1986) Science 231:470-475; Zaug, et al. (1986) Nature 324:429-433; published International patent application No. WO88/04300 by University Patents Inc.; Been, et al. (1986) Cell 47:207-216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a target gene or nucleic acid sequence.

Ribozymes can be composed of modified oligonucleotides (e.g., for improved stability, targeting, etc.) and should be delivered to cells which express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target messages and inhibit translation. Because ribozymes, unlike antisense molecules, are catalytic, a lower intracellular concentration is required for efficiency.

In certain embodiments, a ribozyme may be designed by first identifying a sequence portion sufficient to cause effective knockdown by RNAi. The same sequence portion may then be incorporated into a ribozyme. In this aspect of the invention, the gene-targeting portions of the ribozyme or RNAi are substantially the same sequence of at least 5 and preferably 6, 7, 8, 9, 10, 11, 12, 13, 14, 15, 16, 17, 18, 19 or 20 or more contiguous nucleotides of a POSH nucleic acid, such as a nucleic acid of any of SEQ ID Nos: 1, 3, 4, 6, 8, or 10. In a long target RNA chain, significant numbers of target sites are not accessible to the ribozyme because they are hidden within secondary or tertiary structures (Birikh et al. (1997) Eur J Biochem 245: 1-16). To overcome the problem of target RNA accessibility, computer generated predictions of secondary structure are typically used to identify targets that are most likely to be single-stranded or have an "open" configuration (see Jaeger et al. (1989) Methods Enzymol 183: 281-306). Other approaches utilize a systematic approach to predicting secondary structure which involves assessing a huge number of candidate hybridizing oligonucleotides molecules (seeMilner et al. (1997) Nat Biotechnol 15: 537-41; and Patzel and Sczakiel (1998) Nat Biotechnol 16: 64-8). Additionally, U.S. Pat. No. 6,251,588, the contents of which are hereby incorporated herein, describes methods for evaluating oligonucleotide probe sequences so as to predict the potential for hybridization to a target nucleic acid sequence. The method of the invention provides for the use of such methods to select preferred segments of a target mRNA sequence that are predicted to be single-stranded and, further, for the opportunistic utilization of the same or substantially identical target mRNA sequence, preferably comprising about 10-20 consecutive nucleotides of the target mRNA, in the design of both the RNAi oligonucleotides and ribozymes of the invention.

A further aspect of the invention relates to the use of the isolated "antisense" nucleic acids to inhibit expression, e.g., by inhibiting transcription and/or translation of a subject POSH nucleic acid. The antisense nucleic acids may bind to the potential drug target by conventional base pair complementarity, or, for example, in the case of binding to DNA duplexes, through specific interactions in the major groove of the double helix. In general, these methods refer to the range of techniques generally employed in the art, and include any methods that rely on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a POSH polypeptide. Alternatively, the antisense construct is an oligonucleotide probe, which is generated ex vivo and which, when introduced into the cell causes inhibition of expression by hybridizing with the mRNA and/or genomic sequences of a POSH nucleic acid. Such oligonucleotide probes are preferably modified oligonucleotides, which are resistant to endogenous nucleases, e.g., exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

With respect to antisense DNA, oligodeoxyribonucleotides derived from the translation initiation site, e.g., between the −10 and +10 regions of the POSH gene, are preferred. Antisense approaches involve the design of oligonucleotides (either DNA or RNA) that are complementary to mRNA encoding the POSH polypeptide. The antisense oligonucleotides will bind to the mRNA transcripts and prevent translation. Absolute complementarity, although preferred, is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. Nature 372:333). Therefore, oligonucleotides complementary to either the 5' or 3' untranslated, non-coding regions of a gene could be used in an antisense approach to inhibit translation of that mRNA. Oligonucleotides complementary to the 5' untranslated region of the mRNA should include the complement of the AUG start codon. Antisense oligonucleotides complementary to mRNA coding regions are less efficient inhibitors of translation but could also be used in accordance with the invention. Whether designed to hybridize to the 5', 3' or coding region of mRNA, antisense nucleic acids should be at least six nucleotides in length, and are preferably less that about 100 and more preferably less than about 50, 25, 17 or 10 nucleotides in length.

It is preferred that in vitro studies are first performed to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Results obtained using the antisense oligonucleotide may be compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The antisense oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. W088/09810, published Dec. 15, 1988) or the blood-brain barrier (see, e.g., PCT Publication No. W089/10134, published Apr. 25, 1988), hybridization-triggered cleavage agents. (See, e.g., Krol et al., 1988, BioTechniques 6:958-976) or intercalating agents. (See, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an alpha-anomeric oligonucleotide. An alpha-anomeric oligonucleotide forms specific double-stranded hybrids with complementary RNA in which, contrary to the usual anti-parallel orientation, the strands run parallel to each other (Gautier et al., 1987, Nucl. Acids Res. 15:6625-6641). The oligonucleotide is a 2'-0-methylribonucleotide (Inoue et al., 1987, Nucl. Acids Res. 15:6131-6148), or a chimeric RNA-DNA analogue (Inoue et al., 1987, FEBS Lett. 215:327-330).

While antisense nucleotides complementary to the coding region of a POSH mRNA sequence can be used, those complementary to the transcribed untranslated region may also be used.

In certain instances, it may be difficult to achieve intracellular concentrations of the antisense sufficient to suppress translation on endogenous mRNAs. Therefore a preferred approach utilizes a recombinant DNA construct in which the antisense oligonucleotide is placed under the control of a strong pol III or pol II promoter. The use of such a construct to transfect target cells will result in the transcription of sufficient amounts of single stranded RNAs that will form complementary base pairs with the endogenous potential drug target transcripts and thereby prevent translation. For example, a vector can be introduced such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al, 1982, Nature 296:39-42), etc. Any type of plasmid, cosmid, YAC or viral vector can be used to prepare the recombinant DNA construct, which can be introduced directly into the tissue site.

Alternatively, POSH gene expression can be reduced by targeting deoxyribonucleotide sequences complementary to the regulatory region of the gene (i.e., the promoter and/or enhancers) to form triple helical structures that prevent transcription of the gene in target cells in the body. (See generally, Helene, C. 1991, Anticancer Drug Des., 6(6):569-84; Helene, C., et al., 1992, Ann. N.Y. Acad. Sci., 660:27-36; and Maher, L. J., 1992, Bioassays 14(12):807-15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential POSH sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

A further aspect of the invention relates to the use of DNA enzymes to inhibit expression of POSH gene. DNA enzymes incorporate some of the mechanistic features of both antisense and ribozyme technologies. DNA enzymes are designed so that they recognize a particular target nucleic acid sequence, much like an antisense oligonucleotide, however much like a ribozyme they are catalytic and specifically cleave the target nucleic acid.

There are currently two basic types of DNA enzymes, and both of these were identified by Santoro and Joyce (see, for example, U.S. Pat. No. 6,110,462). The 10-23 DNA enzyme comprises a loop structure which connect two arms. The two arms provide specificity by recognizing the particular target nucleic acid sequence while the loop structure provides catalytic function under physiological conditions.

Briefly, to design an ideal DNA enzyme that specifically recognizes and cleaves a target nucleic acid, one of skill in the art must first identify the unique target sequence. This can be done using the same approach as outlined for antisense oligonucleotides. Preferably, the unique or substantially sequence is a G/C rich of approximately 18 to 22 nucleotides. High G/C content helps insure a stronger interaction between the DNA enzyme and the target sequence.

When synthesizing the DNA enzyme, the specific antisense recognition sequence that will target the enzyme to the message is divided so that it comprises the two arms of the DNA enzyme, and the DNA enzyme loop is placed between the two specific arms.

Methods of making and administering DNA enzymes can be found, for example, in U.S. Pat. No. 6,110,462. Similarly, methods of delivery DNA ribozymes in vitro or in vivo include methods of delivery RNA ribozyme, as outlined in detail above. Additionally, one of skill in the art will recognize that, like antisense oligonucleotide, DNA enzymes can be optionally modified to improve stability and improve resistance to degradation.

Antisense RNA and DNA, ribozyme, RNAi and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense CDNA constructs that synthesize antisense RNA constitutively or inducibly, depending on the promoter used, can be introduced stably into cell lines. Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2'O-methyl rather than phosphodiesterase linkages within the oligodeoxyribonucleotide backbone.

9. Drug Screening Assays

In certain aspects, the present invention also provides assays for identifying therapeutic agents which either interfere with or promote POSH function. In certain embodiments, agents of the invention are antiviral agents, optionally interfering with viral maturation, and preferably where the virus is a retroid virus, an RNA virus and an envelop virus. In certain preferred embodiments, an antiviral agent interferes with the ubiquitin ligase catalytic activity of POSH (e.g. POSH auto-ubiquitination or transfer to a target protein). In certain preferred embodiments, an antiviral agent interferes with the interaction between POSH and a POSH-AP polypeptide, for example an antiviral agent may disrupt or render irreversible the interaction between a POSH polypeptide and POSH-AP polypeptide such as another POSH polypeptide (as in the case of a POSH dimer, a heterodimer of two different POSH polypeptides, homomultimers and heteromultimers); a GTPase (eg. Rac, Rac1, Rho, Ras); an E2 enzyme and ubiquitin, or optionally, a cullin; a clathrin; AP-1; AP-2; an HSP70; an HSP90, Brca1, Bard1, Nef, PAK1, PAK2, PAK family, Vav, Cdc42, PI3K (e.g. p85 or p110, Nedd4, src (src family), a Gag, particularly an HIV Gag, Tsg101, VASP, RNB6, WASP, N-WASP and KIAA0674, Similar to Spred-2, as well as, in certain embodiments, proteins known to be associated with clathrin-coated vesicles and or proteins involved in the protein sorting pathway. In further embodiments, agents of the invention are anti-apoptotic agents, optionally interfering with JNK and/or NF-κB signaling. In yet additional embodiments, agents of the invention interfere with the signaling of a GTPase, such as Rac or Ras, optionally disrupting the interaction between a POSH polypeptide and a Rac protein. In certain embodiments, agents of the invention modulate the ubiquitin ligase activity of POSH and may be used to treat certain diseases related to ubiquitin ligase activity.

In certain embodiments, the invention provides assays to identify, optimize or otherwise assess agents that increase or decrease a ubiquitin-related activity of a POSH polypeptide. Ubiquitin-related activities of POSH polypeptides may include the self-ubiquitination activity of a POSH polypeptide, generally involving the transfer of ubiquitin from an E2 enzyme to the POSH polypeptide, and the ubiquitination of a target protein, generally involving the transfer of a ubiquitin from a POSH polypeptide to the target protein. In certain embodiments, a POSH activity is mediated, at least in part, by a POSH RING domain.

In certain embodiments, an assay comprises forming a mixture comprising a POSH polypeptide, an E2 polypeptide and a source of ubiquitin (which may be the E2 polypeptide pre-complexed with ubiquitin). Optionally the mixture comprises an E1 polypeptide and optionally the mixture comprises a target polypeptide. Additional components of the mixture may be selected to provide conditions consistent with the ubiquitination of the POSH polypeptide. One or more of a variety of parameters may be detected, such as POSH-ubiquitin conjugates, E2-ubiquitin thioesters, free ubiquitin and target polypeptide-ubiquitin complexes. The term "detect" is used herein to include a determination of the presence or absence of the subject of detection (e.g. POSH-ubiqutin, E2-ubiquitin, etc.), a quantitative measure of the amount of the subject of detection, or a mathematical calculation of the presence, absence or amount of the subject of detection, based on the detection of other parameters. The term "detect" includes the situation wherein the subject of detection is determined to be absent or below the level of sensitivity. Detection may comprise detection of a label (e.g. fluorescent label, radioisotope label, and other described below), resolution and identification by size (e.g. SDS-PAGE, mass spectroscopy), purification and detection, and other methods that, in view of this specification, will be available to one of skill in the art. For instance, radioisotope labeling may be measured by scintillation counting, or by densitometry after exposure to a photographic emulsion, or by using a device such as a Phosphorimager. Likewise, densitometry may be used to measure bound ubiquitin following a reaction with an enzyme label substrate that produces an opaque product when an enzyme label is used. In a preferred embodiment, an assay comprises detecting the POSH-ubiquitin conjugate.

In certain embodiments, an assay comprises forming a mixture comprising a POSH polypeptide, a target polypeptide and a source of ubiquitin (which may be the POSH polypeptide pre-complexed with ubiquitin). Optionally the mixture comprises an E1 and/or E2 polypeptide and optionally the mixture comprises an E2-ubiquitin thioester. Additional components of the mixture may be selected to provide conditions consistent with the ubiquitination of the target polypeptide. One or more of a variety of parameters may be detected, such as POSH-ubiquitin conjugates and target polypeptide-ubiquitin conjugates. In a preferred embodiment, an assay comprises detecting the target polypeptide-ubiquitin conjugate. In another preferred embodiment, an assay comprises detecting the POSH-ubiquitin conjugate.

An assay described above may be used in a screening assay to identify agents that modulate a ubiquitin-related activity of a POSH polypeptide. A screening assay will generally involve adding a test agent to one of the above assays, or any other assay designed to assess a ubiquitin-related activity of a POSH polypeptidee. The parameter(s) detected in a screening assay may be compared to a suitable reference. A suitable reference may be an assay run previously, in parallel or later that omits the test agent. A suitable reference may also be an average of previous measurements in the absence of the test agent. In general the components of a screening assay mixture may be added in any order consistent with the overall activity to be assessed, but certain variations may be preferred. For example, in certain embodiments, it may be desirable to pre-incubate the test agent and the E3 (e.g. the POSH polypeptide), followed by removing the test agent and addition of other components to complete the assay. In this manner, the effects of the agent solely on the POSH polypeptide may be assessed. In certain preferred embodiments, a screening assay for an antiviral agent employs a target polypeptide comprising an L domain, and preferably an HIV L domain.

In certain embodiments, an assay is performed in a high-throughput format. For example, one of the components of a mixture may be affixed to a solid substrate and one or more of the other components is labeled. For example, the POSH polypeptide may be affixed to a surface, such as a 96-well plate, and the ubiquitin is in solution and labeled. An E2 and E1 are also in solution, and the POSH-ubiquitin conjugate formation may be measured by washing the solid surface to remove uncomplexed labeled ubiquitin and detecting the ubiquitin that remains bound. Other variations may be used. For example, the amount of ubiquitin in solution may be detected. In certain embodiments, the formation of ubiquitin complexes may be measured by an interactive technique, such as FRET, wherein a ubiquitin is labeled with a first label and the desired complex partner (e.g. POSH polypeptide or target polypeptide) is labeled with a second label, wherein the first and second label interact when they come into close proximity to produce an altered signal. In FRET, the first and second labels are fluorophores. FRET is described in greater detail below. The formation of polyubiquitin complexes may be performed by mixing two or more pools of differentially labeled ubiquitin that interact upon formation of a polyubiqutin (see, e.g. U.S. Patent Publication 20020042083). High-throughput may be achieved by performing an interactive assay, such as FRET, in solution as well. In addition, if a polypeptide in the mixture, such as the POSH polypeptide or target polypeptide, is readily purifiable (e.g. with a specific antibody or via a tag such as biotin, FLAG, polyhistidine, etc.), the reaction may be performed in solution and the tagged polypeptide rapidly isolated, along with any polypeptides, such as ubiquitin, that are associated with the tagged polypeptide. Proteins may also be resolved by SDS-PAGE for detection.

In certain embodiments, the ubiquitin is labeled, either directly or indirectly. This typically allows for easy and rapid detection and measurement of ligated ubiquitin, making the assay useful for high-throughput screening applications. As descrived above, certain embodiments may employ one or more tagged or labeled proteins. A "tag" is meant to include moieties that facilitate rapid isolation of the tagged polypeptide. A tag may be used to facilitate attachment of a polypeptide to a surface. A "label" is meant to include moieties that facilitate rapid detection of the labeled polypeptide. Certain moieties may be used both as a label and a tag (e.g. epitope tags that are readily purified and detected with a well-characterized antibody). Biotinylation of polypeptides is well known, for example, a large number of biotinylation agents are known, including amine-reactive and thiol-reactive agents, for the biotinylation of proteins, nucleic acids, carbohydrates, carboxylic acids; see chapter 4, Molecular Probes Catalog, Haugland, 6th Ed. 1996, hereby incorporated by reference. A biotinylated substrate can be attached to a biotinylated component via avidin or streptavidin. Similarly, a large number of haptenylation reagents are also known.

An "E1" is a ubiquitin activating enzyme. In a preferred embodiment, E1 is capable of transferring ubiquitin to an E2. In a preferred embodiment, E1 forms a high energy thiolester bond with ubiquitin, thereby "activating" the ubiquitin. An "E2" is a ubiquitin carrier enzyme (also known as a ubiquitin conjugating enzyme). In a preferred embodiment, ubiquitin is transferred from E1 to E2. In a preferred embodiment, the transfer results in a thiolester bond formed between E2 and ubiquitin. In a preferred embodiment, E2 is capable of transferring ubiquitin to a POSH polypeptide.

In an alternative embodiment, a POSH polypeptide, E2 or target polypeptide is bound to a bead, optionally with the assistance of a tag. Following ligation, the beads may be separated from the unbound ubiquitin and the bound ubiquitin measured. In a preferred embodiment, POSH polypeptide is bound to beads and the composition used includes labeled ubiquitin. In this embodiment, the beads with bound ubiquitin may be separated using a fluorescence-activated cell sorting (FACS) machine. Methods for such use are described in U.S. patent application Ser. No. 09/047,119, which is hereby incorporated in its entirety. The amount of bound ubiquitin can then be measured.

In a screening assay, the effect of a test agent may be assessed by, for example, assessing the effect of the test agent on kinetics, steady-state and/or endpoint of the reaction.

The components of the various assay mixtures provided herein may be combined in varying amounts. In a preferred embodiment, ubiquitin (or E2 complexed ubiquitin) is combined at a final concentration of from 5 to 200 ng per 100 microliter reaction solution. Optionally E1 is used at a final concentration of from 1 to 50 ng per 100 microliter reaction solution. Optionally E2 is combined at a final concentration of 10 to 100 ng per 100 microliter reaction solution, more preferably 10-50 ng per 100 microliter reaction solution. In a preferred embodiment, POSH polypeptide is combined at a final concentration of from 1 ng to 500 ng per 100 microliter reaction solution.

Generally, an assay mixture is prepared so as to favor ubiquitin ligase activity and/or ubiquitination acitivty. Generally, this will be physiological conditions, such as 50-200 mM salt (e.g. NaCl, KCl), pH of between 5 and 9, and preferably between 6 and 8. Such conditions may be optimized through trial and error. Incubations may be performed at any temperature which facilitates optimal activity, typically between 4 and 40 degrees C. Incubation periods are selected for optimum activity, but may also be optimized to facilitate rapid high through put screening. Typically between 0.5 and 1.5 hours will be sufficient. A variety of other reagents may be included in the compositions. These include reagents like salts, solvents, buffers, neutral proteins, e.g. albumin, detergents, etc. which may be used to facilitate optimal ubiquitination enzyme activity and/or reduce nonspecific or background interactions. Also reagents that otherwise improve the efficiency of the assay, such as protease inhibitors, nuclease inhibitors, anti-microbial agents, etc., may be used. The compositions will also preferably include adenosine tri-phosphate (ATP). The mixture of components may be added in any order that promotes ubiquitin ligase activity or optimizes identification of candidate modulator effects. In a preferred embodiment, ubiquitin is provided in a reaction buffer solution, followed by addition of the ubiquitination enzymes. In an alternate preferred embodiment, ubiquitin is provided in a reaction buffer solution, a candidate modulator is then added, followed by addition of the ubiquitination enzymes.

In general, a test agent that decreases a POSH ubiquitin-related activity may be used to inhibit POSH function in vivo, while a test agent that increases a POSH ubiquitin-related activity may be used to stimulate POSH function in vivo. Test agent may be modified for use in vivo, e.g. by addition of a hydrophobic moiety, such as an ester.

Certain embodiments of the invention relate to assays for identifying agents that bind to a POSH polypeptide, optionally a particular domain of POSH such as an SH3 or RING domain. In preferred embodiments, a POSH polypeptide is a polypeptide comprising the fourth SH3 domain of hPOSH (SEQ ID NO: 30). A wide variety of assays may be used for this purpose, including labeled in vitro protein-protein binding assays, electrophoretic mobility shift assays, immunoassays for protein binding, and the like. The purified protein may also be used for determination of three-dimensional crystal structure, which can be used for modeling intermolecular interactions and design of test agents. In one embodiment, an assay detects agents which inhibit interaction of one or more subject POSH polypeptides with a POSH-AP.

In another embodiment, the assay detects agents which modulate the intrinsic biological activity of a POSH polypeptide or POSH complex, such as an enzymatic activity, binding to other cellular components, cellular compartmentalization, and the like.

In one aspect, the invention provides methods and compositions for the identification of compositions that interfere with the function of POSH polypeptides. Given the role of POSH polypeptides in viral production, compositions that perturb the formation or stability of the protein-protein interactions between POSH polypeptides and the proteins that they interact with, such as POSH-APs, and particularly POSH complexes comprising a viral protein, are candidate pharmaceuticals for the treatment of viral infections.

While not wishing to be bound to mechanism, it is postulated that POSH polypeptides promote the assembly of protein complexes that are important in release of virions and other biological processes. Complexes of the invention may include a combination of a POSH polypeptide and one or more of the following POSH-APs: a POSH-AP; a POSH polypeptide (as in the case of a POSH dimer, a heterodimer of two different POSH, homomultimers and heteromultimers); a GTPase (eg. Rac, Rac1, Rho, Ras); an E2 enzyme; ubiquitin, or optionally, a cullin; a clathrin; AP-1; AP-2; an HSP70; an HSP90, Brca1, Bard1, Nef, PAK1, PAK2, PAK family, Vav, Cdc42, PI3K (e.g. p85 or p110), Nedd4, src (src family), Tsg101, VASP, RNB6, WASP, N-WASP, a Gag, particularly an HIV Gag; and KIAA0674, Similar to Spred-2, as well as, in certain embodiments, proteins known to be associated with clathrin-coated vesicles and or proteins involved in the protein sorting pathway.

The type of complex formed by a POSH polypeptide will depend upon the domains present in the protein. While not intended to be limiting, exemplary domains of potential interacting proteins are provided below. A RING domain is expected to interact with cullins, E2 enzymes, AP-1, AP-2, and/or a substrate for ubiquitylation (e.g. in some instances, a protein comprising a Gag L domain). An SH3 domain may interact with Gag L domains and other proteins having the sequence motif P(T/S)AP (SEQ ID NO: 42), RXXP(T/S)AP (SEQ ID NO: 47), PXXDY, PXXP, PPXY or RXXPXXP, such as, for example, an HIV Gag sequence such as RQG-PKEPFR (SEQ ID NO: 45), PFRDY (SEQ ID NO: 43), PTAP (SEQ ID NO: 48) and RPEPTAP (SEQ ID NO: 38).

In a preferred assay for an antiviral or antiapoptotic agent, the test agent is assessed for its ability to disrupt or inhibit the formation of a complex of a POSH polypeptide and a Rac polypeptide, particularly a human Rac polypeptide, such as Rac 1.

A variety of assay formats will suffice and, in light of the present disclosure, those not expressly described herein will nevertheless be comprehended by one of ordinary skill in the art. Assay formats which approximate such conditions as formation of protein complexes, enzymatic activity, and even a POSH polypeptide-mediated membrane reorganization or vesicle formation activity, may be generated in many different forms, and include assays based on cell-free systems, e.g. purified proteins or cell lysates, as well as cell-based assays which utilize intact cells. Simple binding assays can also be used to detect agents which bind to POSH. Such binding assays may also identify agents that act by disrupting the interaction between a POSH polypeptide and a POSH interacting protein, or the binding of a POSH polypeptide or complex to a substrate. Agents to be tested can be produced, for example, by bacteria, yeast or other organisms (e.g. natural products), produced chemically (e.g. small molecules, including peptidomimetics), or produced recombinantly. In a preferred embodiment, the test agent is a small organic molecule, e.g., other than a peptide or oligonucleotide, having a molecular weight of less than about 2,000 daltons.

In many drug screening programs which test libraries of compounds and natural extracts, high throughput assays are desirable in order to maximize the number of compounds surveyed in a given period of time. Assays of the present invention which are performed in cell-free systems, such as may be developed with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target.

In preferred in vitro embodiments of the present assay, a reconstituted POSH complex comprises a reconstituted mixture of at least semi-purified proteins. By semi-purified, it is meant that the proteins utilized in the reconstituted mixture have been previously separated from other cellular or viral proteins. For instance, in contrast to cell lysates, the proteins involved in POSH complex formation are present in the mixture to at least 50% purity relative to all other proteins in the mixture, and more preferably are present at 90-95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure POSH complex assembly and/or disassembly.

Assaying POSH complexes, in the presence and absence of a candidate inhibitor, can be accomplished in any vessel suitable for containing the reactants. Examples include microtitre plates, test tubes, and micro-centrifuge tubes.

In one embodiment of the present invention, drug screening assays can be generated which detect inhibitory agents on the basis of their ability to interfere with assembly or stability of the POSH complex. In an exemplary binding assay, the compound of interest is contacted with a mixture comprising a POSH polypeptide and at least one interacting polypeptide. Detection and quantification of POSH complexes provides a means for determining the compound's efficacy at inhibiting (or potentiating) interaction between the two polypeptides. The efficacy of the compound can be assessed by generating dose response curves from data obtained using various concentrations of the test compound. Moreover, a control assay can also be performed to provide a baseline for comparison. In the control assay, the formation of complexes is quantitated in the absence of the test compound.

Complex formation between the POSH polypeptides and a substrate polypeptide may be detected by a variety of techniques, many of which are effectively described above. For instance, modulation in the formation of complexes can be quantitated using, for example, detectably labeled proteins (e.g. radiolabeled, fluorescently labeled, or enzymatically labeled), by immunoassay, or by chromatographic detection. Surface plasmon resonance systems, such as those available from Biacore International AB (Uppsala, Sweden), may also be used to detect protein-protein interaction Often, it will be desirable to immobilize one of the polypeptides to facilitate separation of complexes from uncomplexed forms of one of the proteins, as well as to accommodate automation of the assay. In an illustrative embodiment, a fusion protein can be provided which adds a domain that permits the protein to be bound to an insoluble matrix. For example, GST-POSH fusion proteins can be adsorbed onto glutathione sepharose beads (Sigma Chemical, St. Louis, Mo.) or glutathione derivatized microtitre plates, which are then combined with a potential interacting protein, e.g. an 35S-labeled polypeptide, and the test compound and incubated under conditions conducive to complex formation. Following incubation, the beads are washed to remove any unbound interacting protein, and the matrix bead-bound radiolabel determined directly (e.g. beads placed in scintillant), or in the supernatant after the complexes are dissociated, e.g. when microtitre plate is used. Alternatively, after washing away unbound protein, the complexes can be dissociated from the matrix, separated by SDS-PAGE gel, and the level of interacting polypeptide found in the matrix-bound fraction quantitated from the gel using standard electrophoretic techniques.

In a further embodiment, agents that bind to a POSH may be identified by using an immobilized POSH. In an illustrative embodiment, a fusion protein can be provided which adds a domain that permits the protein to be bound to an insoluble matrix. For example, GST-POSH fusion proteins can be adsorbed onto glutathione sepharose beads (Sigma Chemical, St. Louis, Mo.) or glutathione derivatized microtitre plates, which are then combined with a potential labeled binding agent and incubated under conditions conducive to binding. Following incubation, the beads are washed to remove any unbound agent, and the matrix bead-bound label determined directly, or in the supernatant after the bound agent is dissociated.

In yet another embodiment, the POSH polypeptide and potential interacting polypeptide can be used to generate an interaction trap assay (see also, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696), for subsequently detecting agents which disrupt binding of the proteins to one and other.

In particular, the method makes use of chimeric genes which express hybrid proteins. To illustrate, a first hybrid gene comprises the coding sequence for a DNA-binding domain of a transcriptional activator can be fused in frame to the coding sequence for a "bait" protein, e.g., a POSH polypeptide of sufficient length to bind to a potential interacting protein. The second hybrid protein encodes a transcriptional activation domain fused in frame to a gene encoding a "fish" protein, e.g., a potential interacting protein of sufficient length to interact with the POSH polypeptide portion of the bait fusion protein. If the bait and fish proteins are able to interact, e.g., form a POSH complex, they bring into close proximity the two domains of the transcriptional activator. This proximity causes transcription of a reporter gene which is operably linked to a transcriptional regulatory site responsive to the transcriptional activator, and expression of the reporter gene can be detected and used to score for the interaction of the bait and fish proteins.

In accordance with the present invention, the method includes providing a host cell, preferably a yeast cell, e.g., *Kluyverei lactis*, *Schizosaccharomyces pombe*, *Ustilago maydis*, *Saccharomyces cerevisiae*, *Neurospora crassa*, *Aspergillus niger*, *Aspergillus nidulans*, *Pichia pastoris*, *Candida tropicalis*, and *Hansenula polymorpha*, though most preferably *S cerevisiae* or *S. pombe*. The host cell contains a reporter gene having a binding site for the DNA-binding domain of a transcriptional activator used in the bait protein, such that the reporter gene expresses a detectable gene product when the gene is transcriptionally activated. The first chimeric gene may be present in a chromosome of the host cell, or as part of an expression vector. Interaction trap assays may also be performed in mammalian and bacterial cell types.

The host cell also contains a first chimeric gene which is capable of being expressed in the host cell. The gene encodes a chimeric protein, which comprises (i) a DNA-binding domain that recognizes the responsive element on the reporter gene in the host cell, and (ii) a bait protein, such as a POSH polypeptide sequence.

A second chimeric gene is also provided which is capable of being expressed in the host cell, and encodes the "fish" fusion protein. In one embodiment, both the first and the second chimeric genes are introduced into the host cell in the form of plasmids. Preferably, however, the first chimeric gene is present in a chromosome of the host cell and the second chimeric gene is introduced into the host cell as part of a plasmid.

Preferably, the DNA-binding domain of the first hybrid protein and the transcriptional activation domain of the second hybrid protein are derived from transcriptional activators having separable DNA-binding and transcriptional activation domains. For instance, these separate DNA-binding and transcriptional activation domains are known to be found in the yeast GAL4 protein, and are known to be found in the yeast GCN4 and ADR1 proteins. Many other proteins involved in transcription also have separable binding and transcriptional activation domains which make them useful for the present invention, and include, for example, the LexA and VP 16 proteins. It will be understood that other (substantially) transcriptionally-inert DNA-binding domains may be used in the subject constructs; such as domains of ACE1, 1cI, lac repressor, jun or fos. In another embodiment, the DNA-binding domain and the transcriptional activation domain may be from different proteins. The use of a LexA DNA binding domain provides certain advantages. For example, in yeast, the LexA moiety contains no activation function and has no known effect on transcription of yeast genes. In addition, use of LexA allows control over the sensitivity of the assay to the level of interaction (see, for example, the Brent et al. PCT publication WO94/10300).

In preferred embodiments, any enzymatic activity associated with the bait or fish proteins is inactivated, e.g., dominant negative or other mutants of a POSH polypeptide can be used.

Continuing with the illustrated example, the POSH polypeptide-mediated interaction, if any, between the bait and fish fusion proteins in the host cell, therefore, causes the activation domain to activate transcription of the reporter gene. The method is carried out by introducing the first chimeric gene and the second chimeric gene into the host cell, and subjecting that cell to conditions under which the bait and fish fusion proteins and are expressed in sufficient quantity for the reporter gene to be activated. The formation of a POSH-POSH-AP complex results in a detectable signal produced by the expression of the reporter gene. Accordingly, the level of formation of a complex in the presence of a test compound and in the absence of the test compound can be evaluated by detecting the level of expression of the reporter gene in each case. Various reporter constructs may be used in accord with the methods of the invention and include, for example, reporter genes which produce such detectable signals as selected from the group consisting of an enzymatic signal, a fluorescent signal, a phosphorescent signal and drug resistance.

One aspect of the present invention provides reconstituted protein preparations including a POSH polypeptide and one or more interacting polypeptides.

In still further embodiments of the present assay, the POSH complex is generated in whole cells, taking advantage of cell culture techniques to support the subject assay. For example, as described below, the POSH complex can be constituted in a eukaryotic cell culture system, including mammalian and yeast cells. Often it will be desirable to express one or more viral proteins (eg. Gag or Env) in such a cell along with a subject POSH polypeptide. It may also be desirable to infect the cell with a virus of interest. Advantages to generating the subject assay in an intact cell include the ability to detect inhibitors which are functional in an environment more closely approximating that which therapeutic use of the inhibitor would require, including the ability of the agent to gain entry into the cell. Furthermore, certain of the in vivo embodiments of the assay, such as examples given below, are amenable to high through-put analysis of candidate agents.

The components of the POSH complex can be endogenous to the cell selected to support the assay. Alternatively, some or all of the components can be derived from exogenous sources. For instance, fusion proteins can be introduced into the cell by recombinant techniques (such as through the use of an expression vector), as well as by microinjecting the fusion protein itself or mRNA encoding the fusion protein.

In many embodiments, a cell is manipulated after incubation with a candidate agent and assayed for a POSH activity. In certain embodiments a POSH activity is represented by production of virus like particles. As demonstrated herein, an agent that disrupts POSH activity can cause a decrease in the production of virus like particles. Other bioassays for POSH activities may include apoptosis assays (e.g. cell survival assays, apoptosis reporter gene assays, etc.) and NF-kB nuclear localization assays (see e.g. Tapon et al. (1998) EMBO J. 17: 1395-1404). In certain embodiments, POSH activities may include, without limitation, complex formation, ubiquitination and membrane fusion events (eg. release of viral buds or fusion of vesicles). POSH complex formation may be assessed by immunoprecipitation and analysis of co-immunoprecipiated proteins or affinity purification and analysis of co-purified proteins. Fluorescence Resonance Energy Transfer (FRET)-based assays may also be used to determine complex formation. Fluorescent molecules having the proper emission and excitation spectra that are brought into close proximity with one another can exhibit FRET. The fluorescent molecules are chosen such that the emission spectrum of one of the molecules (the donor molecule) overlaps with the excitation spectrum of the other molecule (the acceptor molecule). The donor molecule is excited by light of appropriate intensity within the donor's excitation spectrum. The donor then emits the absorbed energy as fluorescent light. The fluorescent energy it produces is quenched by the acceptor molecule. FRET can be manifested as a reduction in the intensity of the fluorescent signal from the donor, reduction in the lifetime of its excited state, and/or re-emission of fluorescent light at the longer wavelengths (lower energies) characteristic of the acceptor. When the fluorescent proteins physically separate, FRET effects are diminished or eliminated. (U.S. Pat. No. 5,981,200).

For example, a cyan fluorescent protein is excited by light at roughly 425-450 nm wavelength and emits light in the range of 450-500 nm. Yellow fluorescent protein is excited by light at roughly 500-525 nm and emits light at 525-500 nm. If these two proteins are placed in solution, the cyan and yellow fluorescence may be separately visualized. However, if these two proteins are forced into close proximity with each other, the fluorescent properties will be altered by FRET. The bluish light emitted by CFP will be absorbed by YFP and re-emitted as yellow light. This means that when the proteins are stimulated with light at wavelength 450 nm, the cyan emitted light is greatly reduced and the yellow light, which is not normally stimulated at this wavelength, is greatly increased. FRET is typically monitored by measuring the spectrum of emitted light in response to stimulation with light in the excitation range of the donor and calculating a ratio between the donor-emitted light and the acceptor-emitted light. When the donor:acceptor emission ratio is high, FRET is not occurring and the two fluorescent proteins are not in close proximity. When the donor: acceptor emission ratio is low, FRET is occurring and the two fluorescent proteins are in close proximity. In this manner, the interaction between a first and second polypeptide may be measured.

The occurrence of FRET also causes the fluorescence lifetime of the donor fluorescent moiety to decrease. This change in fluorescence lifetime can be measured using a technique termed fluorescence lifetime imaging technology (FLIM) (Verveer et al. (2000) *Science* 290: 1567-1570; Squire et al. (1999) *J. Microsc.* 193: 36; Verveer et al. (2000) *Biophys. J.* 78: 2127). Global analysis techniques for analyzing FLIM data have been developed. These algorithms use the understanding that the donor fluorescent moiety exists in only a limited number of states each with a distinct fluorescence lifetime. Quantitative maps of each state can be generated on a pixel-by-pixel basis.

To perform FRET-based assays, the POSH polypeptide and the interacting protein of interest are both fluorescently labeled. Suitable fluorescent labels are, in view of this specification, well known in the art. Examples are provided below, but suitable fluorescent labels not specifically discussed are also available to those of skill in the art. Fluorescent labeling may be accomplished by expressing a polypeptide as a fusion protein with a fluorescent protein, for example fluorescent proteins isolated from jellyfish, corals and other coelenterates. Exemplary fluorescent proteins include the many variants of the green fluorescent protein (GFP) of *Aequoria victoria. Variants may be brighter, dimmer, or have different excitation and/or emission spectra. Certain variants are altered such that they no longer appear green, and may appear blue, cyan, yellow or red (termed BFP, CFP, YFP and RFP, respectively). Fluorescent proteins may be stably attached to polypeptides through a variety of covalent and noncovalent linkages, including, for example, peptide bonds (eg. expression as a fusion protein), chemical cross-linking and biotin-streptavidin coupling.* For examples of fluorescent proteins, see U.S. Pat. Nos. 5,625,048; 5,777,079; 6,066,476; 6,124,128; Prasher et al. (1992) *Gene,* 111:229-233; Heim et al. (1994) *Proc. Natl. Acad Sci., USA,* 91:12501-04; Ward et al. (1982) *Photochem. Photobiol.,* 35:803-808; Levine et al. (1982) *Comp. Biochem. Physiol.,* 72B:77-85; Tersikh et al. (2000) *Science* 290: 1585-88.

Other exemplary fluorescent moieties well known in the art include derivatives of fluorescein, benzoxadioazole, coumarin, eosin, Lucifer Yellow, pyridyloxazole and rhodamine. These and many other exemplary fluorescent moieties may be found in the *Handbook of Fluorescent Probes and Research Chemicals* (2000, Molecular Probes, Inc.), along with methodologies for modifying polypeptides with such moieties. Exemplary proteins that fluoresce when combined with a fluorescent moiety include, yellow fluorescent protein from *Vibrio fischeri* (Baldwin et al. (1990) *Biochemistry* 29:5509-15), peridinin-chlorophyll a binding protein from the dinoflagellate *Symbiodinium* sp. (Morris et al. (1994) *Plant Molecular Biology* 24:673:77) and phycobiliproteins from marine cyanobacteria such as *Synechococcus*, e.g., phycoerythrin and phycocyanin (Wilbanks et al. (1993) *J. Biol. Chem.* 268:1226-35). These proteins require flavins, peridinin-chlorophyll a and various phycobilins, respectively, as fluorescent co-factors.

FRET-based assays may be used in cell-based assays and in cell-free assays. FRET-based assays are amenable to high-throughput screening methods including Fluorescence Activated Cell Sorting and fluorescent scanning of microtiter arrays.

In a further embodiment, transcript levels may be measured in cells having higher or lower levels of POSH activity in order to identify genes that are regulated by POSH. Promoter regions for such genes (or larger portions of such genes) may be operatively linked to a reporter gene and used in a reporter gene-based assay to detect agents that enhance or diminish POSH-regulated gene expression. Transcript levels may be determined in any way known in the art, such as, for example, Northern blotting, RT-PCR, microarray, etc. Increased POSH activity may be achieved, for example, by introducing a strong POSH expression vector. Decreased POSH activity may be achieved, for example, by RNAi, antisense, ribozyme, gene knockout, etc.

In general, where the screening assay is a binding assay (whether protein-protein binding, agent-protein binding, etc.), one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

In further embodiments, the invention provides methods for identifying targets for therapeutic intervention. A polypeptide that interacts with POSH or participates in a POSH-mediated process (such as viral maturation) may be used to identify candidate therapeutics. Such targets may be identified by identifying proteins that associated with POSH (POSH-APs) by, for example, immunoprecipitation with an anti-POSH antibody, in silico analysis of high-throughput binding data, two-hybrid screens, and other protein-protein interaction assays described herein or otherwise known in the art in view of this disclosure. Agents that bind to such targets or disrupt protein-protein interactions thereof, or inhibit a biochemical activity thereof may be used in such an assay. Targets that may be identified by such approaches include: a GTPase (eg. Rac, Rac1, Rho, Ras); an E2 enzyme, a cullin; a clathrin; AP-1; AP-2; an HSP70; an HSP90, Brca1, Bard1, Nef, PAK1, PAK2, PAK family, Vav, Cdc42, PI3K (e.g. p85 or p110), Nedd4, src (src family), Tsg101, VASP, RNB6, WASP, N-WASP, a Gag, particularly an HIV Gag; and KIAA0674, Similar to Spred-2, as well as, in certain embodiments, proteins known to be associated with clathrin-coated vesicles, proteins involved in the protein sorting pathway and proteins involved in a Rac signaling pathway.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4° and 40° C. Incubation periods are selected for optimum activity, but may also be optimized to facilitate rapid high-throughput screening.

In certain embodiments, a test agent may be assessed for its ability to perturb the localization of a POSH polypeptide, e.g. preventing POSH localization to the nucleus and/or the Golgi network.

10. Methods and Compositions for Treatment of Viral Disorders

In a further aspect, the invention provides methods and compositions for treatment of viral disorders, and particularly disorders caused by retroid viruses, RNA viruses and/or envelop viruses, including but not limited to retroviruses, rhabdoviruses, lentiviruses, and filoviruses. Preferred therapeutics of the invention function by disrupting the biological activity of a POSH polypeptide or POSH complex in viral maturation.

Exemplary therapeutics of the invention include nucleic acid therapies such as for example RNAi constructs, antisense oligonucleotides, ribozyme, and DNA enzymes. Other POSH therapeutics include polypeptides, peptidomimetics, antibodies and small molecules.

Antisense therapies of the invention include methods of introducing antisense nucleic acids to disrupt the expression of POSH polypeptides or proteins that are necessary for POSH function.

RNAi therapies include methods of introducing RNAi constructs to downregulate the expression of POSH polypeptides or proteins that are necessary for POSH function. Exemplary RNAi therapeutics include any one of SEQ ID Nos: 15, 16, 18, 19, 21, 22, 24 and 25.

Therapeutic polypeptides may be generated by designing polypeptides to mimic certain protein domains important in the formation of POSH complexes, such as, for example SH3 or RING domains. For example, a polypeptide comprising a POSH SH3 domain such as for example the SH3 domain as set forth in SEQ ID No: 30 will compete for binding to a POSH SH3 domain and will therefore act to disrupt binding of a partner protein. In one embodiment, a binding partner may be Gag. In another embodiment, a binding partner may be Rac. In a further embodiment, a polypeptide that resembles an L domain may disrupt recruitment of Gag to the POSH complex.

In view of the specification, methods for generating antibodies directed to epitopes of POSH and POSH-interacting proteins are known in the art. Antibodies may be introduced into cells by a variety of methods. One exemplary method comprises generating a nucleic acid encoding a single chain antibody that is capable of disrupting a POSH complex. Such a nucleic acid may be conjugated to antibody that binds to receptors on the surface of target cells. It is contemplated that in certain embodiments, the antibody may target viral proteins that are present on the surface of infected cells, and in this way deliver the nucleic acid only to infected cells. Once bound to the target cell surface, the antibody is taken up by endocytosis, and the conjugated nucleic acid is transcribed and translated to produce a single chain antibody that interacts with and disrupts the targeted POSH complex. Nucleic acids expressing the desired single chain antibody may also be introduced into cells using a variety of more conventional techniques, such as viral transfection (eg. using an adenoviral system) or liposome-mediated transfection.

Small molecules of the invention may be identified for their ability to modulate the formation of POSH complexes, as described above.

In view of the teachings herein, one of skill in the art will understand that the methods and compositions of the invention are applicable to a wide range of viruses such as for example retroid viruses, RNA viruses, and envelop viruses. In a preferred embodiment, the present invention is applicable to retroid viruses. In a more preferred embodiment, the present invention is further applicable to retroviruses (retroviridae). In another more preferred embodiment, the present invention is applicable to lentivirus, including primate lentivirus group. In a most preferred embodiment, the present invention is applicable to Human Immunodeficiency virus (HIV), Human Immunodeficiency virus type-1 (HIV-1), Hepatitis B Virus (HBV) and Human T-cell Leukemia Virus (HTLV).

While not intended to be limiting, relevant retroviruses include: C-type retrovirus which causes lymphosarcoma in Northern Pike, the C-type retrovirus which infects mink, the caprine lentivirus which infects sheep, the Equine Infectious Anemia Virus (EIAV), the C-type retrovirus which infects pigs, the Avian Leukosis Sarcoma Virus (ALSV), the Feline Leukemia Virus (FeLV), the Feline Aids Virus, the Bovine Leukemia Virus (BLV), the Simian Leukemia Virus (SLV), the Simian Immuno-deficiency Virus (SIV), the Human T-cell Leukemia Virus type-I (HTLV-I), the Human T-cell Leukemia Virus type-II (HTLV-II), Human Immunodeficiency virus type-2 (HIV-2) and Human Immunodeficiency virus type-1 (HIV-1).

The method and compositions of the present invention are further applicable to RNA viruses, including ssRNA negative-strand viruses and ssRNA positive-strand viruses. The ssRNA positive-strand viruses include Hepatitis C Virus (HCV). In a preferred embodiment, the present invention is applicable to mononegavirales, including filoviruses. Filoviruses further include Ebola viruses and Marburg viruses.

Other RNA viruses include picornaviruses such as enterovirus, poliovirus, coxsackievirus and hepatitis A virus, the caliciviruses, including Norwalk-like viruses, the rhabdoviruses, including rabies virus, the togaviruses including alphaviruses, Semliki Forest virus, denguevirus, yellow fever virus and rubella virus, the orthomyxoviruses, including Type A, B, and C influenza viruses, the bunyaviruses, including the Rift Valley fever virus and the hantavirus, the filoviruses such as Ebola virus and Marburg virus, and the paramyxoviruses, including mumps virus and measles virus. Additional viruses that may be treated include herpes viruses.

11. Effective Dose

Toxicity and therapeutic efficacy of such compounds can be determined by standard pharmaceutical procedures in cell cultures or experimental animals, e.g., for determining The Ld 50 (The Dose Lethal To 50% Of The Population) And The $Ed_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic induces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

12. Formulation and Use

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

An exemplary composition of the invention comprises an RNAi mixed with a delivery system, such as a liposome system, and optionally including an acceptable excipient. In a preferred embodiment, the composition is formulated for topical administration for, e.g. herpes virus infections.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. in addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

For therapies involving the administration of nucleic acids, the oligomers of the invention can be formulated for a variety of modes of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, intranodal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

Exemplification

The invention now being generally described, it will be more readily understood by reference to the following examples, which are included merely for purposes of illustration of certain aspects and embodiments of the present invention, and are not intended to limit the invention.

EXAMPLES

1. Role of POSH in Virus-like Particle (VLP) Budding

1. Objective:

Use RNAi to inhibit POSH gene expression and compare the efficiency of viral budding and GAG expression and processing in treated and untreated cells.

2. Study Plan:

HeLa SS-6 cells are transfected with mRNA-specific RNAi in order to knockdown the target proteins. Since maximal reduction of target protein by RNAi is achieved after 48 hours, cells are transfected twice—first to reduce target mRNAs, and subsequently to express the viral Gag protein. The second transfection is performed with pNLenv (plasmid that encodes HIV) and with low amounts of RNAi to maintain the knockdown of target protein during the time of gag expression and budding of VLPs. Reduction in mRNA levels due to RNAi effect is verified by RT-PCR amplification of target mRNA.

3. Methods, Materials, Solutions a. Methods i. Transfections according to manufacturer's protocol and as described in procedure.

ii. Protein determined by Bradford assay.

iii. SDS-PAGE in Hoeffer miniVE electrophoresis system. Transfer in Bio-Rad mini-protean II wet transfer system. Blots visualized using Typhoon system, and ImageQuant software (ABbiotech)

b. Materials

| Material | Manufacturer | Catalog # | Batch # |
|---|---|---|---|
| Lipofectamine 2000 (LF2000) | Life Technologies | 11668-019 | 1112496 |
| OptiMEM | Life Technologies | 31985-047 | 3063119 |
| RNAi Lamin A/C | Self | 13 | |
| RNAi TSG101 688 | Self | 65 | |
| RNAi Posh 524 | Self | 81 | |
| plenvl1 PTAP | Self | 148 | |
| plenvl1 ATAP | Self | 149 | |
| Anti-p24 polyclonal antibody | Seramun | | A-0236/5-10-01 |
| Anti-Rabbit Cy5 conjugated antibody | Jackson | 144-175-115 | 48715 |
| 10% acrylamide Tris-Glycine SDS-PAGE gel | Life Technologies | NP0321 | 1081371 |
| Nitrocellulose membrane | Schleicher & Schuell | 401353 | BA-83 |
| NuPAGE 20X transfer buffer | Life Technologies | NP0006-1 | 224365 |
| 0.45 μm filter | Schleicher & Schuell | 10462100 | CS1018-1 | c. Solutions

| | Compound | Concentration |
|---|---|---|
| Lysis Buffer | Tris-HCl pH 7.6 | 50 mM |
| | MgCl$_2$ | 15 mM |
| | NaCl | 150 mM |
| | Glycerol | 10% |
| | EDTA | 1 mM |
| | EGTA | 1 mM |
| | ASB-14 (add immediately before use) | 1% |
| 6X Sample Buffer | Tris-HCl, pH = 6.8 | 1 M |
| | Glycerol | 30% |
| | SDS | 10% |
| | DTT | 9.3% |
| | Bromophenol Blue | 0.012% |
| TBS-T | Tris pH = 7.6 | 20 mM |
| | NaCl | 137 mM |
| | Tween-20 | 0.1% |

4. Procedure a. Schedule

| Day | | | | |
|---|---|---|---|---|
| 1 | 2 | 3 | 4 | 5 |
| Plate cells | Transfection I (RNAi only) | Passage cells (1:3) | Transfection II (RNAi and pNlenv) (12:00, PM) | Extract RNA for RT-PCR (post transfection) |
| | | | Extract RNA for RT-PCR (pre-transfection) | Harvest VLPs and cells |

Day 1

Plate HeLa SS-6 cells in 6-well plates (35 mm wells) at concentration of $5 \times 10^5$ cells/well.

c. Day 2

2 hours transfection replace growth medium with 2 ml growth medium without antibiotics Transfection I:

| Reaction | RNAi name | TAGDA# | Reactions | RNAi [nM] | RNAi [20 μM] μl | A OPtiMEM (μl) | B LF2000 mix (μl) |
|---|---|---|---|---|---|---|---|
| 1 | Lamin A/C | 13 | 2 | 50 | 12.5 | 500 | 500 |
| 2 | Lamin A/C | 13 | 1 | 50 | 6.25 | 250 | 250 |
| 3 | TSG101 688 | 65 | 2 | 20 | 5 | 500 | 500 |
| 5 | Posh 524 | 81 | 2 | 50 | 12.5 | 500 | 500 |

Transfections:

Prepare LF2000 mix: 250 μl OptiMEM+5 μl LF2000 for each reaction. Mix by inversion, 5 times. Incubate 5 minutes at room temperature.

Prepare RNA dilution in OptiMEM (Table 1, column A). Add LF2000 mix dropwise to diluted RNA (Table 1, column B). Mix by gentle vortex. Incubate at room temperature 25 minutes, covered with aluminum foil.

Add 500 μl transfection mixture to cells dropwise and mix by rocking side to side.

Incubate overnight.

Day 3

Split 1:3 after 24 hours. (Plate 4 wells for each reaction, except reaction 2 which is plated into 3 wells.)

e. Day4

2 hours pre-transfection replace medium with DMEM growth medium without antibiotics.

| Reaction | RNAi name | TAGDA# | Plasmid | Reactions | Plasmid (µg/µl) | A Plasmid for 2.4 µg (µl) | B RNAi [20 µM] for 10 nM (µl) | C OPtiMEM (µl) | D LF2000 mix (µl) |
|---|---|---|---|---|---|---|---|---|---|
| 1 | Lamin A/C | 13 | PTAP | 3 |  | 3.4 | 3.75 | 750 | 750 |
| 2 | Lamin A/C | 13 | ATAP | 3 |  | 2.5 | 3.75 | 750 | 750 |
| 3 | TSG101 688 | 65 | PTAP | 3 |  | 3.4 | 3.75 | 750 | 750 |
| 5 | Posh 524 | 81 | PTAP | 3 |  | 3.4 | 3.75 | 750 | 750 |

Prepare LF2000 mix: 250 µl OptiMEM+5 µl LF2000 for each reaction. Mix by inversion, 5 times. Incubate 5 minutes at room temperature.

Prepare RNA+DNA diluted in OptiMEM (Transfection II, A+B+C)

Add LF2000 mix (Transfection II, D) to diluted RNA+DNA dropwise, mix by gentle vortex, and incubate 1 h while protected from light with aluminum foil.

Add LF2000 and DNA+RNA to cells, 500 µl/well, mix by gentle rocking and incubate overnight.

f. Day 5

Collect samples for VLP assay (approximately 24 hours post-transfection) by the following procedure (cells from one well from each sample is taken for RNA assay, by RT-PCR).

g. Cell Extracts
i. Pellet floating cells by centrifugation (5 min, 3000 rpm at 4° C.), save supernatant (continue with supernatant immediately to step h), scrape remaining cells in the medium which remains in the well, add to the corresponding floating cell pellet and centrifuge for 5 minutes, 1800 rpm at 4° C.
ii. Wash cell pellet twice with ice-cold PBS.
iii. Resuspend cell pellet in 100 µl lysis buffer and incubate 20 minutes on ice.
iv. Centrifuge at 14,000 rpm for 15 min. Transfer supernatant to a clean tube. This is the cell extract.
v. Prepare 10 µl of cell extract samples for SDS-PAGE by adding SDS-PAGE sample buffer to 1x, and boiling for 10 minutes. Remove an aliquot of the remaining sample for protein determination to verify total initial starting material. Save remaining cell extract at −80° C.

h. Purification of VLPs from Cell Media
i. Filter the supernatant from step g through a 0.45 m filter.
ii. Centrifuge supernatant at 14,000 rpm at 4° C. for at least 2 h.
iii. Aspirate supernatant carefully.
iv. Re-suspend VLP pellet in hot (100° C. warmed for 10 min at least) 1× sample buffer.
v. Boil samples for 10 minutes, 100° C.

Western Blot Analysis
i. Run all samples from stages A and B on Tris-Glycine SDS-PAGE 10% (120V for 1.5 h.).
ii. Transfer samples to nitrocellulose membrane (65V for 1.5 h.).
iii. Stain membrane with ponceau S solution.
iv. Block with 10% low fat milk in TBS-T for 1 h.
v. Incubate with anti p24 rabbit 1:500 in TBS-T o/n.
vi. Wash 3 times with TBS-T for 7 min each wash.
vii. Incubate with secondary antibody anti rabbit cy5 1:500 for 30 min.
viii. Wash five times for 10 min in TBS-T
ix. View in Typhoon gel imaging system (Molecular Dynamics/APBiotech) for fluorescence signal.

Figure 11:
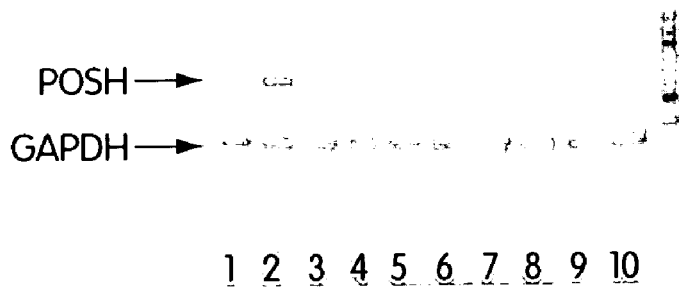
FIG. 11: Knockdown of POSH mRNA by siRNA duplexes. HeLa SS-6 cells were transfected with siRNA against Lamin A/C (lanes 1, 2) or POSH (lanes 3-10). POSH siRNA was directed against the coding region (153-lanes 3, 4; 155-lanes 5, 6) or the 3'UTR (157-lanes 7, 8; 159-lanes 9, 10). Cells were harvested 24 hours post-transfection, RNA extracted, and POSH mRNA levels compared by RT-PCR of a discrete sequence in the coding region of the POSH gene (see FIG. 10). GAPDH is used an RT-PCR control in each reaction.
Figure 12:
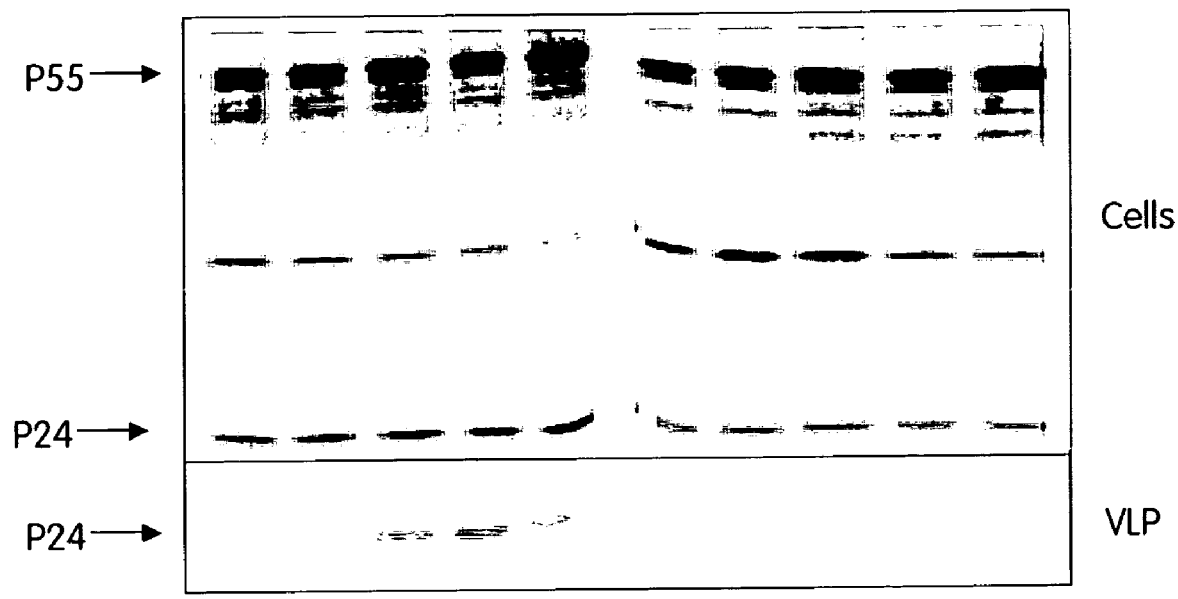
FIG. 12: POSH affects the release of VLP from cells. A) Phosphohimages of SDS-PAGE gels of immunoprecipitations of 35S pulse-chase labeled Gag proteins are presented for cell and viral lysates from transfected HeLa cells that were either untreated or treated with POSH RNAi (50 nM for 48 hours). The time during the chase period (1, 2, 3, 4 and 5 hours after the pulse) are presented from left to right for each image.
Figure 13:
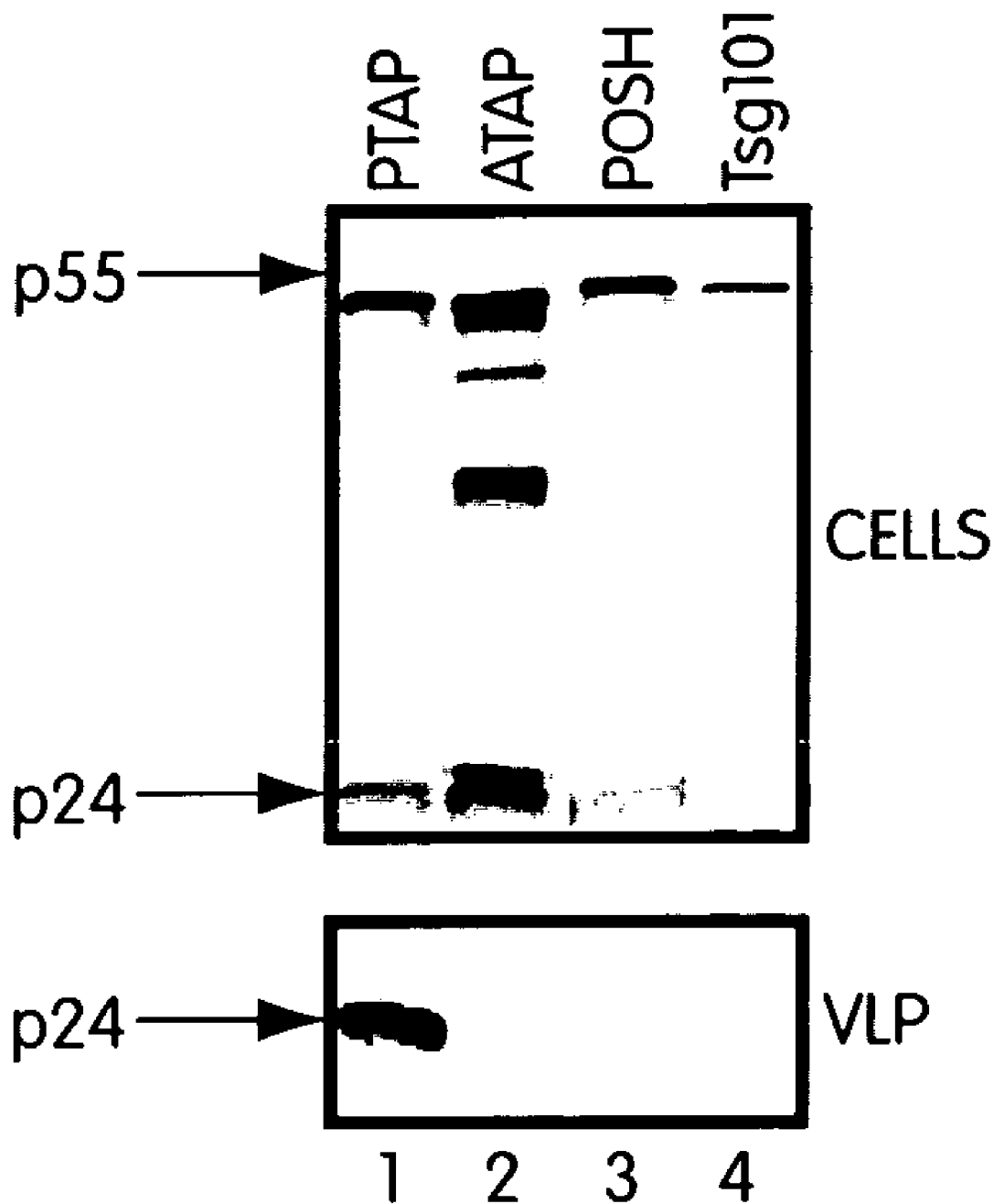
FIG. 13: Release of VLP from cells at steady state. Hela cells were transfected with an HIV-encoding plasmid and siRNA. Lanes 1, 3 and 4 were transfected with wild-type HIV-encoding plasmid. Lane 2 was transfected with an HIV-encoding plasmids which contains a point mutation in p6 (PTAP to ATAP). Control siRNA (lamin A/C) was transfected to cells in lanes 1 and 2. siRNA to Tsg101 was transfected in lane 4 and siRNA to POSH in lane 3.

Results are shown in FIGS. 11-13.

2. Exemplary POSH RT-PCR Primers and siRNA Duplexes

| | RT-PCR primers | | | |
|---|---|---|---|---|
| Name | Position | | Sequence | |
| Sense primer | POSH = 271 | 271 | 5'CTTGCCTTGCCAGCATAC 3' | (SEQ ID NO:12) |
| Anti-sense primer | POSH = 926c | 926C | 5'CTGCCAGCATTCCTTCAG 3' | (SEQ ID NO:13) | siRNA duplexes:

| | | |
|---|---|---|
| siRNA No: | 153 | |
| siRNA Name: | POSH-230 | |
| Position in mRNA | 426–446 | |
| Target sequence: | 5'AACAGAGGCCTTGGAAACCTG 3' | SEQ ID NO:14 |
| siRNA sense strand: | 5'dTdTCAGAGGCCUUGGAAACCUG 3' | SEQ ID NO:15 |
| siRNA anti-sense strand: | 5'dTdTCAGGUUUCCAAGGCCUCUG 3' | SEQ ID NO:16 |
| siRNA No: | 155 | |
| siRNA Name: | POSH-442 | |
| Position in mRNA | 638–658 | |

```
-continued

Target sequence:          5'AAAGAGCCTGGAGACCTTAAA 3'      SEQ ID NO:17 siRNA sense strand:       5'ddTdTAGAGCCUGGAGACCUUAAA 3'   SEQ ID NO:18 siRNA anti-sense strand:  5'ddTdTUUUAAGGUCUCCAGGCUCU 3'   SEQ ID NO:19
siRNA No:                 157
siRNA Name:               POSH-U111
Position in mRNA          2973-2993
Target sequence:          5'AAGGATTGGTATGTGACTCTG 3'      SEQ ID NO:20 siRNA sense strand:       5'dTdTGGAUUGGUAUGUGACUCUG 3'    SEQ ID NO:21 siRNA anti-sense strand:  5'dTdTCAGAGUCACAUACCAAUCC 3'    SEQ ID NO:22
siRNA No:                 159
siRNA Name:               POSH-U410
Position in mRNA          3272-3292
Target sequence:          5'AAGCTGGATTATCTCCTGTTG 3'      SEQ ID NO:23 siRNA sense strand:       5'ddTdTGCUGGAUUAUCUCCUGUUG 3'   SEQ ID NO:24 siRNA anti-sense strand:  5'ddTdTCAACAGGAGAUAAUCCAGC 3'   SEQ ID NO:25
```

3. Effects of POSH RNAi on HIV Release: Kinetics

A1. Transfections
1. One day before transfection plate cells at a concentration of $5 \times 10^6$ cell/well in 15 cm plates.
2. Two hours before transfection, replace cell media to 20 ml complete DMEM without antibiotics.
3. DNA dilution: for each transfection dilute 62.5 µl RNAi in 2.5 ml OptiMEM according to the table below. RNAi stock is 20 µM (recommended concentration: 50 nM, dilution in total medium amount 1:400).
4. LF 2000 dilution: for each transfection dilute 50 µl lipofectamine 2000 reagent in 2.5 ml OptiMEM.
5. Incubate diluted RNAi and LF 2000 for 5 minutes at RT.
6. Mix the diluted RNAi with diluted LF2000 and incubated for 20-25 minutes at RT.
7. Add the mixure to the cells (drop wise) and incubate for 24 hours at 37° C. in $CO_2$ incubator.
8. One day after RNAi transfection split cells (in complete MEM medium to 215 cm plate and 1 well in a 6 wells plate)
9. One day after cells split perform HIV transfection according to SP 30-012-01.
10. 6 hours after HIV transfection replace medium to complete MEM medium.
* It is important to perform RT-PCR for Posh to assure complete knockdown.

A2. Total RNA Purification.
1. One day after transfection, wash cells twice with sterile PBS.
2. Scrape cells in 2.3 ml/200 µl (for 15 cm plate/I well of a 6 wells plate) Tri reagent (with sterile scrapers) and freeze in −70° C. (RNA purification and RT-PCR will be done by molecular biology unit) rack no. A16 —samples for RT.

| Treatment | Chase time (hours) | Fraction | Labeling |
|---|---|---|---|
| Control = WT | 1 | Cells | A1 |
|  |  | VLP | A1 V |
|  | 2 | Cells | A2 |
|  |  | VLP | A2 V |
|  | 3 | Cells | A3 |
|  |  | VLP | A3 V |
|  | 4 | Cells | A4 |
|  |  | VLP | A4 V |
|  | 5 | Cells | A5 |
|  |  | VLP | A5 V |
| Posh + WT | 1 | Cells | B1 |
|  |  | VLP | B1 V |
|  | 2 | Cells | B2 |
|  |  | VLP | B2 V |
|  | 3 | Cells | B3 |
|  |  | VLP | B3 V |
|  | 4 | Cells | B4 |
|  |  | VLP | B4 V |
|  | 5 | Cells | B5 |
|  |  | VLP | B5 V |

B. Labeling
1. Take out starvation medium, thaw and place at 37° C.
2. Scrape cells in growth medium and transfer gently into 15 ml conical tube.
3. Centrifuge to pellet cells at 1800 rpm for 5 minutes at room temperature.
4. Aspirate supernatant and let tube stand for 10 sec. Remove the rest of the supernatant with a 200 µl pipetman.
5. Gently add 10 ml warm starvation medium and resuspend carefully with a 10 ml pipette, up and down, just turning may not resolve the cell pellet).
6. Transfer cells to 10 ml tube and place in the incubator for 60 minutes. Set an Eppendorf thermo mixer to 37° C.
7. Centrifuge to pellet cells at 1800 rpm for 5 minutes at room temperature.
8. Aspirate supernatant and let tube stand for 10 sec. Remove the rest of the supernatant with a 200 µl pipetman.
9. Cut a 200 µl tip from the end and resuspend cells (~1.5 $10^7$ cells in 150 µl RPMI without Met, but try not to go over 250 µl if you have more cells) gently in 150 µl starvation medium. Transfer cells to an Eppendorf tube and place in the thermo mixer. Wait 10 sec and transfer the rest of the cells from the 10 ml tube to the Eppendorf tube, if necessary add another 50 µl to splash the rest of the cells out (all specimens should have the same volume of labeling reaction!).

10. Pulse: Add 50 µl of $^{35}$S-methionine (specific activity 14.2 µCi/µl), tightly cup tubes and place in thermo mixer. Set the mixing speed to the lowest possible (700 rpm) and incubate for 25 minutes.

7. Fix gel in 25% ethanol and 10% acetic acid for 15 minutes.
8. Pour off the fixation solution and soak gels in Amplify solution (NAMP 100 Amersham) for 15 minutes.
9. Dry gels on warm plate (60-80° C.) under vacuum.
10. Expose gels to screen for 2 hours and scan.

4. Effect of siRNA Against Human POSH on Production of Infectious Virus from HeLa Cells The following plan is according to the standard siRNA transfection protocol:

Plan:

| Days | | | | |
|---|---|---|---|---|
| 1 | 2 | 3 | 4 | 5.5 |
| Plate HeLa cells | Transfect RNA$_1$ | Split high (1:3) | Transfect siRNA + HIV-1$_{NL4-3}$ | Harvest virus And start infectivity assay, take samples for Western blot |

11. Stop the pulse by adding 1 ml ice-cold chase/stop medium. Shake tube very gently three times and pellet cells at 6000 rpm for 6 sec.
12. Remove supernatant with a 1 ml tip. Add gently 1 ml ice-cold chase/stop medium to the pelleted cells and invert gently to resuspend.
13. Chase: Transfer all tubes to the thermo mixer and incubate for the required chase time (830:1, 2, 3, 4 and 5 hours; 828: 3 hours only). At the end of total chase time, place tubes on ice, add 1 ml ice-cold chase/stop and pellet cells for 1 minute at 14,000 rpm. Remove supernatant and transfer supernatant to a second eppendorf tube. The cell pellet freeze at −80° C., until all tubes are ready.
14. Centrifuge supernatants for 2 hours at 14,000 rpm, 4° C. Remove the supernatant very gently, leave 20 µl in the tube (labeled as V) and freeze at −80° C. until the end of the time course.
*** All steps are done on ice with ice-cold buffers
15. When the time course is over, remove all tubes form −80° C. Lyse VLP pellet (from step 14) and cell pellet (step 13) by adding 500 µl of lysis buffer (see solutions), resuspend well by pipeting up and down three times. Incubate on ice for 15 minutes, and spin in an eppendorf centrifuge for 15 minutes at 4° C., 14,000 rpm. Remove supernatant to a fresh tube, discard pellet.
16. Perform IP with anti-p24 sheep for all samples.

C. Immunopercipitation
1. Preclearing: add to all samples 15 µl ImmunoPure PlusG (Pierce). Rotate for 1 hour at 4° C. in a cycler, spin 5 min at 4° C., and transfer to a new tube for IP.
2. Add to all samples 20 µl of p24-protein G conjugated beads and incubate 4 hours in a cycler at 4° C.
3. Post immunoprecipitations, transfer all immunoprecipitations to a fresh tube.
4. Wash beads once with high salt buffer, once with medium salt buffer and once with low salt buffer. After each spin don't remove all solution, but leave 50 µl solution on the beads. After the last spin remove supernatant carefully with a loading tip and leave ~10 µl solution.
5. Add to each tube 20 µl 2×SDS sample buffer. Heat to 70° C. for 10 minutes.
6. Samples were separated on 10% SDS-PAGE.

As siRNA the following was used:

13 (=Lamin control)

153 (=human POSH Ub ligase)

day 3 (one days following first siRNA transfections):

HeLa cells were harvested, split again 1:3 in fresh DMEM and seeded in T75 flasks.

day 4:

medium was removed, fresh DMEM medium was added and cells were transfected again with siRNA in combination with one of the following HIV-1 expression plasmids:

Env− (HIV-1$_{NL4-3}$ (Adachi et al., 1986) with deletion in env gene, does not allow the expression of Env but other HIV-1 proteins), and VSV-G (CMV driven expression vector for vesicular stomatitis virus G protein). This combination allows single round infection as progeny viruses following infections with VSV-G pseudotyped viruses are free of Env glycoproteins.

Env+ (HIV-1$_{NL4-3}$ wild type) for multiple round of infections.

Note: Both construct Env− and Env+ contained EGFP were cloned into the nef open reading frame of HIV-1$_{NL4-3}$. This way all cells transfected or infected cells with active virus gene expression can be detected by autoflourescence (based on T. Fukunori et al. 2000, Lenardo et al., 2002)

For control one T25 flaks was transfected with GFP-N1 (a CMV expression vector for plain GFP).

day 5:

the transfection efficiency was estimated by counting fluorescent cells in the GFP-N1 transfected culture using FACS analysis.

day 5.5:

36 hrs after second transfection, virus was harvested. Virus stocks were prepared as follows: HeLa cells were scraped and virus-containing supernatants were clarified by centrifugation (1,000×g, 5 min) and filtered through a 0.45 µm-pore-size filter to remove residual cells and debris. Stocks were aliquoted and frozen at −80° C. For biochemical analyses virions from aliquots of supernatants were pelleted (99 min, 14,000 rpm, 4° C.) and lysed (according to Ott et al., 2002). Samples of cell and virus fractions were analyzed by Western blot using anti-CA antibodies.

For infectivity assay serial dilutions of virus stocks were prepared in RPMI medium and used to infect Jurkat cells. 3 days post infection the percentage of infected cells in parallel cultures was estimated by FACS analyses. Each infection experiments were set up in 3 parallel cultures in 96 well plates (based on Bolton et al., 2002).

For control, one culture was incubated with cell culture supernatant form cell transfected with GFP-N1. No fluorescent cells were detected attesting for absence of unspecific staining of cells with GFP from the virus producer cells.

Remark: During virus production no toxic effect (other than some HIV-related cytopathic effect) was observed in human POSH transfected cultures when compared to the Lamin transfected culture.

Figure 19:
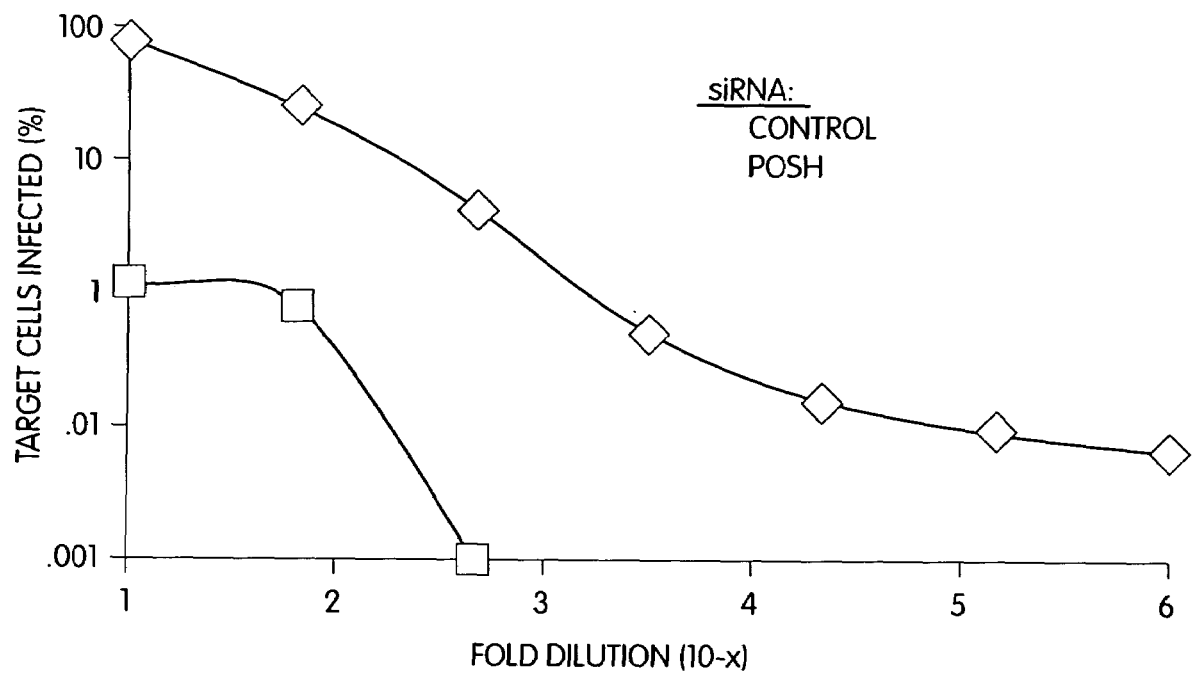
FIG. 19: Partial knockdown of human POSH results in four logs reduction of HIV1 infectivity. The results from infectivity assay are presented are presented in the diagram. The vertical axis shows the percentage of target cells infected, and the horizontal axis shows the fold dilution of virus stocks used (see Example 4 for details of the experiment). The open squares (top line) indicate the results from the control, and the closed squares (bottom line) indicate the results from transfecting cells with RNAi to POSH.

Results, shown in FIG. 19, demonstrate that knocking down POSH results in four logs reduction of HIV1 infectivity.

5. Effect of Knocking Down Human POSH on PTAP- and PPEY-Mediated Viral Release

On the first day of the experiment, HeLa SS6 cells were plated in a 6-well plate at $5 \times 10^5$ cells/well. The cells were transfected on the second day with LF2000 reagent and with the following RNAi's: Lamin, TSG101 and hPOSH (50 nM/well). On the third day, cells were split 1:2. The cells were transfected again on the fourth day (with LF2000 reagent) with a supporting dose (10 nM/well) of the same RNAi's and DNA (1 ug/well): Lamin with PTAP, Lamin with ATAP, Lamin with PPEY, TSG101 with PTAP, TSG101 with PPEY, TSG101 with ATAP, hPOSH with PTAP, hPOSH with PPEY, and hPOSH with ATAP. 24 hours later centrifuge supernatant for VLPs and extract protein from cells. Load all samples to a 12% tris-glycine gel, transfer to a nitrocellulose membrane and incubate with xp24.

Figure 20:
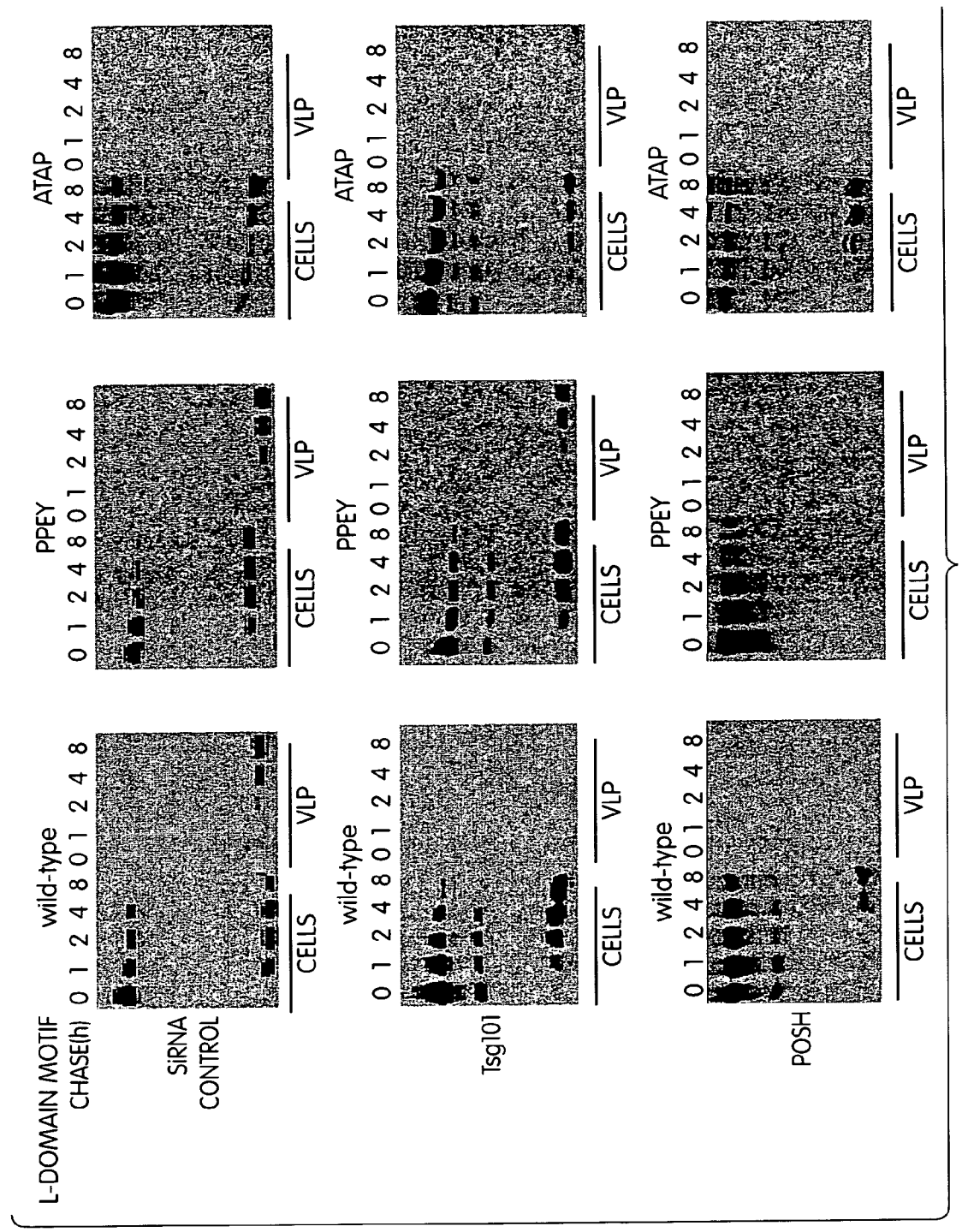
FIG. 20: Human POSH protein mediates both PTAP- and PPEY-mediated viral particle release in the context of HIV. Phosphohimages of SDS-PAGE gels of immunoprecipitations of 35S pulse-chase labeled Gag proteins are presented for cell and viral lysates from transfected HeLa cells. Hela cells were transfected with an HIV-encoding plasmid and siRNA. From left to right: the left panel was transfected with wild-type HIV-encoding plasmid. The middle panel was transfected with an HIV-encoding plasmids which contains a point mutation (PPEE to PPEY). The right panel was transfected with an HIV-encoding plasmids which contains a point mutation in p6 (PTAP to ATAP). From top to bottom: control siRNA (lamin A/C) was transfected to cells in the top panel. siRNA to Tsg101 was transfected to cells in the middle panel and siRNA to POSH was transfected to cells in the bottom panel. The time during the chase period (0, 1, 2, 4 and 8 hours after the pulse) are presented from left to right for each panel.

Results, shown in FIG. 20, demonstrate that the inhibition effect of viral release of knocking down human POSH is independent of specifice HIV L-domain motif. In other words, human POSH appears to be important in both PTAP- and PPEY-mediated viral release. This suggests that inhibiting human POSH level/activity can be potentially effective against inhibihiting the infectivity of any virus containing PTAP or PPEY motifs. HIV (contains PTAP) and Ebola virus (contains PPEY) are examples of such viruses.

6. Effect of RING and SH3 Deletions on HIV-1 Release

Figure 21:
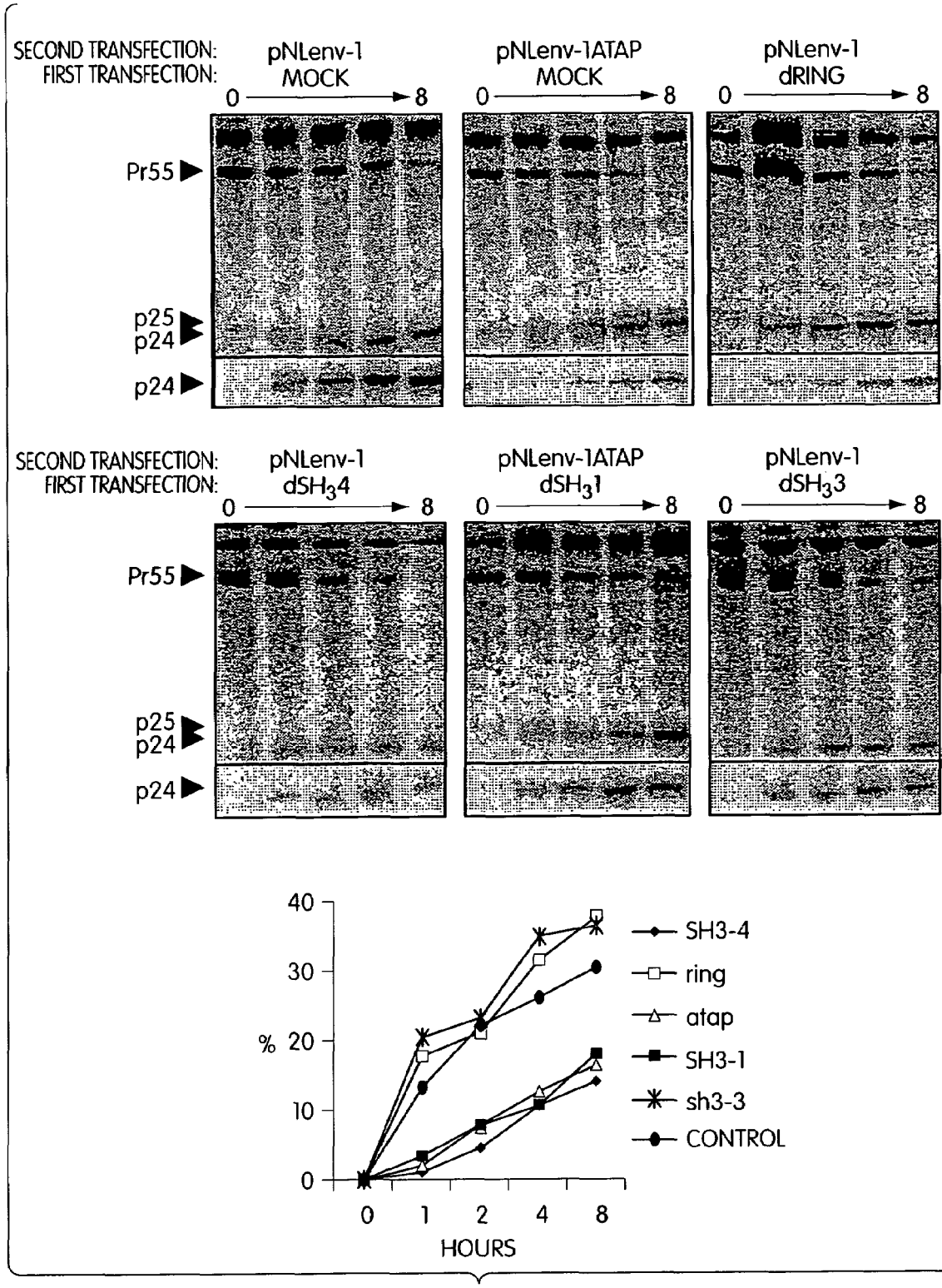
FIG. 21: Deletion of the RING domain and the 4$^{th}$ SH3 domain of human POSH protein inhibits HIV1 viral particle release.

HeLa cells were sequentially transfected (within 48 hours) with a deletion construct of human POSH and pNLenv-1. The deletion constructs used in this experiments were: dRING (RING domain deletion), dSH$_3$4 ($4^{th}$ SH$_3$ domain deletion), dSH$_3$1 ($1^{st}$ SH$_3$ domain deletion) and dsH$^3$3($3^{nd}$ SH$_3$ domain deletion). As controls, Hela cells were also sequentially transfected with mock and pNLenv-1, and mock and pNLenv-1ATAP respectively. 24 hours post transfection cells were subjected to pulse chase studies. Viral proteins were immunoprecipitated from cell lysates and pelleted virions, separated by SDS-PAGE and analyzed by fluorography. Positions of the two major CA products, p24 and p25, are indicated by double arrows. The rate of Pr55 processing was estimated by calculating the ratio of CA versus Pr55 detected intracellularly at different time point. The results, shown in FIG. 21, show that RING deletion in hPOSH leads to complete budding inhibition compare to ATAP mutant control. SH$_3$4 domain deletion effect in the same way as RING deletion.

7. In-Vitro Assay of Human POSH Self-Ubiquitination

Recombinant hPOSH was incubated with ATP in the presence of E1, E2 and ubiquitin as indicated in each lane. Following incubation at 37° C. for 30 minutes, reactions were terminated by addition of SDS-PAGE sample buffer. The samples were subsequently resolved on a 10% polyacrylamide gel. The separated samples were then transferred to nitrocellulose and subjected to immunoblot analysis with an anti ubiquitin polyclonal antibody. The position of migration of molecular weight markers is indicated on the right. Poly-Ub: Ub-hPOSHconjugates, detected as high molecular weight adducts only in reactions containing E1, E2 and ubiquitin. hPOSH-176 and hPOSH-178 are a short and a longer derivatives (respectively) of bacterially expressed hPOSH; C, control E3 preliminary steps in high-throughput screen Objective
1. Test Ub detection with in a Ub chain as function of an E3 (HRD1) and POSH auto-Ubiquitination.
2. Test Boston Biochem reagents.

Materials
1. E1 recombinant from bacculovirus
2. E2 Ubch5c from bacteria
3. Ubiquitin
4. POSH #178 (1-361) gst fusion-purified but degraded
5. POSH # 176 (1-269) gst fusion-purified but degraded
6. hsHRD1 soluble ring containing region
5. Buffer×12 (Tris 7.6 40 mM, DTT 1 mM, MgCl$_2$ 5 mM, ATP 2 uM)
6. Dilution buffer (Tris 7.6 40 mM, DTT 1 mM, ovalbumin 1 ug/ul) protocol

|  | 0.1 ug/ul E1 | 0.5 ug/ul E2 | 5 ug/ul Ub | 0.4 ug/ul 176 | 2.5 ug/u/ 178 | 0.8 ug/ul Hrd1 | Bx12 |
|---|---|---|---|---|---|---|---|
| −E1 (E2 + 176) | — | 0.5 | 0.5 | 1 | — | — | 10 |
| −E2 (E1 + 176) | 1 | — | 0.5 | 1 | — | — | 9.5 |
| −ub (E1 + E2 + 176) | 1 | 0.5 | — | 1 | — | — | 9.5 |
| E1 + E2 + 176 + Ub | 1 | 0.5 | 0.5 | 1 | — | — | 9 |
| −E1 (E2 + 178) | — | 0.5 | 0.5 | — | 1 | — | 10 |
| −E2 (E1 + 178) | 1 | — | 0.5 | — | 1 | — | 9.5 |
| −ub (E1 + E2 + 178) | 1 | 0.5 | — | — | 1 | — | 9.5 |

-continued

|  | 0.1 ug/ul E1 | 0.5 ug/ul E2 | 5 ug/ul Ub | 0.4 ug/ul 176 | 2.5 ug/u/ 178 | 0.8 ug/ul Hrd1 | Bx12 |
|---|---|---|---|---|---|---|---|
| E1 + E2 + 178 + Ub | 1 | 0.5 | 0.5 | — | 1 | —1 | 9 |
| Hrd1, E1 + E2 + Ub | 1 | 0.5 | 0.5 | — | — | 1 | 8.5 |

1. Incubate for 30 minutes at 37° C.
2. Run 12% SDS PAGE gel and transfer to nitrocellulose membrane
3. Incubate with anti-Ubiquitin antibody.

Figure 22:
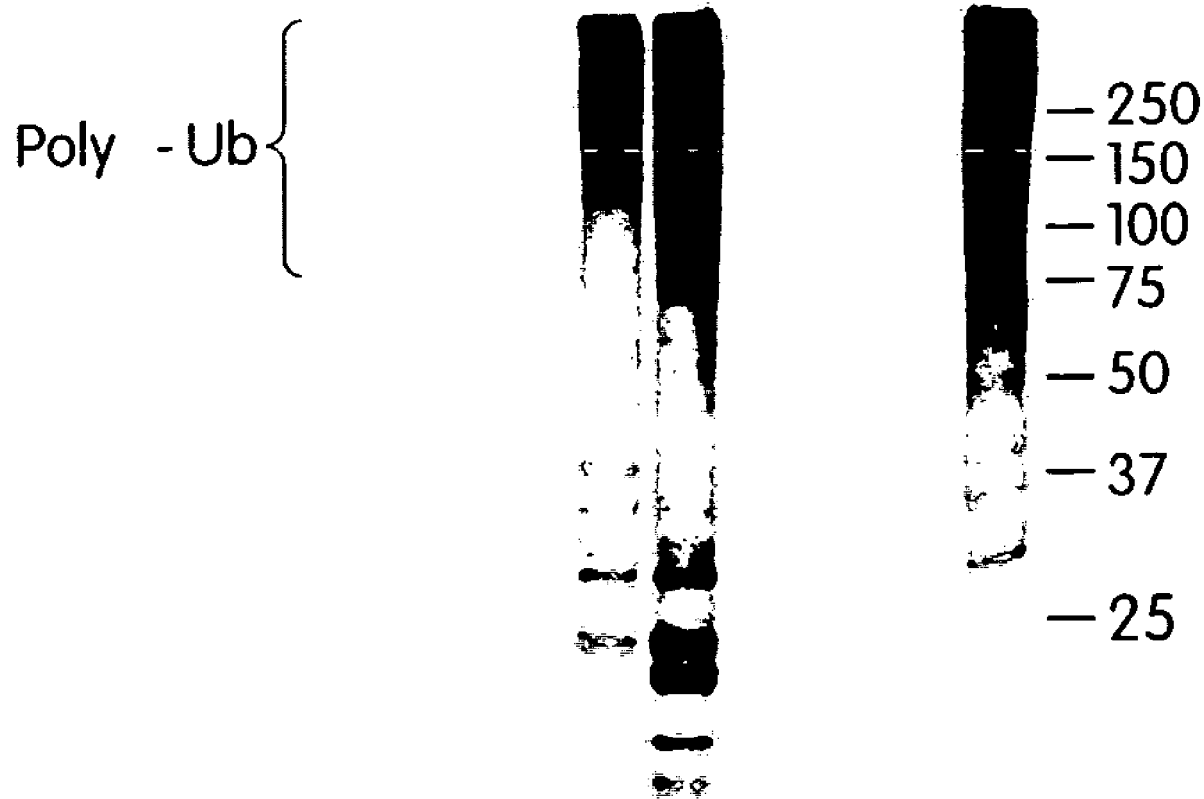
FIG. 22: Human POSH has ubiquitin ligase activity

Results, shown in FIG. 22, demonstrate that human POSH has ubiquitin ligase activity.

8. Co-Immunoprecipitation of hPOSH with Myc-Tagged Activated (V12) and Dominant-Negative (N17) Rac1

Figure 23:
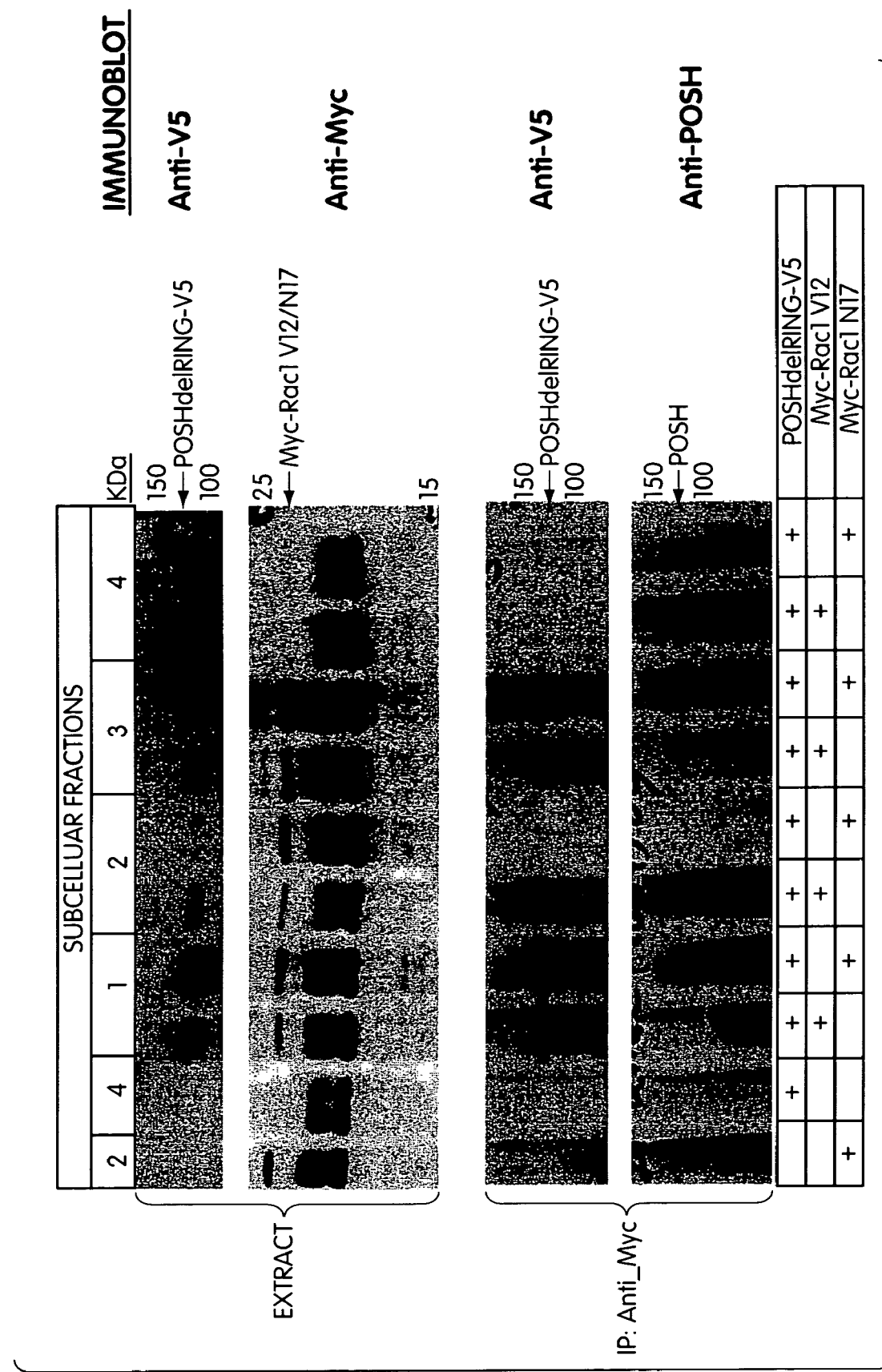
FIG. 23: Human POSH co-immunoprecipitates with RAC1

Hela cells were transfected with combinations of myc-Rac1 V12 or N17 and hPOSHdelRING-V5. 24 hours after transfection (efficiency 80% as measured by GFP) cells were collected, washed with PBS, and swollen in hypotonic lysis buffer (10 mM HEPES pH=7.9, 15 mM KCl, 0.1 mM EDTA, 2 mM MgCl2, 1 mM DTT, and protease inhibitors). Cells were lysed by 10 strokes with dounce homogenizer and centrifuged 3000×g for 10 minutes to give supernatant (Fraction 1) and nucleii. Nucleii were washed with Fraction 2 buffer (0.2% NP-40, 10 mM HEPES pH=7.9, 40 mM KCl, 5% glycerol) to remove peripheral proteins. Nucleii were spun-down and supernatant collected (Fraction 2). Nuclear proteins were eluted in Fraction 3 buffer (20 mM HEPES pH=7.9, 0.42M KCl, 25% glycerol, 0.1 mM EDTA, 2 mM MgCl2, 1 mM DTT) by rotating 30 minutes in cold. Insoluble proteins were spun-down 14000×g and solubilized in Fraction 4 buffer (1% Fos-Choline 14, 50 mM HEPES pH=7.9, 150 mM NaCl, 10% glycerol, 1 mM EDTA, 1.5 mM MgCl2, 2 mM DTT). Half of the total extract was pre-cleared against Protein A sepharose for 1.5 hours and used for IP with 1 μg anti-myc (9E10, Roche 1-667-149) and Protein A sepharose for 2 hours. Immune complexes were washed extensively, and eluted in SDS-PAGE sample buffer. Gels were run, and proteins electro-transferred to nitrocellulose for immunoblot as in FIG. 23. Endogenous POSH and transfected hPOSHdelRING-V5 are precipitated as a complex with Myc-Rac1 V12/N17. Results, shown in FIG. 23, demonstrate that POSH co-immunoprecipitates with Rac1.

9. Knock-Down of hPOSH Entraps HIV Virus Particles in Intracellular Vesicles.

Figure 24:
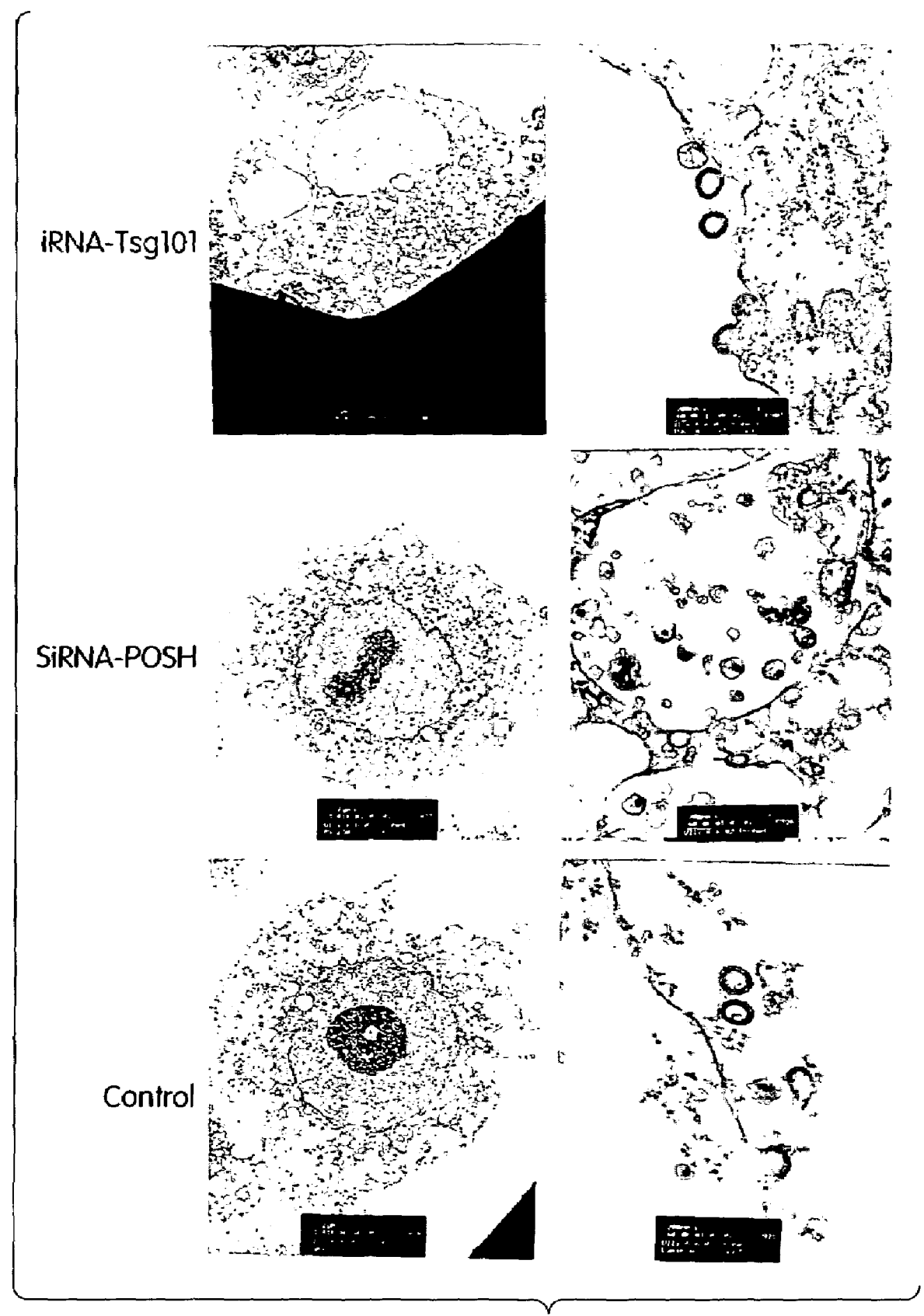
FIG. 24: Knock-down of human POSH entraps HIV virus particles in intracellular vesicles. HIV virus release was analyzed by electron microscopy following siRNA and full-length HIV plasmid transfection. Mature viruses were secreted by cells transfected with HIV plasmid and non-relevant siRNA (control, bottom panel). Knockdown of Tsg101 protein resulted in a budding defect, the viruses that were released had an immature phenotype (top panel). Knockdown of hPOSH levels resulted in accumulation of viruses inside the cell in intracellular vesicles (middle panel).
Figure 25A:
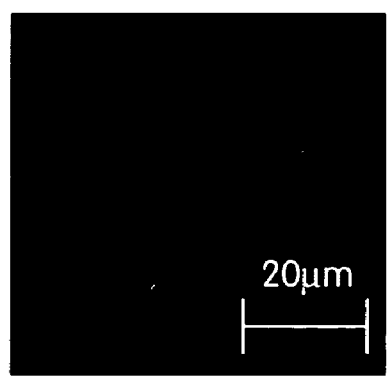
FIG. 25: Human POSH is localized at two sites: one at the nucleus and one at the golgi (C)). After HIV transfection POSH golgi localization is enhanced(D). HeLa and 293T cells were transfected with pNLenv-1. 24 hours post transfection the cells were incubated with primary antibodies against POSH and either with anti-p24 Gag (B) or an organelle marker as follows: BiP-endoplasmatic reticulum (data not shown), GM130-golgi, (C,D) nucleoporin-nuclei matrix (E, F) and histone H1-nucleus (data not shown). Two different flourescence labeled secondary antibodies were used. Specific signals were obtained by laser-scanning confocal microscopy, and individual signals were overlaid to assess their relative positions. POSH is localized to the nucleus (A) and partially colocalized with HIV-1 Gag and the golgi marker outside the nucleus, presumably in the nuclear matrix (B) following transfection.
Figure 25B:
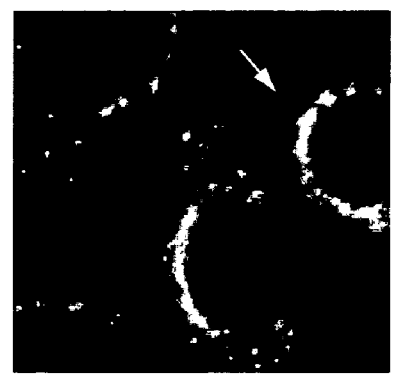
Figure 25C:
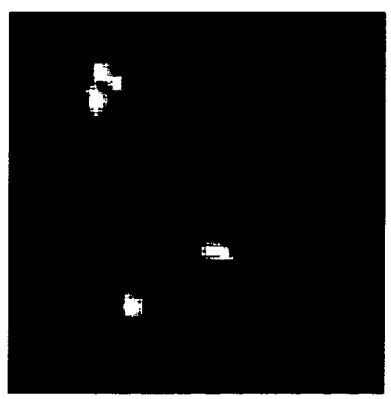
Figure 25D:
Figure 25E:
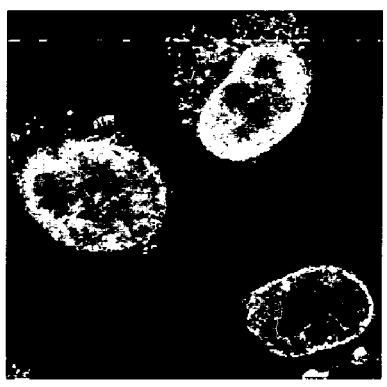
Figure 25F:
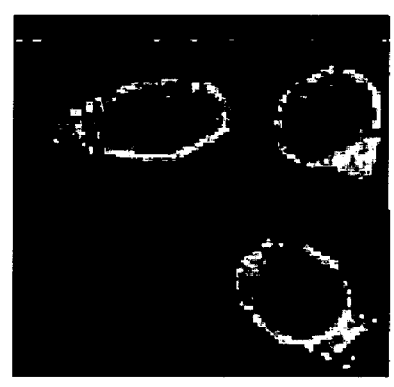

HIV virus release was analyzed by electron microscopy following siRNA and full-length HIV plasmid (missing the envelope coding region) transfection. Mature viruses were secreted by cells transfected with HIV plasmid and non-relevant siRNA (control, lower panel). Knockdown of Tsg101 protein resulted in a budding defect, the viruses that were released had an immature phenotype (upper panel). Knockdown of hPOSH levels resulted in accumulation of viruses inside the cell in intracellular vesicles (middle panel). Results, shown in FIG. 24, indicate that inhibiting hPOSH entraps HIV virus particles in intracellular vesicles. As accumulation of HIV virus particles in the cells accelerate cell death, inhibition of hPOSH therefore destroys HIV reservoir by killing cells infected with HIV.

10. POSH is Localized at Two Sites One at the Nucleai and One at the Golgi (C)). After HIV Transfection Recrotment of POSH to the Golgli is Enhanced(D)

HeLa and 293T cells were transfected with pNenv-1. 24 hours post transfection the cells were incubated with primary antibodies against POSH alongside with either anti-p24 Gag (B) or one of the organelle markers as follows: BiP-endoplasmatic reticulum (data not shown), GM130-golgi, (C,D) nucleoporin-nuclei matrix (E, F) and histone H1-nucleus (data not shown). Two different florescence labled secondary antibodies were used. Specific signals were obtained by laser-scanning confocal microscopy, and individual signals were overlaid to assess their relative positions. As shown in FIG. 7, POSH (A) is localized in the nucleus and partially colocalized with HIV-1 Gag following transfection outside the nucleus, presumably in the nuclear matrix (B).

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A method for testing a ubiquitin-related activity of a POSH (Plenty Of SH3 domains) polypeptide comprising:

forming a mixture compatible with the ubiquitin-related activity comprising: a ubiquitin; a ubiquitin-activating enzyme (E1); a ubiquitin-conjugating enzyme (E2); and a POSH polypeptide; and detecting whether said ubiquitin binds to said POSH polypeptide.

2. The method of claim 1, wherein the POSH polypeptide is selected from the group consisting of SEQ ID NOS: 2 and 26.

3. The method of claim 1, wherein the ubiquitin is detectably labeled.

4. The method of claim 1, wherein the POSH polypeptide is detectably labeled.

5. The method of claim 3 or 4, wherein said label is selected from the group consisting of a radioisotopes, fluorescent compounds, enzymes, and enzyme co-factors.

6. The method of claim 1, wherein the POSH polypeptide has ubiquitin ligase activity and comprises a sequence selected from the group consisting of (a) SEQ ID NO: 26 and (b) a sequence that is at least 95% identical to SEQ ID NO: 26.

* * * * *